United States Patent [19]

Minatoya et al.

[11] 4,138,581

[45] Feb. 6, 1979

[54] 3(HYDROXY OR HYDROXYMETHYL)-4(HYDROXY)-α-(AMINOMETHYL)BENZYL ALCOHOLS

[75] Inventors: Hiroaki Minatoya, East Greenbush, N.Y.; Benjamin F. Tullar, Laurel Park, N.C.; Walter D. Conway, Amherst, N.Y.

[73] Assignee: Sterling Drugs Inc., New York, N.Y.

[21] Appl. No.: 654,700

[22] Filed: Feb. 2, 1976

Related U.S. Application Data

[60] Continuation-in-part of Ser. No. 496,538, Aug. 12, 1974, abandoned, which is a division of Ser. No. 123,834, Mar. 12, 1971, Pat. No. 3,904,671, which is a continuation-in-part of Ser. No. 812,370, Apr. 1, 1969, abandoned.

[51] Int. Cl.$^2$ .............................................. C09F 5/08
[52] U.S. Cl. .................................... 560/109; 260/546; 546/263; 546/285; 546/326; 260/410.5; 560/1; 560/49; 560/55; 560/61; 560/100; 560/105; 560/106; 560/107; 560/108; 560/117; 560/138; 560/221; 560/252; 424/305; 424/309; 424/310; 424/311; 424/314
[58] Field of Search .................... 260/469, 477, 410.5; 560/105, 108, 109, 100, 61, 106, 107

[56] References Cited

U.S. PATENT DOCUMENTS

| | | | |
|---|---|---|---|
| 3,341,594 | 9/1967 | Thoma et al. | 260/307 C |
| 3,657,244 | 4/1972 | Mentrup et al. | 260/479 R |
| 3,714,229 | 1/1973 | Saari et al. | 260/477 |
| 4,010,191 | 3/1977 | Thiele et al. | 260/477 |

FOREIGN PATENT DOCUMENTS

230352 12/1963 Australia.
748178 9/1970 Belgium.
6714191 4/1968 Netherlands.

OTHER PUBLICATIONS

Zolss, Sci. Pharm. 32, 76–92 (1964).
Bretschneider, Montashefte für Chemie, 76, 368–380 (1947); 77, 385–397 (1947), 78, 71–81 (1948).
Daly, J. Med. Chem. 9, 273 (1966).

*Primary Examiner*—Jane S. Myers
*Attorney, Agent, or Firm*—Paul E. Dupont; B. Woodrow Wyatt

[57] ABSTRACT

Mono-, di- and tri-esters of 3-(hydroxy or hydroxymethyl)-4-hydroxy-α-(aminomethyl)benzyl alcohols, obtained by methods involving reduction of the corresponding mono- and di-ester ketones, are useful for producing sympathomimetic effects, such as bronchodilation, of long duration with low cardiovascular stimulating effect, in warm-blooded mammals.

46 Claims, No Drawings

3(HYDROXY OR HYDROXYMETHYL)-4(HYDROXY)-α-(AMINOMETHYL)BENZYL ALCOHOLS

CROSS-REFERENCES TO RELATED APPLICATIONS

This application is a continuation-in-part of our co-pending application Ser. No. 496,539, filed Aug. 12, 1974, now abandoned, which is a division of our co-pending application Ser. No. 123,834, filed Mar. 12, 1971, now U.S. Pat. No. 3,904,671, which is in turn a continuation-in-part of our co-pending application Ser. No. 812,370, filed Apr. 1, 1969, now abandoned.

BACKGROUND OF THE INVENTION

1. Field of the Invention

This invention relates to compositions of matter classified in the art of chemistry as esters of 3-(hydroxy or hydroxymethyl)-4-hydroxy-alpha-(aminomethyl)benzyl alcohols, to a process and intermediates for the preparation of the same, and to a method for producing sympathomimetic effects, for instance, bronchodilation, of long duration in warm-blooded animals by administering said esters.

2. Description of the Prior Art

H. Bretschneider, Monatshefte fur Chemie 76, 368–380 (1947) discloses in most pertinent part 3′,4′-dibutyryloxy-2-(methylamino)acetophenone and 3′,4′-dipropionyloxy-2-(isopropylamino)acetophenone.

H. Bretschneider, Monatschefte fur Chemie 77, 385–397 (1947) discloses in most pertinent part 3,4-bis-(propionyloxy)alpha-(isopropylaminomethyl)benzyl alcohol, and 3,4-bis-(propionyloxy)-alpha-(isopropylaminomethyl)benzyl propionate.

H. Bretschneider, Monatshefte fur Chemie 78, 71–81 (1948) discloses in most pertinent part 3′,4′-dibenzoyloxy-2-(methylamino)acetophenone.

Austrian patent No. 230,352, published Dec. 10, 1963 discloses in most pertinent part a group of substituted alpha-(alkylaminomethyl)benzyl alcohols having the formula:

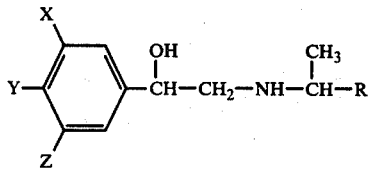

wherein inter alia:

X is a hydroxyl group or an acyloxy group derived from an aliphatic carboxylic acid containing from 2 to 6 carbon atoms;

Y is an acyloxy group derived from an aliphatic carboxylic acid containing from 2 to 6 carbon atoms;

Z is hydrogen; and

R is alkyl.

The most pertinent species disclosed is 3,4-diacetoxyphenyl-2-isopropylamino-ethanol.

G. Zolss, Sci. Pharm. 32, 76–92 (1964) discloses a group of 3,4 and 3,5-diacyloxy-alpha-(aminomethyl)benzyl alcohols including the following pertinent species:

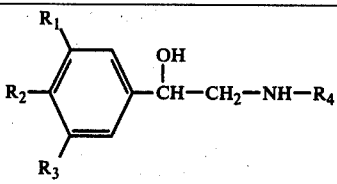

| $R_1$ | $R_2$ | $R_3$ | $R_4$ |
|---|---|---|---|
| $CH_3CO_2$ | $CH_3CO_2$ | H | $CH(CH_3)_2$ |
| $(CH_3)_3CCO_2$ | $(CH_3)_3CCO_2$ | H | H |
| $(CH_3)_2CHCH_2CO_2$ | H | $(CH_3)_2CHCH_2CO_2$ | $CH(CH_3)_2$ |
| $CH_3(CH_2)_7CO_2$ | H | $CH_3(CH_2)_7CO_2$ | H |
| $CH_3(CH_2)_{10}CO_2$ | H | $CH_3(CH_2)_{10}CO_2$ | H |

O. Thoma et al. U.S. Pat. No. 3,341,594, issued September 12, 1967 discloses in pertinent part a group of 3,5-disubstituted-alpha-(alkylaminomethyl)benzyl alcohols and 3′,5′-disubstituted-2-aminoacetophenones having the respective formulas:

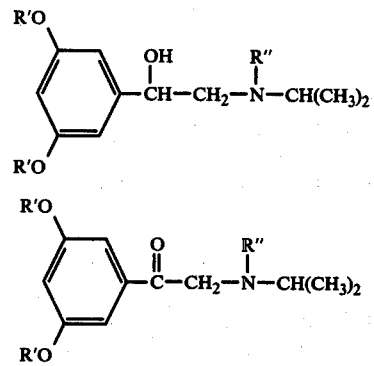

wherein inter alia

R′ is acyl; and

R″ is hydrogen.

The patent discloses no examples of compounds having either of the above formulas wherein R′ is acyl.

A. Mentrup et al. U.S. Pat. Ser. No. 3,657,244, issued Apr. 18, 1972, application filed Oct. 16, 1967, discloses in most pertinent part a group of 2,3,4-trisubstituted-alpha-(alkylaminomethyl)benzyl alcohols and 2′,3′,4′-trisubstituted-2-(alkylamino)acetophenones having the respective formulas

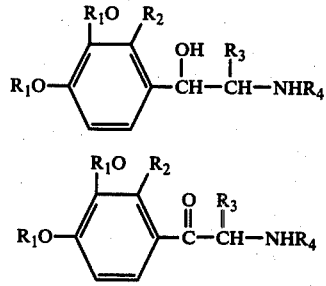

wherein inter alia:

$R_1$ is acyl;

$R_2$ is straight or branched alkyl of 1 to 5 carbon atoms;

$R_3$ is hydrogen or lower alkyl; and $R_4$ is straight or branched alkyl of 1 to 8 carbon atoms or cycloalkyl of 3 to 7 carbon atoms.

The most pertinent species disclosed is 1-(2-methyl-3,4-diacetoxyphenyl)-2-isopropylamino-ethanol.

Draco, Lunds Farmacevtiska AB Netherlands patent publication No. 6,714,191, published Apr. 22, 1968 discloses in most pertinent part 3,5-disubstituted-alpha-(alkylaminomethyl)benzyl alcohols and 3′,5′-disubstituted-2-(alkylamino)acetophenones having the respective formulas

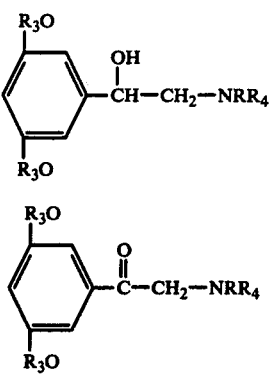

wherein inter alia:
R is tert-butyl or cycloalkyl having from 3 to 6 carbon atoms;
$R_3$ is an acyl group of not more than 5 carbon atoms; and
$R_4$ is hydrogen.
Specifically disclosed are 3,5-diacetoxy-alpha-(tert-butylaminomethyl)benzyl alcohol and 3′,5′-diacetoxy-2-(benzyl-tert-butylamino)acetophenone.

W. Saari et al. U.S. patent Ser. No. 3,714,229, issued Jan. 30, 1973, application filed July 10, 1969, discloses, in most pertinent part, substituted-alpha-(1-aminoethyl)-benzyl alcohols having the formula

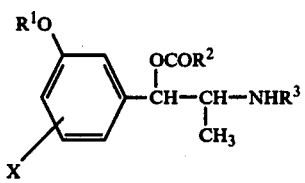

wherein inter alia:
$R^1$ is hydrogen or $R^2CO$
$R^2$ is hydrogen, alkyl, cycloalkyl, alkenyl, phenyl, substituted phenyl or heteroaryl;
$R^3$ is hydrogen or lower alkyl; and
X is $R^2CO_2$.
Also disclosed as intermediates are the compounds having the formula

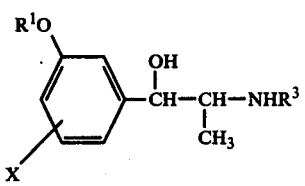

wherein $R^1$ and X have the above-given meaning and $R^3$ is methyl or ethyl. The patent contains no examples of compounds having either of the above formulas wherein X is a carboxylic ester group.

J. W. Daly et al., J. Med. Chem. 9, 273 (1966) disclose 3,4-dibenzoxy-N-methylphenethylamine hydrochloride.

SUMMARY OF THE INVENTION

In a composition aspect, this invention relates to a group of esters of 3,4-dihydroxy-alpha-(amino- and N-substituted amino-methyl)benzyl alcohols and esters of 3-hydroxymethyl-4-hydroxy-alpha-(amino- and N-substituted amino-methyl)benzyl alcohols which produce useful sympathomimetic effects, for example bronchodilation, of long duration in warm-blooded mammals.

In a further composition aspect the present invention provides esters of 3,4-dihydroxyphenyl (amino- and N-substituted amino-methyl) ketones and esters of 3-hydroxymethyl-4-hydroxyphenyl (amino- and N-substituted aminomethyl) ketones which are useful as intermediates in the preparation of the corresponding benzyl alcohols.

In its method aspect this invention is concerned with the method of producing sympathomimetic effects, for instance bronchodilation, of long duration in a warm-blooded mammal which comprises administering to said mammal an effective amount of an ester of a 3,4-dihydroxy-alpha-(amino- and N-substituted amino-methyl)-benzyl alcohol or an ester of a 3-hydroxymethyl-4-hydroxy-alpha-(amino- and N-substituted amino-methyl)benzyl alcohol.

DETAILED DESCRIPTION INCLUSIVE OF THE PREFERRED EMBODIMENTS

The invention sought to be patented resides in one of its composition aspects in the chemical compounds designated as esters of 3,4-dihydroxy-alpha-(amino- and N-substituted amino-methyl)benzyl alcohols which have in the free base form Formula I hereinbelow:

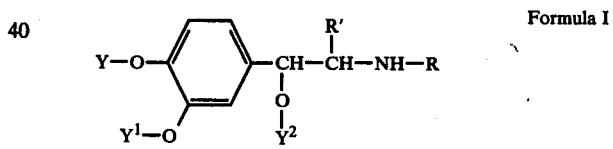

Formula I wherein,
R is hydrogen, alkyl having 1–4 carbon atoms, or cycloalkyl having 3–6 carbon atoms;
R′ is hydrogen or ethyl;
Y is an acyl member which is alkanoyl having 1–22 carbon atoms, alkenoyl having one or two double bonds and having 4–22 carbon atoms, cycloalkyl—$C_nH_{2n}$—CO— having a total of 4–10 carbon atoms of which 3–7 are ring carbon atoms in cycloalkyl and wherein n is zero, one or two, 1- or 2-adamantanecarbonyl, phenoxyacetyl, naphthalenecarbonyl, pyridinecarbonyl, or Z—$C_nH_{2n}$—CO— wherein n is zero, one or two and Z is phenyl or phenyl substituted by 1–3 members of the group consisting of alkyl having 1–4 carbon atoms, alkoxy having 1–4 carbon atoms, halo, trifluoromethyl, dialkylamino having 2–8 carbon atoms, and alkanoylamino having 1–6 carbon atoms; and
$Y^1$ and $Y^2$ are the same or different and are hydrogen or one of the acyl members defined by Y, and
wherein at least one of Y and $Y^1$ contains no less than four carbon atoms when R is tert-butyl or cycloalkyl and no less than seven carbon atoms when R is hydrogen or alkyl other than tert-butyl;

and acid-addition salts thereof.

These compounds are useful as long-acting sympathomimetic agents when administered orally, intratracheally, intraduodenally, or intravenously to warm-blooded mammals.

In another composition aspect, the invention sought to be patented resides in the compounds having in the free base form Formula I hereinabove wherein:

R is hydrogen, alkyl having 1-4 carbon atoms, or cycloalkyl having 3-6 carbon atoms;

R' is hydrogen or ethyl;

Y is an acyl member which is alkanoyl having 1-22 carbon atoms, alkenoyl having one or two double bonds and having 4-22 carbon atoms, cycloalkyl—$C_nH_{2n}$—CO— having a total of 4-10 carbon atoms of which 3-7 are ring carbon atoms in cycloalkyl and wherein n is zero, one or two, 1- or 2-adamantanecarbonyl, phenoxyacetyl, naphthalenecarbonyl, pyridinecarbonyl, or Z—$C_nH_{2n}$—CO— wherein n is zero, one or two and Z is phenyl or phenyl substituted by 1-3 members of the group consisting of alkyl having 1-4 carbon atoms, alkoxy having 1-4 carbon atoms, halo, trifluoromethyl, dialkylamino having 2-8 carbon atoms, and alkanolylamino having 1-6 carbon atoms; and $Y^1$ and $Y^2$ are the same or different and are hydrogen or one of the acyl members defined by Y, at least one of Y and $Y^1$ being Z—$C_nH_{2n}$—CO—;

and acid-addition salts thereof.

These compounds are useful as long-acting sympathomimetic agents when administered orally, intratracheally, intraduodenally, or intravenously to warm-blooded mammals.

The invention sought to be patented resides in yet another composition aspect in the compounds having in the free base form Formula I hereinabove wherein:

R is hydrogen, alkyl having 1-4 carbon atoms, or cycloalkyl having 3-6 carbon atoms;

R' is hydrogen or ethyl;

Y is an acyl member which is alkanoyl having 1-22 carbon atoms, alkenoyl having one or two double bonds and having 4-22 carbon atoms, cycloalkyl—$C_nH_{2n}$—CO— having a total of 4-10 carbon atoms of which 3-7 are ring carbon atoms in cycloalkyl and wherein n is zero, one or two, 1- or 2-adamantanecarbonyl, phenoxyacetyl, naphthalenecarbonyl, or pyridinecarbonyl; and $Y^1$ and $Y^2$ are the same or different and are hydrogen or one of the acyl members defined by Y, and wherein at least one of Y and $Y^1$ contains no less than four carbon atoms when R is tert-butyl or cycloalkyl and no less than seven carbon atoms when R is hydrogen or alkyl other than tert-butyl;

and acid-addition salts thereof.

These compounds are useful as long-acting sympathomimetic agents when administered orally, intratracheally, intraduodenally, or intravenously to warm-blooded mammals.

Preferred embodiments among the foregoing are the compounds having in the free base form Formula I wherein R and R' have the above-given meaning, $Y^2$ is hydrogen and wherein:

(a) Y and $Y^1$ are the same or different and each is Z—$C_nH_{2n}$—CO— wherein n is zero, and Z is phenyl or phenyl substituted by 1-3 members of the group consisting of alkyl having 1-4 carbon atoms, alkoxy having 1-4 carbon atoms, halo, trifluoromethyl, dialkylamino having 2-8 carbon atoms, and alkanoylamino having 1-6 carbon atoms; and acid-addition salts thereof;

(b) One of Y and $Y^1$ is an acyl member which is alkanoyl having 1-22 carbon atoms, and the other is Z—$C_nH_{2n}$—CO— wherein n is zero, and Z is phenyl or phenyl substituted by 1-3 members of the group consisting of alkyl having 1-4 carbon atoms, alkoxy having 1-4 carbon atoms, halo, trifluoromethyl, dialkylamino having 2-8 carbon atoms, and alkanoylamino having 1-6 carbon atoms;

and acid-addition salts thereof;

(c) Y is Z—$C_nH_{2n}$—CO— wherein n is zero, and Z is phenyl or phenyl substituted by 1-3 members of the group consisting of alkyl having 1-4 carbon atoms, alkoxy having 1-4 carbon atoms, halo, trifluoromethyl, dialkylamino having 2-8 carbon atoms, and alkanoylamino having 1-6 carbon atoms; and $Y^1$ is hydrogen;

and acid-addition salts thereof;

(d) Y and $Y^1$ are the same or different and each is an acyl member which is alkanoyl having 1-22 carbon atoms, and wherein at least one of Y and $Y^1$ contains no less than four carbon atoms when R is tert-butyl or cycloalkyl and no less than seven carbon atoms when R is hydrogen or alkyl other than tert-butyl;

and acid-addition salts thereof;

(e) Y is an acyl member which is alkanoyl having 1-22 carbon atoms; and $Y^1$ is hydrogen, and wherein Y contains no less than four carbon atoms when R is tert-butyl or cycloalkyl and no less than seven carbon atoms when R is hydrogen or alkyl other than tert-butyl;

and acid-addition salts thereof.

Particularly preferred embodiments are the compounds having in the free base form Formula I hereinabove wherein R is tert-butyl and R' and $Y^2$ are hydrogen and wherein:

(a) Y and $Y^1$ are the same or different and each is Z—$C_nH_{2n}$—CO— wherein n is zero, and Z is phenyl or phenyl substituted by 1-3 members of the group consisting of alkyl having 1-4 carbon atoms, alkoxy having 1-4 carbon atoms, halo, trifluoromethyl, dialkylamino having 2-8 carbon atoms, and alkanoylamino having 1-6 carbon atoms; and acid-addition salts thereof;

(b) One of Y and $Y^1$ is an acyl member which is alkanoyl having 1-22 carbon atoms, and the other is Z—$C_nH_{2n}$—CO— wherein n is zero, and Z is phenyl or phenyl substituted by 1-3 members of the group consisting of alkyl having 1-4 carbon atoms, alkoxy having 1-4 carbon atoms, halo, trifluoromethyl, dialkylamino having 2-8 carbon atoms, and alkanoylamino having 1-6 carbon atoms; and acid-addition salts thereof;

(c) Y and $Y^1$ are the same or different and each is an acyl member which is alkanoyl having 1-22 carbon atoms and wherein at least one of Y and $Y^1$ contains no less than four carbon atoms;

and acid-addition salts thereof;

and also the compounds having in the free base form Formula I hereinabove wherein:

R is isopropyl;

R' and $Y^1$ are hydrogen; and

Y and $Y^1$ are the same or different and each is Z—$C_nH_{2n}$—CO— wherein n is zero, and Z is phenyl or phenyl substituted by 1-3 members of the group consisting of alkyl having 1-4 carbon atoms, alkoxy having 1-4 carbon atoms, halo, trifluoromethyl, dialkylamino having 2-8 carbon atoms, and alkanoylamino having 1-6 carbon atoms; and acid-addition salts thereof.

The invention sought to be patented resides in another composition aspect in a compound selected from the group consisting of:

3,4-Bis(p-toluyloxy)-alpha-[(1-tert-butylamino)-ethyl]-benzyl alcohol hydrochloride,
3,4-Bis(p-toluyloxy)-alpha-[(1-isopropylamino)-ethyl]-benzyl alcohol hydrochloride,
3,4-Bis(isovaleryloxy)-alpha-[(1-tert-butylamino)-ethyl]benzyl alcohol hydrochloride,
3,4-Bis(pivalyloxy)-alpha-[(1-tert-butylamino)-ethyl]-benzyl alcohol hydrochloride and
3,4-Bis(p-toluyloxy)-alpha-(1-aminoethyl)benzyl alcohol methanesulfonate.

These compounds are useful as long-acting sympathomimetic agents when administered orally, intratracheally, intraduodenally or intravenously to warm-blooded mammals.

In another composition aspect the invention sought to be patented resides in the compounds having in the free base form Formula II hereinbelow:

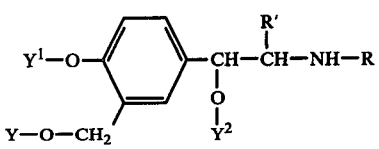

Formula II wherein:
R is hydrogen, alkyl having 1-4 carbon atoms, or cycloalkyl having 3-6 carbon atoms;
R' is hydrogen or alkyl having 1-3 carbon atoms;
Y is an acyl member which is alkanoyl having 1-22 carbon atoms, alkenoyl having one or two double bonds and having 4-22 carbon atoms, cycloalkyl—$C_nH_{2n}$—CO— having a total of 4-10 carbon atoms of which 3-7 are ring carbon atoms in cycloalkyl and wherein n is zero, one or two, 1- or 2-adamantanecarbonyl, phenoxyacetyl, naphthalenecarbonyl, pyridinecarbonyl, or Z—$C_nH_{2n}$—CO— wherein n is zero, one or two and Z is phenyl or phenyl substituted by 1-3 members of the group consisting of alkyl having 1-4 carbon atoms, alkoxy having 1-4 carbon atoms, halo, trifluoromethyl, dialkylamino having 2-8 carbon atoms, and alkanoylamino having 1-6 carbon atoms; and
$Y^1$ and $Y^2$ are the same or different and are hydrogen or one of the acyl members defined by Y, and
wherein at least one of Y and $Y^1$ contains no less than four carbon atoms;
and acid-addition salts thereof.

These compounds are useful as long-acting sympathomimetic agents when administered orally, intratracheally, intraduodenally, or intravenously to warm-blooded mammals.

The invention resides in another of its composition aspects in the chemical compounds designated as 3-($Y^1$-O-)-4-(Y-O-)phenyl (R-NH-)(R')methyl ketones having in the free base form Formula III hereinbelow:

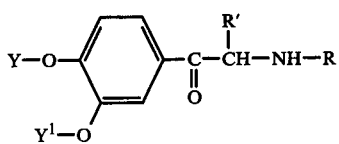

Formula III and 3-(Y-O-$CH_2$-)-4-($Y^1$-O-)phenyl (R-NH-)(R')methyl ketones having in the free base form Formula IV hereinbelow:

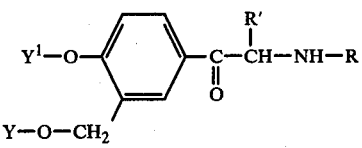

Formula IV wherein, in each of Formulas III and IV, R' is hydrogen or alkyl having 1-3 carbon atoms, and R, Y, and $Y^1$ have the same significance indicated hereinabove. These ester ketones are useful as intermediates in the preparation of the alcohols of Formulas I and II respectively hereinabove.

The invention sought to be patented, in its method aspect, resides in the method of producing sympathomimetic effects in a warm-blooded mammal which comprises administering to said mammal an effective amount of a compound having in the free base form Formula I or Formula II hereinabove.

When R is the formulas herein is alkyl having 1-4 carbon atoms, there are included methyl, ethyl, n-propyl, isopropyl, n-butyl, isobutyl, tert-butyl and sec-butyl. Isopropyl and tert-butyl are preferred.

When R in the formulas herein is cycloalkyl having 3-6 carbon atoms, there are included cyclopropyl, cyclobutyl, cyclopentyl, and cyclohexyl.

When Y, $Y^1$ or $Y^2$ in the formulas herein is alkanoyl containing 1-22 carbon atoms, there are included both unbranched and branched alkanoyl, for example, formyl, acetyl, propionyl, butyryl, isobutyryl, valeryl, isovaleryl, 2-methylbutanoyl, pivalyl, 3-methylpentanoyl, 3,3-dimethylbutanoyl, 2,2-dimethylpentanoyl, docosanoyl, and 7,7-dimethyloctanoyl. The branched alkanoyl groups are preferred over the unbranched alkanoyl groups.

When Y, $Y^1$, or $Y^2$ in the formulas herein is alkenoyl having one or two double bonds and having 4-22 carbon atoms, there are included, for example, crotonyl, 9-octadecenoyl, 2,5-hexadienoyl, 3,6-octadienoyl, 10,13-octadecadienoyl, and 5,13-docosadienoyl.

When Y, $Y^1$, or $Y^2$ in the formulas herein is cycloalkyl-$C_nH_{2n}$-CO-, there are included for example the cycloalkanecarbonyl and cycloalkanealkanoyl groups: cyclopropanecarbonyl, 1-methylcyclopropanecarbonyl, cyclopropaneacetyl, alpha-methylcyclopropaneacetyl, 1-methylcyclopropaneacetyl, 2-amylcyclopropaneacetyl, cyclopropanepropionyl, alpha-methylcyclopropanepropionyl, 2-isobutylcyclopropanepropionyl, 2-hexylcyclopropanecarbonyl, cyclobutanepropionyl, 2-methylcyclobutanecarbonyl, 1,3-dimethylcyclobutanecarbonyl, 3,3-dimethylcyclobutanecarbonyl, cyclobutaneacetyl, 2,2-dimethyl-3-ethylcyclobutaneacetyl, cyclobutanepropionyl, cyclopentanecarbonyl, 1-methyl-3-isopropylcyclopentanecarbonyl, cyclopentanepropionyl, cyclohexanecarbonyl, cyclohexaneacetyl, 4-methylcyclohexaneacetyl, cycloheptanecarbonyl, 4-methylcycloheptaneacetyl, and cycloheptanepropionyl.

When Y, $Y^1$, or $Y^2$ in the formulas herein is (phenyl or substituted phenyl)—$C_nH_{2n}$—CO—, there are included for example benzoyl, phenylacetyl, alpha-phenylpropionyl, beta-phenylpropionyl, p-toluyl, m-toluyl, o-toluyl, o-ethylbenzoyl, p-tert-butylbenzoyl, 3,4-dimethylbenzoyl, 2-methyl-4-ethylbenzoyl, 2,4,6- trimethylbenzoyl, m-methylphenylacetyl, p-isobutylphenylacetyl, beta-(p-ethylphenyl)propionyl, p-anisoyl, m-anisoyl, o-anisoyl, m-isopropoxybenzoyl, p-n-butoxybenzoyl, 3-methoxy-4-ethoxybenzoyl, 3,4,5-trimethoxybenzoyl, 2,4,6-triethoxybenzoyl, p-methoxyphenylacetyl, m-isobutoxyphenylacetyl, 3,4-diethoxyphenylacetyl, beta-(3,4,5-trimethoxyphenyl)propionyl, o-iodobenzoyl, m-bromobenzoyl, p-chlorobenzoyl, p-fluorobenzoyl, 2-bromo-4-chlorobenzoyl, 2,4,6-trichlorobenzoyl, p-chlorophenylacetyl, alpha-(m-bromophenyl)propionyl, p-trifluoromethylbenzoyl, 2,4-di(trifluoromethyl)benzoyl, m-trifluoromethylphenylacetyl, beta-(p-trifluoromethylphenyl)propionyl, 2-methyl-4-methoxy-benzoyl, 3-chloro-4-ethoxybenzoyl, beta-(3-methyl-4-chlorophenyl)propionyl, p-dimethylaminobenzoyl, m-diethylaminobenzoyl, p-dibutylaminobenzoyl, p-(N-methyl-N-ethylamino)benzoyl, o-acetamidobenzoyl, m-propionamidobenzoyl, p-hexanoylaminobenzoyl, 3-chloro-4-acetamidophenylacetyl, and p-acetamidophenylpropionyl.

When Y, $Y^1$ or $Y^2$ in the formulas herein is naphthalenecarbonyl, there are included 1-naphthalenecarbonyl and 2-naphthalenecarbonyl.

When Y, $Y^1$, or $Y^2$ in the formulas herein is pyridinecarbonyl, there are included picolinoyl (2-pyridinecarbonyl), nicotinoyl (3-pyridinecarbonyl), and isonicotinoyl (4-pyridinecarbonyl).

As provided above, in Formula I when R is tert-butyl or cycloalkyl, no more than one of Y and $Y^1$ contains less than four carbon atoms; and when R is hydrogen or alkyl other than tert-butyl, no more than one of Y and $Y^1$ contains less than seven carbon atoms. In Formula II at least one of Y and $Y^1$ contains no less than four carbon atoms.

Due to the presence of the basic amino grouping, the free base forms of the final products represented by Formulas I and II and also of the intermediates represented by Formulas III and IV react with organic and inorganic acids to form acid-addition salts. The acid-addition salt forms are prepared from any organic or inorganic acid. They are obtained in conventional fashion, for instance either by direct mixing of the base with the acid, or, when this is not appropriate, by dissolving either or both of the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluroric acid, hydrochloric acid, hydrobromic acid, hydriodic acid, perchloric acid, nitric acid, sulfuric acid, phosphoric acid, arsenic acid, and the like.

All of the acid-addition salts are useful as sources of the free base form, by reaction with an inorganic base. It will thus be appreciated that if one or more of the characteristics, such as solubility, molecular weight, physical appearance, toxicity, or the like of a given base of acid-addition salt thereof render that form unsuitable for the purpose at hand, it can be readily converted to another, more suitable form. For pharmaceutical purposes, acid-addition salts of the compounds of Formula I and Formula II with relatively non-toxic, pharmaceutically acceptable acid, for example hydrochloric acid, lactic acid, tartaric acid, and the like, are of course employed.

The mono esters of Formulas I and II wherein $Y^1$ is hydrogen are of course amphoteric, having both free phenol and basic amino groups, and thus form salts with both acids and bases.

The manner and process of making and using the invention, and the best mode contemplated by the inventors of carrying out this invention, will now be described so as to enable any person skilled in the art to which it pertains to make and use the same.

The esters of Formula I hereinabove wherein $Y^2$ is hydrogen are obtained in accordance with this invention by reducing an ester ketone of Formula III. Similarly, the esters of Formula II hereinabove wherein $Y^2$ is hydrogen are obtained by reducing an ester-ketone of Formula IV. As will of course be appreciated, in effecting reduction of these ester-ketones of Formulas III and IV to the corresponding ester-alcohols, the use of reducing means resulting in reduction of carboxylic ester groupings must be avoided. Ordinarily, it is preferred to effect the desired reduction either by catalytic hydrogenation in the presence of a noble metal catalyst such as platinum or palladium, or by employing an alkali metal borohydride and a lower alkanol. In those instances where one or both of Y and $Y^1$ in the ester-ketones of Formulas III and IV contain an olefinic double bond, and it is desired to retain this unsaturation in the reduction product (Formula I or II wherein $Y^2$ is hydrogen), the borohydride method is used since, as is well known, catalytic hydrogenation effects reduction of such double bonds.

The catalytic hydrogenation process is conveniently carried out in a suitable solvent, for example ethyl alcohol, at 20-α° C. under pressure, for instance on the order of 20-= pounds of hydrogen pressure per square inch, in the presence of palladium or platinum hydrogenation catalyst. The hydrogenation is continued until the theoretical amount of hydrogen is absorbed as calculated in conventional fashion from drop in hydrogen pressure. A hydrogenation time of four hours or less is generally satisfactory. After removal of the catalyst, the isolation of the ester-alcohol product is effected in conventional manner, as by evaporation of some or all of the solvent from the reaction mixture, collecting the precipitated crude ester-alcohol, and purifying it by recrystallization from a suitable solvent.

In some instances, when applied to the ester ketones of Formula IV, the catalytic hydrogenation method may result in the production of an undesired by-product by reduction of the -(YO—CH-$_{(Y\text{-}O\text{-}CH_2}$—) group to a 3-(CH$_3$—) group. In such cases, for best results it may be preferable to employ the borohydride reduction method.

The ester-ketones of Formulas III and IV used as starting materials in the reduction process described hereinabove are obtained by mono- or di-esterifying the corresponding known and readily available 3,4-dihydroxyphenyl (R—NH—)-(R')methyl ketones of Formula V and 3-hydroxymethyl-4-hydroxyphenyl (R—NH—) (R')methyl ketones of Formula VI, respectively:

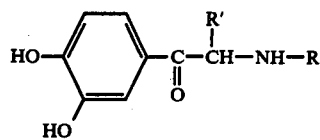

Formula V

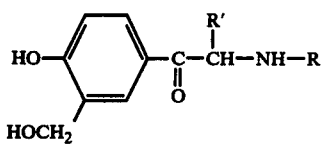

Formula VI wherein in each of Formulas V and VI R and R'have the same significance indicated hereinabove for the corresponding ester ketones of Formulas III and IV.

When R is hydrogen, methyl, or ethyl, to prevent undesired N-acylation it is advantageous to N-benzylate (N,N-dibenzylate when R is hydrogen) the ketone of Formula V before the esterification is carried out. These protective N-benzyl groups can of course be readily removed by catalytic hydrogenation either at the ester ketone state or at the ester alcohol stage (final product), as desired.

For the production of the mono-ester ketones of Formula III wherein $Y^1$ is hydrogen, the starting 3,4-dihydroxyphenyl (R-NH-) (R')-methyl ketone (Formula V) is treated with one molecular equivalent of an acid anhydride or an acid halide of the appropriate carboxylic acid (Y—OH wherein Y has the significance indicated hereinabove), optionally but preferably in the presence of an acid-absorbing medium, in any suitable manner for the acylation of phenolic hydroxyl. In one preferred procedure, the 3,4-dihydroxyphenyl (R—NH—) (R')methyl ketone (Formula V) is treated with two molecular equivalents of an alkali metal lower alkoxide, for instance sodium methoxide, and the resulting alkali metal phenolate is treated with one molecular equivalent of the appropriate acid halide, Y-halogen wherein Y has the same significance indicated hereinabove, for instance the acid chloride, Y—Cl. The 4-hydroxy group in the starting 3,4-dihydroxyphenyl (R—NH—)(R')methyl ketone (Formula V) is more readily acylated than the 3-hydroxyl group, and thus the mono-acylation produces the desired 3-hydroxyphenyl-4- acyloxyphenyl (R—NH—)(R')methyl ketone (Formula III wherein $Y^1$is hydrogen).

The mono-ester ketones of Formula IV wherein $Y^1$is hydrogen are readily obtained either by selectivity esterifying the alcoholic hydroxyl without esterifying the phenolic hydroxyl or by selectively mono-deacylating the diester (obtained as indicated hereinbelow) to convert the 4-acyloxy group to 4-hydroxyl while leaving the 3-acyloxymethyl group intact. The selective esterification is conveniently effected by reacting the ketone of Formula VI with one mole equivalent of a mixed anhydride of the formula $Y^1$—CO—O—CO—CF$_3$, wherein $Y^1$ has the same significance indicated hereinabove, in trifluoroacetic acid. If desired, it is satisfactory and ordinarily more convenient to form the mixed anhydride in situ by mixing the appropriate acid chloride, $Y^1$—Cl, with trifluoroacetic acid. In the selective mono-deacylation method, a diester of Formula IV wherein $Y^1$ is an acyl group is treated at room temperature with a relatively weak organic base such as benzylamine or 2-phenylcyclopropylamine in N,N-dimethylformamide, dimethylsulfoxide, or similar solvent, whereby there is obtained the desired mono-ester of Formula IV wherein $Y^1$ is hydrogen.

The di-ester ketones of Formula III and IV wherein both of Y and $Y^1$ are acyl groups are obtained by acylating the 3-hydroxy-4-acyloxphenyl(R—NH—)(R'λ)methyl ketones (Formula III wherein $Y^1$ is hydrogen) and the 3-(acyloxymethyl)-4-hydroxyphenyl (R—NH—)(R')methyl ketones (Formula IV wherein $Y^1$is hydrogen, obtained as above-described, with one molecular equivalent of an acid anhydride or an acid halide of the appropriate carboxylic acid (Y—OH) which is either different from or the same as the acylating agent used in the first acylation step. As will be appreciated, when it is desired that Y and $Y^1$ in the di-ester ketone (Formula III and Formula IV) be identical, it is generally more convenient to prepare these products by introducing both acyl groups in a single procedure by employing two molecular equivalents of the acylating agent, and thereby proceed directly to the desired diester ketone without isolation of the intermediately-formed mono-ester ketone. When the alkali metal phenolate method is employed, the starting 3,4-dihydroxyphenyl (R—NH—)(R')-methyl ketones of Formula V are of course reacted with two molecular equivalents of alkali metal lower alkoxide so as to replace both of the phenolic hydrogens with the alkali metal, whereas the 3-hydroxymethyl-4-hydroxyphenyl (R—NH—)(R'λ)methyl ketones of Formula VI require use of only one molecular equivalent of alkali metal alkoxide.

In the preparation of the di-ester ketones of Formula IV, a procedure alternative to the one above-described comprises forming a 3-(acyloxymethyl)-4-acyloxy-alpha-(R')-acetophenone, brominating to produce a 3-(acyloxymethyl)-4-acyloxy-alpha-(R')-alpha-bromoacetophenone, and aminating this product at very low temperature, preferably in the range −20° C. to −60° C. with the appropriate aminating agent having the formula R—NH$_2$ $_2$ wherein R has the same significance indicated hereinabove. For the preparation of mono-esters of Formula IV wherein $Y^1$ is hydrogen, this method is readily modified by selective removal of the 4-acyloxy group by treating the 3-(acyloxymethyl)-4-acyloxy-alpha-(R')-acetophenone with benzylamine, or the like weak organic base, in N,N-dimethylformamide, dimethyl sulfoxide, or similar solvent, and subjecting the resulting 3-acyloxymethyl-4-hydroxy-alpha-(R')-acetophenone to the bromination and amination steps as indicated. Alternatively, if it is desired to obtain a mixed di-ester of Formula IV wherein Y and $Y^1$ are different acyl groups, the 3-acyloxymethyl-4-hydroxy-alpha-(R')-acetophenone is appropriately acylated to yield a 3-acyloxymethyl-4-acyloxy:alpha-(R')-acetophenone wherein the acyl groups are different and thereafter subjecting this product to the indicated bromination and amination procedures.

The preparation of the esters of Formula I and Formula II wherein $Y^2$ is acyl are obtained generally by esterification of the corresponding ester-alcohols of Formula I and Formula II wherein $Y^2$ is hydrogen. This esterification is conveniently effected by treatment of an acid(strong)-addition salt of the ester-alcohol, for instance a hydrohalide or methanesulfonate salt, with the appropriate acid halide of formula Y-halogen, preferably the acid halide, Y—Cl, wherein Y has the same significance indicated hereinabove.

The esters of Formula II wherein $Y^1$ is hydrogen and $Y^2$ is acyl are alternatively obtained by preferential hydrolysis of the triesters of Formula II wherein Y, $Y^1$, and $Y^2$ are each acyl to convert the 4-acyloxy group to 4-hydroxy while leaving the other two ester groups intact.

The esters of this invention, having as aboveindicated in free base form the Formulas I and II, when administered orally, intratracheally, intraduodenally, or intravenously to warm-blooded mammals are useful for producing sympathomimetic effects of substantially longer duration than the corresponding unesterified sympathomimetic agents.

Many of the compounds of Formulas I and II have been found to have useful bronchodilator activity, for example:

3,4-bis(butyryloxy)-alpha-(tert-butylaminomethyl)benzyl alcohol hydrochloride,
3,4-bis(isobutyryloxy)-alpha-(tert-butylaminomethyl)benzyl alcohol hydrochloride,
3,4-bis(isovaleryloxy)-alpha-(tert-butylaminomethyl)benzyl alcohol hydrochloride,
3,4-bis(2-methylbutanoyloxy)-alpha-(tert-butylaminomethyl)-benzyl alcohol hydrochloride,
3,4-bis(pivalyloxy)-alpha-(tert-butylaminomethyl)benzyl alcohol hydrochloride,
3,4-bis(3-methylpentanoyloxy)-alpha-(tert-butylaminomethyl)benzyl alcohol hydrochloride,
3,4-bis(3,3-dimethylbutanoyloxy)-alpha-(tert-butylaminomethyl)benzyl alcohol hydrochloride,
3,4-bis(1-methylcyclopropanecarbonyloxy)-alpha-(tert-butylaminomethyl)benzyl alcohol hydrochloride,
3,4-bis(cyclohexanecarbonyloxy)-alpha-(tert-butylaminomethyl)benzyl alcohol hydrochloride,
3,4-bis(benzoyloxy)-alpha-(tert-butylaminomethyl)benzyl alcohol hydrochloride,
3,4-bis(p-toluyloxy)-alpha-(tert-butylaminomethyl)benzyl alcohol methanesulfonate,
3,4-bis(p-anisoyloxy)-alpha-(tert-butylaminomethyl)benzyl alcohol hydrochloride,
3-hydroxy-4-(isovaleryloxy)-alpha-(tert-butylaminomethyl)benzyl alcohol methanesulfonate,
3-hydroxy-4-(pivalyloxy)-alpha-(tert-butylaminomethyl)benzyl alcohol methanesulfonate,
3-(isovaleryloxy)-4-(pivalyloxy)-alpha-(tert-butylaminomethyl)benzyl alcohol hydrochloride,
3,4-bis(p-toluyloxy)-alpha-(isopropylaminomethyl)benzyl alcohol methanesulfonate,
3,4-bis(m-toluyloxy)-alpha-(tert-butylaminomethyl)benzyl alcohol methanesulfonate,
3,4-bis(2,4-dimethylbenzoyloxy)-alpha-(tert-butylaminomethyl)benzyl alcohol methanesulfonate,
3,4-bis(3,5-dimethylbenzoyloxy)-alpha-(tert-butylaminomethyl)benzyl alcohol methanesulfonate,
3,4-bis(p-methoxyphenylacetoxy)-alpha-(tert-butylaminomethyl)benzyl alcohol hydrochloride,
3-hydroxy-4-(p-anisoyloxy)-alpha-(tert-butylaminomethyl)benzyl alcohol hydrochloride,
3-benzoyloxy-4-(p-toluyloxy)-alpha-(tert-butylaminomethyl)benzyl alcohol methanesulfonate,
3,4-bis(p-toluyloxy)-alpha-(methylaminomethyl)benzyl alcohol methanesulfonate,
3,4-bis(p-toluyloxy)-alpha-(aminomethyl)benzyl alcohol methanesulfonate,
3,4-bis(p-toluyloxy)-alpha-[1-(isopropylamino)propyl]benzyl alcohol hydrochloride,
3,4-bis(p-toluyloxy)-alpha-(tert-butylaminomethyl)benzyl acetate methanesulfonate,
3,4-bis(isovaleryloxy)-alpha-[1-(cyclopentylamino)propyl]benzyl alcohol hydrochloride,
3-hydroxy-4-(m-toluyloxy)-alpha-(tert-butylaminomethyl)benzyl alcohol methanesulfonate,
3-hydroxy-4-(2,2-dimethylpentanoyloxy)-alpha-(tert-butylaminomethyl)benzyl alcohol methanesulfonate,
3,4-bis(pivalyloxy)-alpha-[1-(tert-butylamino)ethyl]benzyl alcohol hydrochloride,
3-benzoyloxy-4-(p-anisoyloxy)-alpha-(tert-butylaminomethyl)benzyl alcohol hydrochloride,
3,4-bis(p-toluyloxy)-alpha-[1-(tert-butylamino)propyl]benzyl alcohol hydrochloride,
3-acetoxy-4-(p-anisoyloxy)-alpha-(tert-butylaminomethyl)benzyl alcohol methanesulfonate,
3-(p-toluyloxy)-4-acetoxy-alpha-(tert-butylaminomethyl)benzyl alcohol methanesulfonate,
3-(o-toluyloxy)-4-acetoxy-alpha-(tert-butylaminomethyl)benzyl alcohol methanesulfonate,
3-(1-adamantanecarbonyloxy)-4-acetoxy-alpha-(tert-butylaminomethyl)benzyl alcohol methanesulfonate,
3-(p-anisoyloxy)-4-acetoxy-alpha-(tert-butylaminomethyl)benzyl alcohol methanesulfonate,
3-(pivalyloxymethyl)-4-(pivalyloxy)-alpha-(tert-butylaminomethyl)benzyl alcohol methanesulfonate,
3-(isovaleryloxymethyl)-4-(isovaleryloxy)-alpha-(tert-butylaminomethyl)benzyl alcohol methanesulfonate,
3-(acetoxymethyl)-4-(p-toluyloxy)-alpha-(tert-butylaminomethyl)benzyl alcohol methanesulfonate,
3-(acetoxymethyl)-4-(p-anisoyloxy)-alpha-(tert-butylaminomethyl)benzyl alcohol methanesulfonate,
3-(acetoxymethyl)-4-(1-adamantanecarbonyloxy)-alpha-(tert-butylaminomethyl)benzyl alcohol methanesulfonate,
3,4-bis(benzoyloxy)-alpha-[1-(tert-butylamino)propyl]benzyl alcohol methanesulfonate, and
3,4-bis(p-toluyloxy)-alpha-(tert-butylaminomethyl)benzyl p-toluate methanesulfonate.

Generally speaking, the di-esters of Formula I and Formula II (wherein $Y^1$ is acyl) have longer duration of sympathomimetic action than the corresponding monoesters of Formula I and Formula II (wherein $Y^1$ is hydrogen). Particularly preferred embodiments of this invention are the esters of the sympathomimetic agents, for instance 3,4-dihydroxy-alpha-(isopropylaminomethyl)benzyl alcohol and especially 3,4-dihydroxy-alpha-(tert-butylaminomethyl)benzyl alcohol, which have useful bronchodilator action. These particularly preferred esters, which are those having Formula I wherein R' is hydrogen and R is isopropyl or tert-butyl, not only have longer duration of bronchodilator action than the corresponding unesterified bronchodilator agents, when administered orally, intratracheally, intraduodenally, or intravenously to warm-blooded mammals but also advantageously produce lower cardiovascular effects than the corresponding unesterified compounds. In this group of preferred esters the diesters, especially those wherein one of Y and $Y^1$ is benzoyl or substituted benzoyl and the other is benzoyl, substituted benzoyl, or alkanoyl, afford special advantages.

In carrying out the method aspect of this invention, i.e. the method of producing sympathomimetic effects of long duration in warm-blooded mammals which comprises administering to said mammal an effective amount of an ester having in the free base form Formula I or Formula II hereinabove, the said esters are orally administered in the same manner as the known corresponding unesterified sympathomimetic. Thus, they can be used with any of the pharmaceutically acceptable carriers conventionally employed for oral or parenteral administration of such agents. Ordinarily, they are combined with conventional pharmaceutical solid or liquid diluents and carriers in tablets, capsules, syrups, emulsions, solutions, suspensions or the like. The formulations may contain any of the usual excipients as water, lactose, starch, magnesium stearate, talc, gelatin, calcium carbonate, gums, and the like. An especially preferred method for administering these esters (Formula I and Formula II) is in the form of an aerosol inhalant preparation, for example of the general type conventionally used in aerosol therapy, as in the treatment of bronchospasms, wherein a sympathomimetic agent with effective bronchodilator activity is incorporated with suitable carriers and an inert propellant in a nebulizing unit. A typical formulation of the aerosol type contains, by weight: 0.25 per cent of the ester (Formula I or Formula II) or a suitable pharmaceutically-acceptable salt thereof, 39.75 per cent of U.S.P. ethanol, 48 per cent of dichlorotetrafluoroethane, and 12.00 per cent of dichlorodifluoromethane.

The individual unit dosage can be varied as desired. For general use it is preferred to incorporate, in a solid vehicle, tablet or capsule, about 0.1 to 100 mg. of the ester (Formula I or Formula II); or in a liquid vehicle, about 0.1 to 100 mg. of the ester (Formula I or Formula II) per teaspoonful or, in an aerosol, 0.02 to 2 mg. per actuation. The effective oral dose for producing bronchodilation is in the approximate range 0.002–2.0 mg./kg.

This invention is illustrated by the following examples without, however, being limited thereto.

EXAMPLE 1

A. A mixture of 25 g. of 3,4-dihydroxyphenyl N-tert-butylaminomethyl ketone hydrochloride, 150 ml. of butyric acid saturated with hydrogen chloride, and 150 ml. of butyryl chloride was stirred on a steam bath until a clear solution was obtained (in about six hours) and the solution was heated on the steam bath for one hour. Approximately 50 ml. of solvent was distilled under reduced pressure from the reaction mixture which was then cooled. The mixture was filtered to collect a crystalline solid product which was washed well with diethyl ether and sucked dry under a rubber dam overnight. There was thus obtained 31 g. of 3,4-bis(-butyryloxy)phenyl N-tert-butylaminomethyl ketone hydrochloride as a white crystalline solid which melted at 212–215° C. (dec.)(uncorr.).

B. A mixture of 30 g. of 3,4-bis(butyryloxy)phenyl N-tert-butylaminomethyl ketone hydrochloride, 200 ml. of 90 per cent ethyl alcohol, and 2 g. of 10 per cent palladium-on-charcoal hydrogenation catalyst was hydrogenated for two hours at 50° C. under an initial hydrogen pressure of 50 pounds per square inch. The hydrogenation mixture was filtered to remove the catalyst. The solvent was evaporated from the filtrate under reduced pressure and the resulting residue was taken up in 50 ml. of isopropyl alcohol, allowed to stand overnight at 5° C., and filtered to remove 3 g. of solid. The filtrate was evaporated under reduced pressure, the residue thus obtained was dissolved in 50 ml. of isopropyl acetate, and this solution was filtered to remove a small amount of insoluble solid. When the filtrate was diluted with anhydrous diethyl ether, a solid separated from solution. This solid was collected on a filter. There was thus obtained 20 g. of crude 3,4-bis(butyryloxy)-alpha-(tert-butylaminomethyl)benzyl alcohol hydrochloride. This salt was dissolved in water and then ammonium hydroxide was added, resulting in precipitation of the free base, 3,4-bis(butyryloxy)-alpha-(tert-butylaminomethyl)benzyl alcohol. This precipitate was collected on a filter and washed well first with water and then with n-hexane. This base, which melted at 97–99° C. (uncorr.), was dissolved in isopropyl alcohol and this solution was concentrated under reduced pressure. The resulting residue was dissolved in 30 ml. of isopropyl acetate and there was added ethereal hydrogen chloride solution in an amount affording a slight excess of the required amount of hydrogen chloride for conversion of the base to the hydrochloride. The mixture was cooled and the inside of the container was scratched to induce crystallization. The mixture was diluted with 100 ml. of diethyl ether and the solid precipitate was collected on a filter and washed with anhydrous diethyl ether and dried at 70° C. There was thus obtained 11 g. of 3,4-bis(butyryloxy)-alpha-(tert-butylaminomethyl)benzyl alcohol hydrochloride as a white crystalline solid which melted at 136–138° C. (uncorr.). This salt was soluble in water to the extent of at least 20 per cent. The pH of a 1 per cent aqueous solution of this salt was 6.0; and a precipitate formed when the pH of this solution was raised to 7.0 by addition of N/10 sodium hydroxide solution.

EXAMPLE 2

A. To a mixture of 26 g. of 3,4-dihydroxyphenyl tert-butylaminomethyl ketone hydrochloride in 200 ml. of N,N-dimethylformamide under an atmosphere of nitrogen there was added 17 g. of sodium methoxide. By distillation under reduced pressure, 50 ml. of liquid was removed and the mixture was then cooled and under an atmosphere of nitrogen 25 g. of isobutyryl chloride was added rapidly at 5–25° C. The reaction mixture was stirred at 25° C. for one hour and then was warmed to 70° C. and the solvent was removed by distillation. The resulting residue was slurried in 400 ml. of diethyl ether, and the slurry was filtered to remove about 10 g. of insoluble solid. The ethereal layer in the filtrate was separated, washed with dilute aqueous sodium hydroxide solution and then with water. There was thus obtained an ether solution of 3,4-bis(isobutyryloxy)phenyl tert-butylaminomethyl ketone. To this solution there was added a solution obtained by adding 4 ml. of hydrochloric acid to 25 ml. of water, and the resulting mixture was shaken. The crystalline solid which formed was collected on a filter and dried at 70° C. There was thus obtained 8.5 g. of 3,4-bis(isobutyryloxy)phenyl tert-butylaminomethyl ketone hydrochloride as a white crystalline powder which melted at 221–223° C. (dec.)(uncorr.).

B. By catalytic hydrogenation of 8.5 g. of 3,4-bis-(isobutyryloxy)phenyl tert-butylaminomethyl ketone hydrochloride in 200 ml. of 95 per cent ethyl alcohol in the presence of 2 g. of 10 per cent palladium-on-charcoal catalyst there was obtained 5.0 g. of 3,4-bis-(isobutyryloxy)-alpha-(tert-butylaminomethyl)benzyl alcohol hydrochloride as a white crystalline powder which melted at 190° C. (uncorr.).

EXAMPLE 3

A. A mixture of 25 g. of 3,4-dihydroxyphenyl tert-butylaminomethyl ketone hydrochloride, 100 g. of isovaleryl chloride, and 100 g. of isovaleric acid was stirred on a steam bath for seventy-two hours. The reaction mixture was allowed to stand overnight at room temperature (approximately 25° C.) and then was heated and filtered while hot to remove 18 g. of solid. The filtrate was evaporated to dryness under reduced pressure and the resulting residue was crystallized from isopropyl acetate containing a small amount of acetic acid. There was thus obtained 11.2 g. of 3,4-bis-(isovaleryloxy)phenyl tert-butylaminomethyl ketone hydrochloride as a white crystalline solid which melted at 220-222° C. (uncorr.). After recrystallization of a sample of this compound from isopropyl alcohol the melting point was 224-225° C.

B. By catalytic hydrogenation of 11.2 g. of 3,4-bis-(isovaleryloxy)phenyl tert-butylaminomethyl ketone hydrochloride in 250 ml. of 95 per cent ethyl alcohol in the presence of 2 g. of 10 per cent palladium-on-charcoal catalyst there was obtained 3.6 g. of 3,4-bis-(isovaleryloxy)-alpha-(tert-butylaminomethyl)benzyl alcohol hydrochloride as a white crystalline powder which melted at 173° C. (uncorr.). This salt was soluble in water at 25° C. to the extent of at least 20 per cent. The pH of a 1 per cent aqueous solution was 5.4; and when the pH of this solution was adjusted to 7.0 by addition of N/10 sodium hydroxide solution, a precipitate formed.

EXAMPLE 4

A. A mixture of 26 g. of 3,4-dihydroxyphenyl tert-butylaminomethyl ketone hydrochloride, 50 g. of 2-methylbutanoyl chloride, 100 g. of 2-methylbutanoic acid, and 0.5 g. of aluminum chloride was heated with vigorous stirring at 120° C. for one hour. Then, since evolution of hydrogen chloride from the reaction mixture had slowed considerably, the mixture was heated at 145° C. for two hours. The reaction mixture was concentrated under reduced pressure, the resulting residue was slurried in 300 ml. of boiling acetone, and the slurry was filtered. The solid thus collected, which was 3,4-bis(2-methylbutanoyloxy)phenyl tert-butylaminomethyl ketone hydrochloride, weighed 30 g. and melted at 218-221° C. (uncorr.).

B. By catalytic hydrogenation of 29.5 g. of 3,4-bis(2-methylbutanoyloxy)phenyl tert-butylaminomethyl ketone hydrochloride in 200 ml. of 95 per cent ethyl alcohol in the presence of 2 g. of 10 per cent palladium-on-charcoal catalyst there was obtained 26 g. of 3,4-bis(2-methylbutanoyloxy)-alpha-(tert-butylaminomethyl)-benzyl alcohol hydrochloride as a white crystalline powder which melted at 163-165° C. (uncorr.). The solubility of this salt in water at 25° C. was at least 5 per cent.

EXAMPLE 5

A. Proceeding in a manner similar to that described in part A of Example 2 above, 17 g. of sodium methoxide was interacted with 26 g. of 3,4-dihydroxyphenyl tert-butylaminomethyl ketone hydrochloride in 200 ml. of N,N-dimethylformamide and the resulting sodium phenolate salt was interacted with 24 g. of pivalyl chloride (alternatively designated as trimethylacetyl chloride or 2,2-dimethylpropanoyl chloride). From this acylation reaction there was obtained 3,4-bis(pivalyloxy)phenyl tert-butylaminomethyl ketone which was treated with hydrochloric acid to yield 11.5 g. of 3,4-bis(pivalyloxy)-phenyl tert-butylaminomethyl ketone hydrochloride as a white crystalline solid which melted at 243-244° C. (dec.)(uncorr.). This salt was soluble in water at 25° C. to the extent of at least 1 per cent.

B. By catalytic hydrogenation of 11.7 g. of 3,4-bis(-pivalyloxy)phenyl tert-butylaminomethyl ketone hydrochloride in 200 ml. of 95 per cent ethyl alcohol in the presence of 2 g. of 10 per cent palladium-on-charcoal catalyst there was obtained 8.0 g. of 3,4-bis(pivalyloxy)-alpha-(tert-butylaminomethyl)benzyl alcohol hydrochloride as a white crystalline powder which melted at 249° C. (uncorr.). This salt was soluble in water at 25° C. to the extent of at least 5 per cent.

EXAMPLE 6

A. Proceeding in a manner similar to that described in Example 1A above, 10.4 g. of 3,4-dihydroxyphenyl tert-butylaminomethyl ketone hydrochloride, 24 ml. of 3-methylpentanoyl chloride, and 40 ml. of 3-methylpentanoic acid were interacted to yield 4.5 g. of 3,4-bis(3-methylpentanoyloxy)phenyl tert-butylaminomethyl ketone hydrochloride as a white crystalline solid which melted at 139-140° C. (uncorr.).

B. By catalytic hydrogenation of 4.5 g. of 3,4-bis(3-methylpentanoyloxy) phenyl tert-butylaminomethyl ketone hydrochloride in 100 ml. of anhydrous ethyl alcohol in the presence of 0.5 g. of 10 per cent palladium-on-charcoal catalyst there was obtained 2.7 g. of 3,4-bis(3-methylpentanoyloxy)-alpha-(tert-butylaminomethyl) benzyl alcohol hydrochloride as a white crystalline solid which melted at 139-140° C. (uncorr.). This salt was soluble in water at 25° C. to the extent of at least 5 per cent.

EXAMPLE 7

A. Proceeding in a manner similar to that described in Example 2A above, 26 g. of 3,4-dihydroxyphenyl tert-butylaminomethyl ketone hydrochloride was interacted with 17 g. of sodium methoxide and the resulting sodium phenolate salt was interacted with 25 g. of 3,3-dimethylbutanoyl chloride to yield 7.0 g. of 3,4-bis(3,3-dimethylbutanoyloxy)phenyl tert-butylaminomethyl ketone hydrochloride as a white crystalline solid which melted at 225-228° C. (dec.)(uncorr.).

B. By catalytic hydrogenation of 7.0 g. of 3,4-bis(3,3-dimethylbutanoyloxy) phenyl tert-butylaminomethyl ketone hydrochloride in 200 ml. of 95 per cent ethyl alcohol in the presence of 2 g. of 10 per cent palladium-on-charcoal catalyst there was obtained 6.0 g. of 3,4-bis(3,3-dimethylbutanoyloxy)-alpha-(tert-butylaminomethyl) benzyl alcohol hydrochloride as a white crystalline powder which melted at 226° C. (uncorr.). This salt was soluble in water at 25° C. to the extent of at least 1 per cent.

EXAMPLE 8

A. Proceeding in a manner similar to that described in Example 2A above, 26 g. of 3,4-dihydroxyphenyl tert-butylaminomethyl ketone hydrochloride was interacted with 18 g. of sodium methoxide, and the resulting sodium phenolate salt was interacted with 30 ml. of 2,2-dimethylpentanoyl chloride to yield 17 g. of 3,4-bis(2,2-dimethylpentanoyloxy)phenyl tert-butylaminomethyl ketone hydrochloride as a white crystalline solid which melted at 183-185° C. (uncorr.).

B. By catalytic hydrogenation of 15 g. of 3,4-bis(2,2-dimethylpentanoyloxy) phenyl tert-butylaminomethyl ketone hydrochloride in 200 ml. of 95 per cent ethyl alcohol in the presence of 2 g. of 10 per cent palladium-on-charcoal catalyst there was obtained 3,4-bis(2,2-dimethylpentanoyloxy)-alpha-(tert-butylaminomethyl) benzyl alcohol hydrochloride which by treatment with an excess of 10 per cent ammonium hydroxide was converted to the free base (11 g.). This base was converted to its methanesulfonic acid salt (10g.), a white crystalline powder which melted at 107-109° C. (uncorr.). The methanesulfonate was soluble in water at 25° C. to the extent of at least 5 per cent.

EXAMPLE 9

Following the procedure described above in Example 2A but using decanoyl chloride instead of isobutyryl chloride there is obtained 3,4-bis(decanoyloxy)-phenyl tert-butylaminomethyl ketone; and by interaction of this base with hydrochloric acid there is obtained the hydrochloride salt as a white crystalline solid which decomposed slowly above 235° C.(uncorr.). When this hydrochloride was catalytically hydrogenated, using the procedure described above in Example 2B, there was obtained 3,4-bis(decanoyloxy)-alpha-(tert-butylaminomethyl)benzyl alcohol hydrochloride which was converted to the corresponding free base, a crystalline white solid, m.p. 73-74° C. (uncorr.), and this base was converted to the methanesulfonate salt, a crystalline white solid, m.p. 45-48° C. (uncorr.).

EXAMPLE 10

Following the procedure described above in Example 2A but using tetradecanoyl chloride instead of isobutyryl chloride there is obtained 3,4-bis(tetradecanoyloxy)phenyl tert-butylaminomethyl ketone; and by interaction of this base with methanesulfonic acid there is obtained the methanesulfonate salt. When this methanesulfonate is catalytically hydrogenated, using the procedure described above in Example 2B, there is obtained 3,4-bis(tetradecanoyloxy)-alpha-(tert-butylaminomethyl)benzyl alcohol methanesulfonate.

EXAMPLE 11

Following the procedure described above in Example 2A but using octadecanoyl chloride instead of isobutyryl chloride there is obtained 3,4-bis(octadecanoyloxy)phenyl tert-butylaminomethyl ketone; and by interaction of this base with hydrochloric acid there is obtained the hydrochloride salt as a white crystalline solid, m.p. 180-185° C. (uncorr.). When 14 g. of this hydrochloride was catalytically hydrogenated, using the procedure described above in Example 2B, there was obtained 3,4-bis(octadecanoyloxy)-alpha-(tert-butylaminomethyl)benzyl alcohol hydrochloride as a white solid which melted at 75-78° C. (uncorr.). This hydrochloride was converted to the base by treatment with ammonium hydroxide, and the base was extracted with diethyl ether. The ethereal solution thus obtained was dried over anhydrous calcium sulfate and then treated with 1.5 g. of methanesulfonic acid to yield 6.3 g. of 3,4-bis-(octadecanoyloxy)-alpha-(tert-butylaminomethyl) benzyl alcohol methanesulfonate as a white crystalline solid which melted at 105-108° C. (uncorr.).

EXAMPLE 12

Following the procedure described above in Example 2A but using docosanoyl chloride instead of isobutyryl chloride there is obtained 3,4-bis(docosanoyloxy)-phenyl tert-butylaminomethyl ketone; and by interaction of this base with methanesulfonic acid there is obtained the methanesulfonate salt. When this methanesulfonate is catalytically hydrogenated, using the procedure described above in Example 2B, there is obtained 3,4-bis(docosanoyloxy)-alpha-(tert-butylaminomethyl)-benzyl alcohol methanesulfonate.

EXAMPLE 13

A. A mixture of 5.2 g. of 3,4-dihydroxy tert-butylaminomethyl ketone hydrochloride, 10 ml. of 1-methylcyclopropanecarbonyl chloride, and 20 ml. of 1-methylcyclopropanecarboxylic acid was stirred at 120° C. under slight pressure. After evolution of hydrogen chloride had slowed considerably, the temperature of the reaction mixture was raised to 140° C. for thirty minutes. Approximately 10 ml. of solvent was distilled from the mixture and the residue, which contained a crystalline solid, was mixed with anhydrous diethyl ether and filtered. The solid thus collected, which weighed 7.5 g., was slurried in a water-diethyl ether mixture and the slurry was made basic by addition of ammonium hydroxide. The ether layer was separated, washed with dilute sodium hydroxide solution and then with water, and was shaken with a solution prepared by diluting 3 ml. of concentrated hydrochloric acid to 30 ml. with water. The solid which precipitated was collected on a filter, washed with diethyl ether, and dried at 70° C. to yield 6.5 g. of 3,4-bis-(1-methylcyclopropanecarbonyloxy)phenyl tert-butylaminomethyl ketone hydrochloride as a white crystalline solid which melted at 253-255° C. (dec.)(uncorr.).

B. By catalytic hydrogenation of 6.1 g. of 3,4-bis(1-methylcyclopropanecarbonyloxy) phenyl tert-butylaminomethyl ketone hydrochloride in 200 ml. of 90 per cent ethyl alcohol in the presence of 2 g. of 10 per cent palladium-on-charcoal catalyst there was obtained 2.6 g. of 3,4-bis(1-methylcyclopropanecarbonyloxy)-alpha-(tert-butylaminomethyl) benzyl alcohol hydrochloride as a white crystalline powder which melted at 210-212° C. (uncorr.).

EXAMPLE 14

When cyclopropanecarbonyl chloride and cyclopropanecarboxylic acid are substituted for the 1-methylcyclopropanecarbonyl chloride and 1-methylcyclopropanecarboxylic acid, respectively, in the procedure described in Example 13A above, the acylation product obtained is 3,4-bis(cyclopropanecarbonyloxy)-phenyl tert-butylaminomethyl ketone hydrochloride; and when this product is catalytically hydrogenated using the procedure described in Example 13B above, there is obtained 3,4-bis(cyclopropanecarbonyloxy)-alpha-(tert-butylaminomethyl)benzyl alcohol hydrochloride.

EXAMPLE 15

A. Under an atmosphere of nitrogen, 17.0 g. of sodium methoxide was added to a solution of 26.0 g. of 3,4-dihydroxyphenyl tert-butylaminomethyl ketone hydrochloride in 200 ml. of N,N-dimethylformamide. During this addition the temperature of the mixture rose to 45° C. The mixture was cooled to 0° C. and under an atmosphere of nitrogen 29.1 g. of cyclohexanecarbonyl chloride was added dropwise with stirring at 0–3° C. The reaction mixture was stirred for one hour at room temperature (about 25° C.) and then was poured into a mixture of ice water and diethyl ether. The ether layer was separated, washed successively with water, dilute aqueous sodium hydroxide solution, and water, and dired over anhydrous calcium sulfate. Ethereal hydrogen chloride solution was added to the dry ether solution and the solid which precipitated was collected on a filter. The product thus collected was recrystallized from 200 ml. of isopropyl alcohol to yield 11 g. of 3,4-bis(cyclohexanecarbonyloxy)phenyl tert-butylaminomethyl ketone hydrochloride as a white crystalline solid which melted at 204–210° C. (dec.)(uncorr.).

B. By catalytic hydrogenation of 10.6 g. of 3,4-bis-(cyclohexanecarbonyloxy)phenyl tert-butylaminomethyl ketone hydrochloride in 100 ml. of anhydrous ethyl alcohol in the presence of 1.0 g. of 10 per cent palladium-on-charcoal catalyst there was obtained 8.2 g. of 3,4-bis(cyclohexanecarbonyloxy)alpha-(tert-butylaminomethyl)benzyl alcohol hydrochloride as a white crystalline solid which melted at 212–213° C. (uncorr.). The solubility of this salt in each of water and polyethyleneglycol at 25° C. was less than 0.1 per cent. When a 1 per cent solution of this salt in dimethyl sulfoxide was diluted with three volumes of water, no precipitate formed.

EXAMPLE 16

When cyclobutanecarbonyl chloride is substituted for the cyclohexanecarbonyl chloride in the procedure described in Example 15A above, the acylation product obtained is 3,4-bis(cyclobutanecarbonyloxy)phenyl tert-butylaminomethyl ketone; and when this product is catalytically hydrogenated using the procedure described in Example 15B above, there is obtained 3,4-bis(cyclobutanecarbonyloxy)-alpha-(tert-butylaminomethyl)benzyl alcohol.

EXAMPLE 17

When cyclopentanecarbonyl chloride is substituted for the cyclohexanecarbonyl chloride in the procedure described in Example 15A above, the acylation product obtained is 3,4-bis(cyclopentanecarbonyloxy)phenyl tert-butylaminomethyl ketone; and when this product is catalytically hydrogenated using the procedure described in Example 15B above, there is obtained 3,4-bis(cyclopentanecarbonyloxy)-alpha-(tert-butylaminomethyl)benzyl alcohol.

EXAMPLE 18

When cycloheptanecarbonyl chloride is substituted for the cyclohexanecarbonyl chloride in the procedure described in Example 15A above, the acylation product obtained is 3,4-bis(cycloheptanecarbonyloxy)phenyl tert-butylaminomethyl ketone; and when this product is catalytically hydrogenated using the procedure described in Example 15B above, there is obtained 3,4-bis(cycloheptanecarbonyloxy)-alpha-(tert-butylaminomethyl)benzyl alcohol.

EXAMPLE 19

When 2-hexylcyclopropanecarbonyl chloride is substituted for the cyclohexanecarbonyl chloride in the procedure described in Example 15A above, the acylation product obtained is 3,4-bis(2-hexylcyclopropanecarbonyloxy)phenyl tert-butylaminomethyl ketone; and when this product is catalytically hydrogenated using the procedure described in Example 15B above, there is obtained 3,4-bis(2-hexylcyclopropanecarbonyloxy)-alpha-(tert-butylaminomethyl)-benzyl alcohol.

EXAMPLE 20

When 1-methyl-3-isopropylcyclopentanecarbonyl chloride is substituted for the cyclohexanecarbonyl chloride in the procedure described in Example 15A above, the acylation product obtained is 3,4-bis(1-methyl-3-isopropylcyclopentanecarbonyloxy)phenyl tert-butylaminomethyl ketone; and when this product is catalytically hydrogenated using the procedure described in Example 15B above, there is obtained 3,4-bis(1-methyl-3-isopropylcyclopentanecarbonyloxy)-alpha-(tert-butylaminomethyl)benzyl alcohol.

EXAMPLE 21

When 1,3-dimethylcyclobutanecarbonyl chloride is substituted for the cyclohexanecarbonyl chloride in the procedure described in Example 15A above, the acylation product obtained is 3,4-bis(1,3-dimethylbutanecarbonyloxy)phenyl tert-butylaminomethyl ketone; and when this product is catalytically hydrogenated using the procedure described in Example 15B above, there is obtained 3,4-bis(1,3-dimethylcyclobutanecarbonyloxy)-alpha-(tert-butylaminomethyl)benzyl alcohol.

EXAMPLE 22

When 2-amylcyclopropaneacetyl chloride is substituted for the cyclohexanecarbonyl chloride in the procedure described in Example 15A above, the acylation product obtained is 3,4-bis(2-amylcyclopropaneacetoxy)phenyl tert-butylaminomethyl ketone; and when this product is catalytically hydrogenated using the procedure described in Example 15B above, there is obtained 3,4-bis(2-amylcyclopropaneacetoxy)-alpha-(tert-butylaminomethyl)benzyl alcohol.

EXAMPLE 23

When 2,2-dimethyl-3-ethylcyclobutaneacetyl chloride is substituted for the cyclohexanecarbonyl chloride in the procedure described in Example 15A above, the acylation product obtained is 3,4-bis(2,2-dimethyl-3-ethylcyclobutaneacetoxy)phenyl tert-butylaminomethyl ketone; and when this product is catalytically hydrogenated using the procedure described in Example 15B above, there is obtained 3,4-bis(2,2-dimethyl-3-ethylcyclobutaneacetoxy)-alpha-(tert-butylaminomethyl)benzyl alcohol.

EXAMPLE 24

Following the procedure described above in Example 15A but using cyclohexaneacetyl chloride instead of cyclohexanecarbonyl chloride the acylation product obtained is 3,4-bis(cyclohexaneacetoxy)phenyl tert-butylaminomethyl ketone; and when this product is catalytically hydrogenated, using the procedure described above in Example 15B, there is obtained 3,4-bis(cyclohexaneacetoxy)-alpha-(tert-butylaminomethyl)benzyl alcohol.

EXAMPLE 25

When 4-methylcycloheptaneacetyl chloride is substituted for the cyclohexanecarbonyl chloride in the procedure described in Example 15A above, the acylation product obtained is 3,4-bis(4-methylcycloheptaneacetoxy)phenyl tert-butylaminomethyl ketone; and when this product is catalytically hydrogenated using the procedure described in Example 15B above, there is obtained 3,4-bis(4-methylcycloheptaneacetoxy)-alpha-(tert-butylaminomethyl)benzyl alcohol.

EXAMPLE 26

When 2-isobutylcyclopropanepropionyl chloride is substituted for the cyclohexanecarbonyl chloride in the procedure described in Example 15A above, the acylation product obtained is 3,4-bis(2-isobutylcyclopropanepropionyloxy)phenyl tert-butylaminomethyl ketone; and when this product is catalytically hydrogenated using the procedure described in Example 15B above, there is obtained 3,4-bis(2-isobutylcyclopropanepropionyloxy)-alpha-(tert-butylaminomethyl)benzyl alcohol.

EXAMPLE 27

Following the procedure described above in Example 15A but using cycloheptanepropionyl chloride instead of cyclohexanecarbonyl chloride the acylation product obtained is 3,4-bis(cycloheptanepropionyloxy)phenyl tert-butylaminomethyl ketone; and when this product is catalytically hydrogenated, using the procedure described above in Example 15B, there is obtained 3,4-bis(cycloheptanepropionyloxy)-alpha-(tert-butylaminomethyl)benzyl alcohol.

EXAMPLE 28

Following the procedure described above in Example 15A using alpha-methylcyclopropaneacetyl chloride instead of cyclohexanecarbonyl chloride the acylation product obtained is 3,4-bis(alpha-methylcyclopropaneacetoxy)phenyl tert-butylaminomethyl ketone; and when this product is catalytically hydrogenated, using the procedure described above in Example 15B, there is obtained 3,4-bis(alpha-methylcyclopropaneacetoxy)-alpha-(tert-butylaminomethyl)benzyl alcohol.

EXAMPLE 29

A. To 26 g. of 3,4-dihydroxyphenyl tert-butylaminomethyl ketone hydrochloride in 200 ml. of dioxane there was added rapidly 20 g. of potassium hydroxide in 50 ml. of methanol. One-half of the solvent was distilled from the resulting mixture under reduced pressure and then 29 g. of benzoyl chloride was dripped in at 5-10° C. during a period of thirty minutes. The reaction mixture was stirred for another half-hour at 10° C., after which the solvent was distilled off under reduced pressure. The residue thus obtained was slurried with a mixture of 100 ml. and 400 ml. of diethyl ether, and the slurry was filtered to remove 12 g. of insoluble solid. The ether layer in the filtrate was separated, washed with water, dilute aqueous sodium hydroxide solution, and water, and then was shaken with a solution of 7 ml. of concentrated hydrochloric acid in 50 ml. of water. The mixture was cooled in ice and the precipitate which formed was collected on a filter and washed with a few ml. of water and then with diethyl ether, and dried at 70° C. There was thus obtained 11.0 g. of 3,4-bis(benzoyloxy)phenyl tert-butylaminomethyl ketone hydrochloride as a white crystalline solid which melted at 215-218° C. (dec.)(uncorr.).

B. By catalytic hydrogenation of 11 g. of 3,4-bis(benzoyloxy)phenyl tert-butylaminomethyl ketone hydrochloride in 200 ml. of anhydrous ethyl alcohol in the presence of 1.0 g. of 10 per cent palladium-on-charcoal catalyst there was obtained 6.0 g. of 3,4-bis(benzoyloxy)-alpha-(tert-butylaminomethyl)benzyl alcohol hydrochloride which crystallized from a diethyl etheracetic acid-isopropyl acetate mixture as a white solid which melted at 214-216° C. (uncorr.). The solubility of this salt in each of dimethylsulfoxide and glycerol formal at 25° C. was 1 per cent or more; and when a 1 per cent solution of this salt in each of these solvents was diluted with three volumes of water, no precipitate formed in either instance.

EXAMPLE 30

A. Under an atmosphere of nitrogen, 26 g of 3,4-dihydroxyphenyl tert-butylaminomethyl ketone hydrochloride was mixed with 17 g. of sodium methoxide in 200 ml . of N,N-dimethylformamide and 50 ml of solvent was distilled off below 40° C. under reduced pressure. Then 31 g. of p-toluyl chloride was dripped in at 5-10° C. The solvent was distilled from the reaction mixture under reduced pressure, the resulting residue was slurried in a mixture of water and diethyl ether, and the slurry was filtered to remove 9.5 g of insoluble solid. The ether layer in the filtrate, which contained 3,4-bis(p-toluyloxy)phenyl tert-butylaminomethyl ketone, was separated, washed with water and dilute sodium hydroxide, and then was shaken with a solution obtained by diluting 4 ml. of concentrated hydrochloric acid with water to a volume of 30 ml. After the mixture had stood for one hour at room temperature, the precipitate which had formed was collected on a filter, washed with diethyl ether, and recrystallized from isopropyl alcohol. There was thus obtained 14.0 g. of 3,4-bis(p-toluyloxy)phenyl tert-butylaminomethyl ketone hydrochloride as a white crystalline solid which melted at 221-224° C. (uncorr.). The solubility of this salt in water at 25° C. was less than 0.1 per cent.

B. By catalytic hydrogenation of 13.5 g. of 3,4-bis(p-toluyloxy)phenyl tert-butylaminomethyl ketone hydrochloride in 220 ml. of anhydrous ethyl alcohol at room temperature in the presence of 2.0 g. of 10 per cent palladium-on-charcoal catalyst until one mole equivalent of hydrogen was absorbed (about 30 min. required), there was obtained 8.0 g. of crude 3,4-bis(p-toluyloxy)-alpha-(tert-butylaminomethyl)benzyl alcohol hydrochloride as a pulvurulent solid which by treatment with an excess of 10 per cent ammonium hydroxide was converted to the free base, which weighed 4.3 g. and melted at 80-84° C. This base was converted to its methanesulfonic acid salt (4.3 g.), a white crystalline powder which melted at 170-172° C. (uncorr.). The methanesulfonate was soluble in dimethyl sulfoxide to the extent of at least 1 per cent; and when a 1 per cent solution of dimethyl sulfoxide was diluted with three volumes of water, no precipitate formed.

C. To a solution of 1.1 g. of 3,4-bis(p-toluyloxy)phenyl tert-butylaminomethyl ketone methanesulfonate (m.p. 185-187° C. (uncorr.) obtained by reacting the free base with methanesulfonic acid) in 20 ml. of anhydrous methyl alcohol at 5° C. under an atmosphere of nitrogen there was added with stirring 100 mg. of dry sodium borohydride. After five minutes the reaction was quenched with about fifteen drops of glacial acetic acid to bring the pH of the mixture to approximately 6. The mixture was evaporated to dryness, diluted with 200 ml. of diethyl ether, and washed with 100 ml. of 5 per cent aqueous sodium bicarbonate solution, followed by washing successively with water and water saturated with sodium chloride. The aqueous washes were combined and extracted with diethyl ether and this extract was combined with the ethereal solution, dried over sodium sulfate, and evaporated to yield 1 g. of colorless oil. This oil, which was 3,4-bis(p-toluyloxy)-alpha-(tert-butylaminomethyl)benzyl alcohol, was diluted with 70 ml. of anhydrous diethyl ether and 0.14 ml. of methanesulfonic acid was added. A white precipitate formed on cooling. The mixture was concentrated to a volume of about 25 ml. and filtered. The white crystalline solid thus obtained, which weighed 1.1 g., was 3,4-bis(p-toluyloxy)-alpha-(tert-butylaminomethyl)benzyl alcohol methanesulfonate, identical with the product described above in part B. The corresponding acetate salt was a white solid, m.p. 110° C. (uncorr.).

EXAMPLE 31

Following the procedure described above in Example 29A but using p-tert-butylbenzoyl chloride instead of benzoyl chloride there is obtained 3,4-bis(p-tert-butylbenzoyloxy)phenyl tert-butylaminomethyl ketone; and by interaction of this base with hydrochloric acid there is obtained the hydrochloride salt. When this hydrochloride is catalytically hydrogenated, using the procedure described above in Example 29B, there is obtained 3,4-bis(p-tert-butylbenzoyloxy)-alph-(tert-butylaminomethyl)benzyl alcohol hydrochloride.

EXAMPLE 32

Following the procedure described above in Example 29A but using 2-methyl-4-ethylbenzoyl chloride instead of benzoyl chloride there is obtained 3,4-bis(2-methyl-4-ethylbenzoyloxy)phenyl tert-butylaminomethyl ketone; and by interaction of this base with hydrochloric acid there is obtained the hydrochloride salt. When this hydrochloride is catalytically hydrogenated, using the procedure described above in Example 29B, there is obtained 3,4-bis(2-methyl-4-ethylbenzoyloxy)-alpha-(tert-butylaminomethyl)benzyl alcohol hydrochloride.

EXAMPLE 33

A. Proceeding in a manner similar to that described in Example 30A above, 26 g. of 3,4-dihydroxyphenyl tert-butylaminomethyl ketone hydrochloride was reacted with 17 g. of sodium methoxide in 200 ml. of N,N-dimethylformamide, and the resulting sodium phenolate salt was interacted with p-anisoyl chloride to yield 12.3 g of 3,4-bis(p-anisoyloxy)phenyl tert-butylaminomethyl ketone hydrochloride as a white crystalline solid which melted at 205–208° C. (uncorr.).

B. By catalytic hydrogenation of 12.0 g of 3,4-bis(p-anisoyloxy)phenyl tert-butylaminomethyl ketone hydrochloride in 300 ml.of anhydrous ethyl alcohol in the presence of 2.0 g. of 10 percent palladium-on-charcoal catalyst there was obtained 6.2 g of 3,4-bis(p-anisoyloxy)-alpha-(tert-butylaminomethyl)benzyl alcohol hydrochloride as a white crystalline solid which melted at 165° C. (uncorr.). The solubility of this salt in polyethyleneglycol 200 at 25° C. was less than 1 percent. When 1 percent solutions of this salt in each of dimethyl sulfoxide and glycerol formal were diluted with three volumes of water, no precipitate formed.

EXAMPLE 34

Following the procedure described above in Example 30A but using p-ethoxybenzoyl chloride instead of p-toluyl chloride there is obtained 3,4-bis(p-ethoxybenzoyloxy)phenyl tert-butylaminomethyl ketone; and by interaction of this base with hydrochloric acid there is obtained the hydrochloride salt. When this hydrochloride is catalytically hydrogenated, using the procedure described above in Example 30B, there is obtained 3,4-bis(p-ethoxybenzoyloxy)-alpha-(tert-butylaminomethyl)benzyl alcohol hydrochloride.

EXAMPLE 35

Following the procedure described above in Example 30A but using p-acetamidobenzoyl chloride instead of p-toluyl chloride there is obtained 3,4-bis(p-acetamidobenzoyloxy)phenyl tert-butylaminomethyl ketone; and by interaction of this base with hydrobromic acid there is obtained the hydrobromide salt. When this hydrobromide is catalytically hydrogenated, using the procedure described above in Example 30B, there is obtained 3,4-bis(p-acetamidobenzoyloxy)-alpha-(tert-butylaminomethyl)benzyl alcohol hydrobromide.

EXAMPLE 36

When 3,4,5-tributoxybenzoyl chloride is substituted for the p-toluyl chloride in the procedure described in Example 30A above, there is obtained 3,4-bis(3,4,5-tributoxybenzoyloxy)phenyl tert-butylaminomethyl ketone; and by interaction of this base with hydrochloric acid there is obtained the hydrochloride salt. When this hydrochloride is catalytically hydrogenated using the procedure described in Example 30B above, there is obtained 3,4-bis(3,4,5-tributoxybenzoyloxy)-alpha-(tert-butylaminomethyl)benzyl alcohol hydrochloride.

EXAMPLE 37

Following the procedure described above in Example 30A but using 3,5-dimethoxy-4-ethoxybenzoyl chloride instead of p-toluyl chloride there is obtained 3,4-bis(3,5-dimethoxy-4-ethoxybenzothoxyl)phenyl tert-butylaminomethyl ketone; and by interaction of this base with hydrochloric acid there is obtained the hydrochloride salt. When this hydrochloride is catalytically hydrogenated, using the procedure described above in Example 30B, there is obtained 3,4-bis(3,5-dimethoxy-4-ethoxybenzoyloxy)-alpha-(tert-butylaminomethyl)benzyl alcohol hydrochloride.

EXAMPLE 38

Following the procedure described above in Example 30A but using 2-bromo-5-chlorobenzoyl chloride instead of p-toluyl chloride there is obtained 3,4-bis(2-bromo-5-chlorobenzoyloxy)phenyl tert-butylaminomethyl ketone; and by interaction of this base with hydrochloric acid there is obtained the hydrochloride salt. When this hydrochloride is catalytically hydrogenated, using the procedure described above in Example 30B, there is obtained 3,4-bis(2-bromo-5-chlorobenzoyloxy)-alpha-(tert-butylaminomethyl)benzyl alcohol hydrochloride.

EXAMPLE 39

Following the procedure described above in Example 30g. but using 2,3,4,-trichlorobenzoyl chloride instead of p-toluyl chloride there is obtained 3,4-bis(2,3,4-trichlorobenzoyloxy)phenyl tert-butylaminomethyl ketone; and ml. of this base with methanesulfonic acid ml. is obtained the methanesulfonate salt. When this methanesulfonate is catalytically hydrogenated, using the procedure described above in Example 30B, there is obtained 3,4-bis(2,3,4-trichlorobenzoyloxy)-alpha-(tert-butylaminomethyl)benzyl alcohol methanesulfonate. g.

EXAMPLE 40

When 2,3,5-trifluorobenzoyl chloride is substituted for the p-toluyl chloride in the procedure described in Example 30A above, the product obtained is 3,4-bis(2,3,5-trifluorobenzoyloxy)phenyl tert-butylaminomethyl ketone; and by interaction of this base with hydrochloric acid there is obtained the hydrochloride salt. When this hydrochloride is catalytically hydrogenated using the procedure described in Example 30B above, there is obtained 3,4-bis(2,3,5-trifluorobenzoyloxy)-alpha-(tert-butylaminomethyl)benzyl alcohol hydrochloride.

EXAMPLE 41

When 3,5-bis(trifluoromethyl)benzoyl chloride is substituted for the p-toluyl chloride in the procedure described in Example 30A above, the product obtained is 3,4-bis[3,5-bis-(trifluoromethyl)benzoyloxy]phenyl tert-butylaminomethyl ketone; and by interaction of this base with hydrochloric acid there is obtained the hydrochloride salt. When this hydrochloride is catalytically hydrogenated using the procedure described in Example 30B above, there is obtained 3,4-bis[3,5-bis(trifluoromethyl)benzoyloxy]-alpha-(tert-butylaminomethyl)benzyl alcohol hydrochloride.

EXAMPLE 42

Following the procedure described above in Example 30A but using 2-ethoxy-5-fluorobenzoyl chloride instead of p-toluyl chloride there is obtained 3,4-bis(2-ethoxy-5-fluorobenzoyloxy)phenyl tert-butylaminomethyl ketone; and by interaction of this base with hydrochloric acid there is obtained the hydrochloride salt. When this hydrochloride is catalytically hydrogenated, using the procedure described above in Example 30B, there is obtained 3,4-bis(2-ethoxy-5-fluorobenzoyloxy)-alpha-(tert-butylaminomethyl)benzyl alcohol hydrochloride.

EXAMPLE 43

Following the procedure described above in Example 30A but using 2,6-dimethyl-4-propoxybenzoyl chloride instead of p-toluyl chloride there is obtained 3,4-bis(2,6-dimethyl-4-propoxybenzoyloxy)phenyl tert-butylaminomethyl ketone; and by interaction of this base with hydrochloric acid there is obtained the hydrochloride salt. When this hydrochloride is catalytically hydrogenated, using the procedure described above in Example 30B, there is obtained 3,4-bis(2,6-dimethyl-4-propoxybenzoyloxy)-alpha-(tert-butylaminomethyl)benzyl alcohol hydrochloride.

EXAMPLE 44

When 2-chloro-3-methoxy-4-methylbenzoyl chloride is substituted for the p-toluyl chloride in the procedure described in Example 30A above, the product obtained is 3,4-bis(2-chloro-3-methoxy-4-methylbenzoyloxy)phenyl tert-butylaminomethyl ketone; and by interaction of this base with hydrochloric acid there is obtained the hydrochloride salt. When this hydrochloride is catalytically hydrogenated using the procedure described in Example 30B above, there is obtained 3,4-bis(2-chloro-3-methoxy-4-methylbenzoyloxy)-alpha-(tert-butylaminomethyl)benzyl alcohol hydrochloride.

EXAMPLE 45

Following the procedure described above in Example 30A but using phenylacetyl chloride instead of p-toluyl chloride there is obtained 3,4-bis(phenylacetoxy)phenyl tert-butylaminomethyl ketone; and by interaction of this base with hydrochloric acid there is obtained the hydrochloride salt. When this hydrochloride is catalytically hydrogenated, using the procedure described above in Example 30B, there is obtained 3,4-bis(phenylacetoxy)O-alpha-(tert-butylaminomethyl)-benzyl alcohol hydrochloride.

EXAMPLE 46

Following the procedure described above in Example 30A but using p-ethylphenylacetyl chloride instead of p-toluyl chloride there is obtained 3,4-bis(p-ethylphenylacetoxy)phenyl tert-butylaminomethyl ketone; and by interaction of this base with hydrochloric acid there is obtained the hydrochloride salt. When this hydrochloride is catalytically hydrogenated, using the procedure described above in Example 30B, there is obtained 3,4-bis(p-ethylphenylacetoxy)-alpha-(tert-butylaminomethyl)benzyl alcohol hydrochloride.

EXAMPLE 47

Following the procedure described above in Example 30A but using 2,5-dimethyl-4-methoxyphenylacetyl chloride instead of p-toluyl chloride there is obtained 3,4-bis(2,5-dimethyl-4-methoxyphenylacetoxy)phenyl tert-butylaminomethyl ketone; and by interaction of this base with hydrochloric acid there is obtained the hydrochloride salt. When this hydrochloride is catalytically hydrogenated, using the procedure described above in Example 30B, thee is obtained 3,4-bis(2,5-dimethyl-4-methoxyphenylacetoxy)alpha-(tert-butylaminomethyl)-benzyl alcohol hydrochloride.

EXAMPLE 48

Following the procedure described above in Example 30A but using 2-bromo-4,5-diethoxyphenylacetyl chloride instead of p-toluyl chloride there is obtained 3,4-bis(2-bromo-4,5-diethoxyphenylacetoxy)phenyl tert-butylaminomethyl ketone; and by interaction of this base with hydrochloric acid there is obtained the hydrochloride salt. When this hydrochloride is catalytically hydrogenated, using the procedure described above in Example 30B, there is obtained 3,4-bis(2-bromo-4,5-diethoxyphenylacetoxy)-alpha-(tert-butylaminomethyl)-benzyl alcohol hydrochloride.

EXAMPLE 49

Following the procedure described above in Example 30A but using β-phenylpropionyl chloride instead of p-toluyl chloride there is obtained 3,4-bis(β-phenylpropionyloxy)phenyl tert-butylaminomethyl ketone; and by interaction of this base with hydrochloric acid there is obtained the hydrochloride salt. When this hydrochloride is catalytically hydrogenated, using the procedure described above in Example 30B, there is obtained 3,4-bis(β-phenylpropionyloxy)-alpha-(tert-butylaminomethyl)benzyl alcohol hydrochloride.

EXAMPLE 50

Following the procedure described above in Example 30A but using β-(2-bromo-4-methoxyphenyl)propionyl chloride instead of p-toluyl chloride there is obtained 3,4-bis[β-(2-bromo-4-methoxyphenyl)propionyloxy]phenyl tert-butylaminomethyl ketone; and by interaction of this base with hydrochloric acid there is obtained the hydrochloride salt. When this hydrochloride is catalytically hydrogenated, using the procedure described above in Example 30B, there is obtained 3,4-bis[β-(2-bromo-4-methoxyphenyl)propionyloxy]-alpha-(tert-butylaminomethyl)benzyl alcohol hydrochloride.

EXAMPLE 51

Following the procedure described above in Example 30A but using 2-naphthalenecarbonyl chloride instead of p-toluyl chloride there is obtained 3,4-bis(2-naphthalenecarbonyloxy)phenyl tert-butylaminomethyl ketone; and by interaction of this base with hydrochloric acid there is obtained the hydrochloride salt. When this hydrochloride is catalytically hydrogenated, using the procedure described above in Example 30B, there is obtained 3,4-bis(2-naphthalenecarbonyloxy)-alpha-(tert-butylaminomethyl)benzyl alcohol hydrochloride.

EXAMPLE 52

Following the procedure described above in Example 30A but using phenoxyacetyl chloride instead of p-toluyl chloride there is obtained 3,4-bis(phenoxyacetoxy)phenyl tert-butylaminomethyl ketone; and by interaction of this base with hydrochloric acid there is obtained the hydrochloride salt. When this hydrochloride is catalytically hydrogenated, using the procedure described above in Example 30B, there is obtained 3,4-bis(phenoxyacetoxy)-alpha-(tert-butylaminomethyl)-benzyl alcohol hydrochloride.

EXAMPLE 53

Following the procedure described above in Example 30A but using p-diethylaminobenzoyl chloride instead of p-toluyl chloride there is obtained 3,4-bis(p-diethylaminobenzoyloxy)phenyl tert-butylaminomethyl ketone; and by interaction of this base with hydrochloric acid there is obtained the hydrochloride salt. When this hydrochloride is catalytically hydrogenated, using the procedure described above in Example 30B, there is obtained 3,4-bis(p-diethylaminobenzoyloxy)-alpha-(tert-butylaminomethyl)benzyl alcohol hydrochloride.

EXAMPLE 54

Following the procedure described above in Example 30A but using nicotinoyl chloride instead of p-toluyl chloride there is obtained 3,4-bis(nicotinoyloxy)phenyl tert-butylaminomethyl ketone; and by interaction of this base with hydrochloric acid there is obtained the hydrochloride salt. When this hydrochloride is catalytically hydrogenated, using the procedure described above in Example 30B, there is obtained 3,4-bis(nicotinoyloxy)-alpha-(tert-butylaminomethyl) benzyl alcohol hydrochloride.

EXAMPLE 55

Following the procedure described above in Example 2A but using crotonoyl chloride instead of isobutyryl chloride there is obtained 3,4-bis(crotonoyloxy)phenyl tert-butylaminomethyl ketone; and by interaction of this base with hydrochloric acid there is obtained the hydrochloride salt. When this hydrochloride is reduced with sodium borohydride, using the procedure described above in Example 30C, there is obtained 3,4-bis(crotonoyloxy)-alpha-(tert-butylaminomethyl)benzyl alcohol hydrochloride.

EXAMPLE 56

Following the procedure described above in Example 2A but using 9-octadecenoyl chloride instead of isobutyryl chloride there is obtained 3,4-bis(9-octadecenoyloxy)phenyl tert-butylaminomethyl ketone; and by interaction of this base with hydrochloric acid there is obtained the hydrochloride salt. When this hydrochloride is reduced with sodium borohydride using the procedure described above in Example 30C, there is obtained 3,4-bis(9-octadecenoyloxy)-alpha-(tert-butylaminomethyl)benzyl alcohol hydrochloride.

EXAMPLE 57

Following the procedure described above in Example 2A but using 5,13-docosadienoyl chloride instead of isobutyryl chloride there is obtained 3,4-bis(5,13-docosadienoyloxy)phenyl tert-butylaminomethyl ketone; and by interaction of this base with hydrochloric acid there is obtained the hydrochloride salt. When this hydrochloride is reduced with sodium borohydride, using the procedure described above in Example 30C, there is obtained 3,4-bis(5,13-docosadienoyloxy)-alpha-(tert-butylaminomethyl)-benzyl alcohol hydrochloride.

EXAMPLE 58

A. Under an atmosphere of nitrogen, 8.1 g. of sodium methoxide was added to 13 g. of 3,4-dihydroxyphenyl tert-butylaminomethyl ketone hydrochloride in 200 ml. of dimethylformamide and 50 ml. of solvent was distilled from the reaction mixture under reduced pressure. Then under an atmosphere of nitrogen 7.8 g. of isovaleryl chloride was dripped in at 20–25° C. and the reaction mixture was stirred at 25° C. for one hour. The solvent was distilled off under reduced pressure and the resulting residue was taken up in a mixture of 500 ml. of water, 3 ml. of 35 percent aqueous sodium hydroxide solution, and 200 ml. of diethyl ether. The ether layer was separated and discarded. The aqueous layer was acidified with acetic acid and the precipitate which formed was collected on a filter and washed well with water and n-hexane. There was thus obtained 12 g. of 3-hydroxy-4-(isovaleryloxy)phenyl tert-butylaminomethyl ketone. This base was slurried in 500 ml. of anhydrous ethyl alcohol and with stirring there was added 68 percent methanesulfonic acid in an amount (5 ml.) sufficient to produce a persistent acidic reaction in the slurry, which was then stirred until a heavy precipitate formed. The precipitate was collected on a filter and washed with ethyl alcohol and diethyl ether. There was thus obtained 8.1 g. of 3-hydroxy-4-(isovaleryloxy)phenyl tert-butylaminomethyl ketone methanesulfonate as a white crystalline solid which melted at 242–245° C.(dec.)(uncorr.).

B. By catalytic hydrogenation of 8.1 g. of 3-hydroxy-4-(isovaleryloxy)phenyl tert-butylaminomethyl ketone methanesulfonate suspended in 250 ml. of 95 percent ethyl alcohol in the presence of 3.0 g. of 10 percent palladium-on-charcoal catalyst there was obtained 4.8 g. of 3-hydroxy-4-(isovaleryloxy)-alpha-(tert-butylaminomethyl)benzyl alcohol methanesulfonate as a white crystalline solid which melted at 148–150°

C.(uncorr.). The solubility of this salt in water at 25° C was at least 5 percent.

EXAMPLE 59

A. Following a procedure similar to that described in Example 58A above, 260 g. of 3,4-dihydroxyphenyl tert-butylaminomethyl ketone hydrochloride was reacted with 170 g. of sodium methoxide in 2 kg. of N,N-dimethylformamide, and the resulting sodium phenolate was interacted with 160 g. of pivalyl chloride to yield 250 g. of 3-hydroxy-4-(pivalyloxy)phenyl tert-butylaminomethyl ketone. The hydrochloride of this base was a white crystalline solid which melted at 268–270° C. (dec.)(uncorr.), and the methanesulfonate of the base was a white crystalline solid which melted at 260–263° C. (dec.)(uncorr.).

B. By catalytic hydrogenation of 18 g. of 3-hydroxy-4-(pivalyloxy)phenyl tert-butylaminomethyl ketone methanesulfonate suspended in one liter of 95 percent ethyl alcohol in the presence of 3 g. of 10 percent palladium-on-charcoal catalyst there was obtained 10.0 g. of 3-hydroxy-4-(pivalyloxy)-alpha-(tert-butylaminomethyl)benzyl alcohol methanesulfonate as a white crystalline solid which melted at 175–177° C.(uncorr.).

EXAMPLE 60

By interacting 13 g. of 3,4-dihydroxyphenyl tert-butylaminomethyl ketone hydrochloride with 8 ml. of 3,3-dimethylbutanoyl chloride in 35 ml. of trifluoroacetic acid at room temperature, there was obtained 3-hydroxy-4-(3,3-dimethylbutanoyloxy)phenyl tert-butylaminomethyl ketone trifluoroacetate which was converted to the free base by treatment with ammonium hydroxide; and by interaction of this base with methanesulfonic acid there was obtained the methanesulfonate salt, m.p. 240–245° C. (dec.). When this methanesulfonate was catalytically hydrogenated, using the procedure described above in Example 58B, there was obtained 3-hydroxy-4-(3,3-dimethylbutanoyloxy)-alpha-(tert-butylaminomethyl)benzyl alcohol methanesulfonate as a white crystalline solid which melted at 176–178° C.(uncorr.)

EXAMPLE 61

Following the procedure described above in Example 58A but using 7,7-dimethyloctanoyl chloride instead of isovaleryl chloride there is obtained 3-hydroxy-4-(7,7-dimethyloctanoyloxy)-phenyl tert-butylaminomethyl ketone; and by interaction of this base with hydrochloric acid there is obtained the hydrochloride salt. When this hydrochloride is catalytically hydrogenated, using the procedure described above in Example 58B, there is obtained 3-hydroxy-4-(7,7-dimethyloctanoyloxy)-alpha-(tert-butylaminomethyl)benzyl alcohol hydrochloride.

EXAMPLE 62

When dodecanoyl chloride is substituted for the isovaleryl chloride in the procedure described in Example 58A above, the product obtained is 3-hydroxy-4-(dodecanoyloxy)phenyl tert-butylaminomethyl ketone; by interaction of this base with hydrochloric acid there is obtained the hydrochloride salt. When this hydrochloride is catalytically hydrogenated using the procedure described in Example 58B above, there is obtained 3-hydroxy-4-(dodecanoyloxy)-alpha-(tert-butylaminomethyl)benzyl alcohol hydrochloride.

EXAMPLE 63

When 2,2,17,17-tetramethyloctadecanoyl chloride is substituted for the isovaleryl chloride in the procedure described in Example 58A above, the product obtained is 3-hydroxy-4-(2,2,17,17-tetramethyloctadecanoyloxy)phenyl tert-butylaminomethyl ketone hydrochloride; and by interaction of this base with hydrochloric acid there is obtained the hydrochloride salt. When this hydrochloride is catalytically hydrogenated using the procedure described in Example 58B above, there is obtained 3-hydroxy-4-(2,2,17,17-tetramethyloctadecanoyloxy)-alpha-(tert-butylaminomethyl)benzyl alcohol hydrochloride.

EXAMPLE 64

Following the procedure described above in Example 58A but using 1-methylcyclopropanecarbonyl chloride instead of isovaleryl chloride there is obtained 3-hydroxy-4-(1-methylcyclopropanecarbonyloxy)phenyl tert-butylaminomethyl ketone; and by interaction of this base with hydrochloric acid there is obtained the hydrochloride salt. When this hydrochloride is catalytically hydrogenated, using the procedure described above in Example 58B, there is obtained 3-hydroxy-4-(1-methylcyclopropanecarbonyloxy)-alpha-(tert-butylaminomethyl)benzyl alcohol hydrochloride.

EXAMPLE 65

Following the procedure described above in Example 58A but using cycloheptanecarbonyl chloride instead of isovaleryl chloride there is obtained 3-hydroxy-4-(cycloheptanecarbonyloxy)phenyl tert-butylaminomethyl ketone; and by interaction of this base with hydrochloric acid there is obtained the hydrochloride salt. When this hydrochloride is catalytically hydrogenated, using the procedure described above in Example 58B, there is obtained 3-hydroxy-4-(cycloheptanecarbonyloxy)-alpha-(tert-butylaminomethyl)benzyl alcohol hydrochloride.

EXAMPLE 66

Following the procedure described above in Example 58A but using cyclohexaneacetyl chloride instead of isovaleryl chloride there is obtained 3-hydroxy-4-(cyclohexaneacetoxy)phenyl tert-butylaminomethyl ketone; and by interaction of this base with hydrochloric acid there is obtained the hydrochloride salt. When this hydrochloride is catalytically hydrogenated, using the procedure described above in Example 58B, there is obtained 3-hydroxy-4-(cyclohexaneacetoxy)-alpha-(tert-butylaminomethyl)benzyl alcohol hydrochloride.

EXAMPLE 67

Following the procedure described above in Example 58A but using cyclopentanepropionyl chloride instead of isovaleryl chloride there is obtained 3-hydroxy-4-(cyclopentanepropionyloxy)phenyl tert-butylaminomethyl ketone; and by interaction of this base with hydrochloric acid there is obtained the hydrochloride salt. When this hydrochloride is catalytically hydrogenated, using the procedure described above in Example 58B, there is obtained 3-hydroxy-4-(cyclopentanepropionyloxy)-alpha-(tert-butylaminomethyl)benzyl alcohol hydrochloride.

EXAMPLE 68

Following the procedure described above in Example 58A but using nicotinoyl chloride instead of isovaleryl chloride there is obtained 3-hydroxy-4-(nicotinoyloxy)phenyl tert-butylaminomethyl ketone; and by interaction of this base with hydrochloric acid there is obtained the hydrochloride salt. When this hydrochloride is catalytically hydrogenated, using the procedure described above in Example 58B, there is obtained 3-hydroxy-4-(nicotinoyloxy)-alpha-(tert-butylaminomethyl)benzyl alcohol hydrochloride.

EXAMPLE 69

A. Following a procedure similar to that described in Example 58A above, 13 g. of 3,4-dihydroxyphenyl tert-butylaminomethyl ketone hydrochloride was reacted with 8.1 g. of sodium methoxide in 200 ml. of N,N-dimethylformamide, and the resulting sodium phenolate was interacted with 8.5 g. of p-toluyl chloride to yield 3-hydroxy-4-(p-toluyloxy)phenyl tert-butylaminomethyl ketone. This base was converted to the methanesulfonate by treatment, in 200 ml. of warm N,N-dimethylformamide, with methanesulfonic acid. The 3-hydroxy-4-(p-toluyloxy)phenyl tert-butylaminomethyl ketone methanesulfonate thus obtained was a white crystalline solid which weighed 12 g. and melted at 265° C. (dec.-)(uncorr.).

B. By catalytic hydrogenation of 12 g. of 3-hydroxy-4-(p-toluyloxy)phenyl tert-butylaminomethyl ketone methanesulfonate in 1 liter of 95 percent ethyl alcohol in the presence of 4 g. of palladium-on-charcoal catalyst there was obtained 7.4 g. of 3-hydroxy-4-(p-toluyloxy)-alpha-(tert-butylaminomethyl)benzyl alcohol methanesulfonate as a white crystalline powder which melted at 203–205° C. (uncorr.). The solubility of this salt in water at 25° C. was at least 5 percent.

EXAMPLE 70

Following the procedure described above in Example 58A but using 2,3,4-trichlorobenzoyl chloride instead of isovaleryl chloride there is obtained 3-hydroxy-4-(2,3,4-trichlorobenzoyloxy)phenyl tert-butylaminomethyl ketone; and by interaction of this base with hydrochloric acid there is obtained the hydrochloride salt. When this hydrochloride is catalytically hydrogenated, using the procedure described above in Example 58B, there is obtained 3-hydroxy-4-(2,3,4-trichlorobenzoyloxy)-alpha-(tert-butylaminomethyl)benzyl alcohol hydrochloride.

EXAMPLE 71

A. Following a procedure similar to that described in Example 2A above, when 3-hydroxy-4-(pivalyloxy)phenyl tert-butylaminomethyl ketone is interacted with one equivalent of sodium methoxide and the resulting sodium phenolate salt is reacted with isovaleryl chloride there is obtained 3-(isovaleryloxy)-4-(pivalyloxy)phenyl tert-butylaminomethyl ketone, which reacts with hydrochloric acid to yield the hydrochloride salt as a white crystalline solid, m.p. 216–220° C. (uncorr.).

B. By catalytic hydrogenation of 7.7 g. of 3-(isovaleryloxy)-4-(pivalyloxy)phenyl tert-butylaminomethyl ketone hydrochloride in 200 ml. of 95 percent ethyl alcohol in the presence of 2.0 g. of 10 percent palladium-on-charcoal catalyst there was obtained 6.1 g. of 3-(isovaleryloxy)-4-(pivalyloxy)-alpha-(tert-butylaminomethyl)benzyl alcohol hydrochloride as a white crystalline solid which melted at 202–204° C. (uncorr.). The solubility of this salt in water at 25° C. was at least 5 percent.

EXAMPLE 72

Following a procedure similar to that described in Example 2A above, when 3-hydroxy-4-(pivalyloxy)phenyl tert-butylaminomethyl ketone is interacted with one equivalent of sodium methoxide and the resulting sodium phenolate salt is reacted with pivalyl chloride there is obtained 3,4-bis(pivalyloxy)phenyl tert-butylaminomethyl ketone, which reacts with hydrochloric acid to yield the hydrochloride salt. When this hydrochloride is catalytically hydrogenated, using the procedure described above in Example 2B, there is obtained 3,4-bis(pivalyloxy)-alpha-(tert-butylaminomethyl)benzyl alcohol hydrochloride. The ketone intermediate and the alcohol product obtained in this manner are identical with the ketone and the alcohol described above in Example 5A and 5B, respectively.

EXAMPLE 73

Following a procedure similar to that described in Example 2A above, when 3-hydroxy-4-(pivalyloxy)phenyl tert-butylaminomethyl ketone is interacted with one equivalent of sodium methoxide and the resulting sodium phenolate salt is reacted with decanoyl chloride there is obtained 3-(decanoyloxy)-4-(pivalyloxy)phenyl tert-butylaminomethyl ketone which reacts with hydrochloric acid to yield the hydrochloride salt. When this hydrochloride is catalytically hydrogenated, using the procedure described above in Example 2B, there is obtained 3-(decanoyloxy)-4-(pivalyloxy)-alpha-(tert-butylaminomethyl)-benzyl alcohol hydrochloride.

EXAMPLE 74

Following a procedure similar to that described in Example 30A above, when 3-hydroxy-4-(p-toluyloxy)phenyl tert-butylaminomethyl ketone is interacted with one equivalent of sodium methoxide and the resulting sodium phenolate salt is reacted with o-toluyl chloride there is obtained 3-(o-toluyloxy)-4-(p-toluyloxy)phenyl tert-butylaminomethyl ketone which reacts with hydrochloric acid to yield the hydrochloride salt. When this hydrochloride is catalytically hydrogenated, using the procedure described above in Example 30B, there is obtained 3-(o-toluyloxy)-4-(p-toluyloxy)-alpha-(tert-butylaminomethyl) benzyl alcohol hydrochloride.

EXAMPLE 75

Following a procedure similar to that described in Example 30A above, when 3-hydroxy-4-(pivalyloxy)phenyl tert-butylaminomethyl ketone is interacted with one equivalent of sodium methoxide and the resulting sodium phenolate salt is reacted with 3,4,5-trimethoxybenzoyl chloride there is obtained 3-(3,4,5-trimethoxybenzoyloxy)-4-(pivalyloxy)phenyl tertbutylaminomethyl ketone which reacts with hydrochloric acid to yield the hydrochloride salt. When this hydrochloride is catalytically hydrogenated, using the procedure described above in Example 30B, there is obtained 3-(3,4,5-trimethoxy benzoyloxy)-4-(pivalyloxy)-alpha-(tert-butylaminomethyl)benzyl alcohol hydrochloride.

EXAMPLE 76

Following a procedure similar to that described in Example 2A above, when 3-hydroxy-4-(p-toluyloxy)phenyl tert-butylaminomethyl ketone is interacted with oen equivalent of sodium methoxide and the resulting sodium phenolate salt is reacted with isovaleryl chloride there is obtained 3-(isovaleryl oxy)-4-(p-toluyloxy)-phenyl tert-butylaminomethyl ketone which reacts with hydrochloric acid to yield the hydrochloride salt. When this hydrochloride is catalytically hydrogenated, using the procedure described above in Example 2B, there is obtained 3-(isovaleryloxy)-4-(p-toluyloxy)-alpha-(tert-butylaminomethyl) benzyl alcohol hydrochloride.

EXAMPLE 77

Following a procedure similar to that described in Example 2A above, when 3-hydroxy-4-(p-toluyloxy)-phenyl tert-butylaminomethyl ketone is interacted with one equivalent of sodium methoxide and the resulting sodium phenolate salt is interacted with 3,3-dimethylbutanecarbonyl chloride there is obtained 3-(3,3-dimethylbutanecarbonyloxy)-4 -(p-toluyloxy)phenyl tert-butylaminomethyl ketone which reacts with hydrochloric acid to yield the hydrochloride salt. When this hydrochloride is catalytically hydrogenated, using the procedure described above in Example 2B, there is obtained 3-(3,3-dimethylbutane carbonyloxy)-4-(p-toluyloxy)-alpha-(tert-butylaminomethyl)benzyl alcohol hydrochloride.

EXAMPLE 78

Following a procedure similar to that described in Example 2A above, when 3-hydroxy-4-(p-toluyloxy)-phenyl tert-butylaminomethyl ketone is interacted with one equivalent of sodium methoxide and the resulting sodium phenolate salt is reacted with docosanoyl chloride there is obtained 3-(docosanoyloxy)-4-(p-toluyloxy)phenyl tert-butylaminomethyl ketone which reacts with methanesulfonic acid to yield the methaneusalfonate salt. When this methanesulfonate is catalytically hydrogenated, using the procedure described above in Example 2B, there is obtained 3-(docosanoyloxy)-4-(p-toluyloxy)-alpha-(tert-butylaminomethyl)benzyl alcohol methanesulfonate.

EXAMPLE 79

Following a procedure similar to that described in Example 30 A above, when 3-hydroxy-4-(7,7-dimethylocatanoyloxy) phenyl tert-butylaminomethyl ketone is interacted with one equivalent of sodium methoxide and the resulting sodium phenolate salt is reacted with p-isopropoxyphenylacetyl chloride there is obtained 3-(p-isopropoxyphenylacetoxy)-4-(7,7-dimethyloctanoyloxy)phenyl tert-butylaminomethyl ketone which reacts with methanesulfonic acid to yield the methanesulfonate salt. When this methanesulfonate is catalytically hydrogenated, using the procedure described above in Example 30B, there is obtained 3-(p-isopropoxyphenylacetoxy)-4-( 7,7-dimethylocatanoyloxy)-alpha-(tert-butylaminomethyl)benzyl alcohol methanesulfonate.

EXAMPLE 80

Following a procedure similar to that described above in Example 30A, when 3-hydroxy-4-(p-toluyloxy)phenyl tert-butylaminomethyl ketone is interacted with nicotinoyl chloride, there is obtained 3-(nicotinoyloxy)-4-(p-toluyloxy)phenyl tert-butylaminomethyl ketone; and by interaction of this base with hydrochloric acid there is obtained the hydrochloride salt. When this hydrochloride is catalytically hydrogenated, using the procedure described above in Example 30B, there is obtained 3- nicotinoyloxy-4-(p-toluyloxy)-alpha-(tert-butylaminomethyl) benzyl alcohol hydrochloride.

EXAMPLE 81

Following a procedure similar to that described in Example 2A above, when 3-hydroxy-4-(nicotinoyloxy)-phenyl tert-butylaminomethyl ketone is interacted with one equivalent of sodium methoxide and the resulting sodium phenolate salt is reacted with 9-octadecenoyl chloride there is obtained 3-(9-octadecenoyloxy)-4-(nicotinoyloxy)phenyl tert-butylaminomethyl ketone which reacts with methanesulfonic acid to yield the methanesulfonate salt. When this methanesulfonate is reduced with sodium borohydride using the procedure described above in Example 30C, there is obtained 3-(9-octadecenoyloxy)-4-(nicotinoyloxy)-alpha- (tert-butylaminomethyl)benzyl alcohol methanesulfonate.

EXAMPLE 82

Following a procedure similar to that described in Example 13A above, when 3-hydroxy-4-(isovaleryloxy)phenyl tert-butylaminomethyl ketone is interacted with one equivalent of sodium methoxide and the resulting sodium phenolate salt is reacted with1,3-dimethylcyclobutanecarbonyl chloride there is obtained 3-(1,3-dimethylcyclobutanecarbonyloxy)-4-(isovaleryloxy) phenyl tert-butylaminomethyl ketone which reacts with hydrochloric acid to yield the hydrochloride salt. When this hydrochloride is catalytically hydrogenated, using the procedure described above in Example 13B, there is obtained 3-(1,3-dimethylcyclobutane carbonyloxy)-4-(isovaleryloxy)-alpha-(tert-butylaminomethyl) benzyl alcohol hydrochloride.

EXAMPLE 83

A. Under an atmosphere of nitrogen, 8.4 g of sodium methoxide is added with vigorous stirring to 16.8 g of 3,4-dihydroxyphenyl isopropylaminomethyl ketone hydrochloride suspended in 200 mL. of N, N-dimethylformamide. About 20 mL. of solvent is distilled from the reaction mixture under reduced pressure to remove methyl alchol. Then, under an atmosphere of nitrogen, 16 g. of 2,2-dimethylpentanoyl chloride is dripped in slowly at 5° C. with vigorous stirring, and stirring is continued for one hour after all of the acid chloride has been added. The solvent is distilled off under reduced pressure and the resulting residue is partitioned between water and diethyl ether. The ether layer is separated and washed with water, and the ether is distilled off to yield 3,4-bis(2,2-dimethylpentanoyloxy)phenyl isopropyl aminomethyl ketone. This product is treated with hydrochloric acid in isopropyl alcohol, and the solvent is evaporated to yield 3,4bis(2,2-dimethylpentanoyloxy)phenyl isopropylamino methyl ketone hydrochloride.

B. A solution of 3,4-bis(2,2-dimethylpentanoyloxy)-phenyl isopropylaminomethyl ketone hydrochloride in anhydrous ethyl alcohol is hydrogenated in the presence of 10 percent palladium on-charcoal hydrogenation catalyst until one mole equivalent of hydrogen has been absorbed. The hydrogenation mixture is filtered to remove the catalyst, the solvent is evaporated from the filtrate, and isopropyl acetate is added to the residue and then distilled off. The residue thus obtained is dissolved in boiling isopropyl acetate and the solution thus obtained is cooled. The precipitate which forms is collected on a filter, washed with isopropyl acetate and with diethyl ether, and dried at 70° C. There is thus obtained 3,4-bis(2,2-dimethylpentanoyloxy)-alpha-(isopropylaminomethyl)benzyl alcohol hydrochloride as a white crystalline powder.

EXAMPLE 84

When 7,7-dimethyloctanoyl chloride is substituted for the isobutyryl chloride in the procedure described in Example 2A above, the product obtained is 3,4-bis(7,7-dimethyloctanoyloxy)phenyl isopropylaminomethyl ketone; and by interaction of this base with methanesulfonic acid there is obtained the methanesulfonate salt. When this methanesulfonate is catalytically hydrogenated using the proceudre described in Example 2B above, there is obtained 3,4-bis(7,7-dimethyloctanoyloxy)-alpha-(isopropylaminomethyl)benzyl alcohol methanesulfonate.

EXAMPLE 85

When hexadecanoyl chloride is substituted for the isobutyryl chloride in the procedure described in Example 2A above, the product obtained is 3,4-bis(hexadecanoyloxy)phenyl isopropylaminomethyl ketone; and by interaction of this base with methanesulfonic acid there is obtained the methanesulfonate salt. When this methanesulfonate is catalytically hydrogenated using the procedure described in Example 2B above, there is obtained 3,4-bis(hexadecanoyloxy)-alpha-(isopropylaminomethyl) benzyl alcohol methanesulfonate.

EXAMPLE 86

When docosanoyl chloride is substituted for the isobutyryl chloride in the procedure described in Example 2A above, the product obtained is 3,4-bis(docosanoyloxy)phenyl isopropyl aminomethyl ketone; and by interaction with methanesulfonic acid there is obtained the methanesulfonate salt. When this methanesulfonate is catalytically hydrogenated using a procedure similar to that described in Example 2B above, there is obtained 3,4-bis(docosanoyloxy)-alpha-(isopropylaminomethyl)benzyl alcohol methanesulfonate.

EXAMPLE 87

Following the procedure described above in Example 2A but using 4-methylcyclohexaneactyl chloride instead of isobutyryl chloride there is obtained 3,4-bis(4-methylcyclohexaneacetoxy) phenyl isopropylaminomethyl ketone; and by interaction of this base with hydrochloric acid there is obtained the hydrochloride salt. When this hydrochloride is catalytically hydrogenated, using a procedure similar to that described above in Example 2B, there is obtained 3,4-bis(4-methylcyclohexaneacetoxy)-alpha-(isopropylaminomethyl)benzyl alcohol hydrochloride.

EXAMPLE 88

When cycloheptanecarbonyl chloride is substituted for the isobutyryl chloride in the procedure described in Example 2A above, the product obtained is 3,4-bis(cycloheptanecarbonyloxy)phenyl isopropylaminomethyl ketone; and by interaction of this base with hydrochloric acid there is obtained the hydrochloride salt. When this hydrochloride is catalytically hydrogenated using a procedure similar to that described in Example 2B above, there is obtained 3,4-bis(cycloheptanecarbonyloxy)-alpha-(isopropylaminomethyl)benzyl alcohol hydrochloride.

EXAMPLE 89

When p-toluyl chloride is substituted for the isobutyryl chloride in the procedure described in Example 2A above, the acylation product obtained is 3,4bis-(p-toluyloxy)phenyl isopropylaminomethyl ketone, m.p. 82-85° C. (uncorr.). This base was treated with trifluoroacetic acid to yield the trifluoroacetic acetate salt as a white crystalline solid which melted at 193-195° C. (uncorr.). When 24 g. of this trifluoroacetate was catalytically hydrogenated using a procedure similar to that described in Example 2B above there was obtained 19.5 g. of 3,4-bis(p-toluyloxy)-alpha-(isopropylaminomethyl)benzyl alcohol trifluoroacetate, m.p. 115-117° C. (uncorr.). A 15 g. portion of this salt was converted to the free base which was then treated with methanesulfonic acid to yield 10.5 g. of the methanesulfonate salt as a white crystalline solid which melted at 114-116° C. (uncorr.).

EXAMPLE 90

When phenylacetyl chloride is substituted for the isobutyryl chloride in the procedure described in Example 2A above, the product obtained is 3,4-bis(-phenylacetoxy)phenyl isopropylaminomethyl ketone; and by interaction of this base with hydrochloric acid there is obtained the hydrochloride salt. When this hydrochloride is catalytically hydrogenated using a procedure similar to that described in Example 2B above, there is obtained 3,4-bis(phenylacetoxy)-alpha-(isopropylaminomethyl) benzyl alcohol hydrochloride.

EXAMPLE 91

Following the procedure described above in Example 2A but using 3,7-dimethyl-3,6-octadienoyl chloride instead of isobutyryl chloride there is obtained 3,4-bis(3,7-dimethyl-3,6-octadienoyloxy)phenyl isopropylaminomethyl ketone; and by interaction of this base with methanesulfonic acid there is obtained the methanesulfonate salt. When this base is reduced with sodium borohydride, using a procedure similar to that described above in Example 30C, there is obtained 3,4bis(3,7-dimethyl 3,6-octadienoyloxy)-alpha-(isopropylaminomethyl)benzyl alcohol. By catalytically hydrogenating 3,4-bis (3,7-dimethyl-3,6-octadienoyloxy)phenyl isopropylaminomethyl ketone methanesulfonate, using a procedure similar to that described above in Example 30B, there is obtained 3,4-bis(3,7-dimethyloctadecanoyloxy)-alpha-(isopropylaminomethyl) benzyl alcohol methanesulfonate.

EXAMPLE 92

When isonicotinoyl chloride is substituted for the isobutyryl chloride in the procedure described in Example 2A above, the product obtained is 3,4-bis-(isonicotinoyloxy)phenyl isopropylaminomethyl ketone; and by interaction of this base with methanesulfonic acid there is obtained the methanesulfonate salt. When this methanesulfonate is catalytically hydrogenated using a procedure similar to that described in Example 2B above, there is obtained 3,4-bis (isonicotinoyloxy)-alpha-(isopropylaminomethyl) benzyl alcohol methanesulfonate.

EXAMPLE 93

Following the procedure described above in Example 58A but using 3,4-dihydroxyphenyl isopropylaminomethyl ketone hydrochloride instead of 3,4-dihydroxyphenyl tert-butylaminomethyl ketone hydrochloride and octanoyl chloride instead of isovaleryl chloride, there is obtained 3-hydroxy-4-(octanoyloxy)phenyl isopropylaminomethyl ketone; and by interaction of this base with hydrochloric acid there is obtained the hydrochloride salt. When this hydrochloride is catalytically hydrogenated, using a procedure similar to that described above in Example 2B, there is obtained 3-hydroxy-4-(octanoyloxy)-alpha-(isopropylaminomethyl) benzyl alcohol hydrochloride.

EXAMPLE 94

Following the procedure described above in Example 58A but using 3,4-dihydroxyphenyl isopropylaminomethyl ketone hydrochloride instead of 3,4-dihydroxyphenyl tert-butylaminomethyl ketone hydrochloride and 3,3-dimethylcyclobutanecarbonyl chloride instead of isovaleryl chloride, there is obtained 3-hydroxy-4-(3,3-dimethylcyclobutanecarbonyloxy)phenyl isopropylaminomethyl ketone; and by interaction of this base with hydrochloric acid there is obtained the hydrochloride salt. When this hydrochloride is catalytically hydrogenated, using a procedure similar to that described above in Example 2B, there is obtained 3-hydroxy-4-(3,3-dimethylcyclobutanecarbonyloxy)-alpha-(isopropylaminomethyl)benzyl alcohol hydrochloride.

EXAMPLE 95

Following the procedure described above in Example 58A but using 3,4-dihydroxyphenyl isopropylaminomethyl ketone hydrochloride instead of 3,4-dihydroxyphenyl tert-butylaminomethyl ketone hydrochloride and phenoxyacetyl chloride instead of isovaleryl chloride, there is obtained 3-hydroxy-4-(phenoxyacetoxy) phenyl isopropylaminomethyl ketone; and by interaction of this base with methanesulfonic acid there is obtained the methanesulfonate salt. When this methanesulfonate is catalytically hydrogenated, using a procedure similar to that described above in Example 2B, there is obtained 3-hydroxy-4-(phenoxyacetoxy)-alpha-(isopropylaminomethyl) benzyl alcohol methanesulfonate.

EXAMPLE 96

Following the procedure described above in Example 58A but using 3,4-dihydroxyphenyl isopropylaminomethyl ketone hydrochloride instead of 3,4-dihydroxyphenyl tert-butylaminomethyl ketone hydrochloride and 1-naphthalenecarbonyl chloride instead of isovaleryl chloride, there is obtained 3-hydroxy-4-(1-naphthalenecarbonyloxy)phenyl isopropylaminomethyl ketone; and by interaction of this base with hydrochloric acid there is obtained the hydrochloride salt. When this hydrochloride is catalytically hydrogenated, using a procedure similar to that described above in Example 2B, there is obtained 3-hydroxy-4-(1-naphthalenecarbonyloxy)-alpha-(isopropylaminomethyl)benzyl alcohol hydrochloride.

EXAMPLE 97

Following the procedure described above in Example 58A but using 3,4-dihydroxyphenyl isopropylaminomethyl ketone hydrochloride instead of 3,4-dihydroxyphenyl tert-butylaminomethyl ketone hydrochloride and p-toluyl chloride instead of isovaleryl chloride, there is obtained 3-hydroxy-4-(p-toluyloxy)phenyl isopropylaminomethyl ketone; and by interaction of this base with hydrochloric acid there is obtained the hydrochloride salt. When this hydrochloride is catalytically hydrogenated, using a procedure similar to that described above in Example 2B, there is obtained 3-hydroxy-4-(p-toluyloxy)-alpha-(isopropylaminomethyl)benzyl alcohol hydrochloride.

EXAMPLE 98

Following a procedure similar to that described above in Example 58A but using 3,4-dihydroxyphenyl isopropylaminomethyl ketone hydrochloride instead of 3,4-dihydroxyphenyl tert-butylaminomethyl ketone hydrochloride, and nicotinoyl chloride instead of isovaleryl chloride, there is obtained 3-hydroxy-4-(nicotinoyloxy)phenyl isopropylaminomethyl ketone; and by interaction of this base with hydrochloric acid there is obtained the hydrochloride salt. When this hydrochloride is catalytically hydrogenated, using a procedure similar to that described above in Example 2B, there is obtained 3-hydroxy-4-(nicotinoyloxy)-alpha-(isopropylaminomethyl) benzyl alcohol hydrochloride.

EXAMPLE 99

Following the procedure described above in Example 58A but using 3,4-dihydroxyphenyl isopropylaminomethyl ketone hydrochloride instead of 3,4-dihydroxyphenyl tert-butylaminomethyl ketone hydrochloride and 2,3,4-trimethylbenzoyl chloride instead of isovaleryl chloride, there is obtained 3-hydroxy-4-(2,3,4-trimethylbenzoyloxy)phenyl isopropylaminomethyl ketone; and by interaction of this base with hydrochloric acid there is obtained the hydrochloride salt. When this hydrochloride is catalytically hydrogenated, using a procedure similar to that described above in Example 2B, there is obtained 3-hydroxy-4-(2,3,4-trimethylbenzoyloxy)-alpha-(isopropylaminomethyl)benzyl alcohol hydrochloride.

EXAMPLE 100

Following the procedure described above in Example 58A, but using 3,4-dihydroxyphenyl isopropylaminomethyl ketone hydrochloride instead of 3,4-dihydroxyphenyl tert-butylaminomethyl ketone hydrochloride and m-dimethylaminobenzoyl chloride instead of isovaleryl chloride, there is obtained 3-hydroxy-4-(m-dimethylaminobenzoyloxy)phenyl isopropylaminomethyl ketone; and by interaction of this base with hydrochloric acid there is obtained the hydrochloride salt. When this hydrochloride is catalytically hydrogenated, using a procedure similar to that described above in Example 2B, there is obtained 3-hydroxy-4-(m-dimethylaminobenzoyloxy)-alpha-(isopropylminomethyl)benzyl alcohol hydrochloride

EXAMPLE 101

Following the procedure described above in Example 58A but using 3,4-dihydroxyphenyl isopropylaminomethyl ketone hydrochloride instead of 3,4-dihydroxyphenyl tert-butylaminomethyl ketone hydrochloride and o-propionamidobenzoyl chloride instead of isovaleryl chloride, there is obtained 3-hydroxy-4-(o-propionamidobenzoyloxy)phenyl isopropylaminomethyl ketone; and by interaction of this base with methanesulfonic acid there is obtained the methanesulfonate salt. When this methanesulfonate is catalytically hydrogenated, using a procedure similar to that described above in Example 2B, there is obtained 3-hydroxy-4-(o-propionamidobenzoyloxy)-alpha-(isopropylaminomethyl)benzyl alcohol methanesulfonate.

EXAMPLE 102

Following the procedure described above in Example 58A but using 3,4-dihydroxyphenyl isopropylaminomethyl ketone hydrochloride instead of 3,4-dihydroxyphenyl tert-butylaminomethyl ketone hydrochloride and 2-chloro-3-methoxy-4-methylbenzoyl chloride instead of isovaleryl chloride, there is obtained 3-hydroxy-4-(2-chloro-3-methoxy-4-methylbenzoyloxy)phenyl isopropylaminomethyl ketone; and by interaction of this base with hydrochloric acid there is obtained the hydrochloride salt. When this hydrochloride is catalytically hydrogenated, using a procedure similar to that described above in Example 2B, there is obtained 3-hydroxy-4-(2-chloro-3-methoxy-4-methylbenzoyloxy)-apha-(isopropylaminomethyl)benzyl alcohol hydrochloride.

EXAMPLE 103

Following the procedure described above in Example 58A but using 3,4-dihydroxyphenyl isopropylaminomethyl ketone hydrochloride instead of 3,4-dihydroxyphenyl tert-butylaminomethyl ketone hydrochloride and 10,13-octadecadienoyl chloride instead of isovaleryl chloride, there is obtained 3-hydroxy-4-(10,13-octadec a dienoyloxy)phenyl isopropylaminomethyl ketone; and by interaction of this base with methanesulfonic acid there is obtained the methanesulfonate salt. When this methanesulfonate is reduced with sodium borohydride, using a procedure similar to that described above in Example 30C, there is obtained 3-hydroxy-4-(10,13-octadecadienoyloxy)-alpha-(isopropylaminomethyl)benzyl alcohol methanesulfonate. By catalytic hydrogenation of 3-hydroxy-4-(10,13-octadienoyloxy)phenyl isopropylaminomethyl ketone methanesulfonate, using a procedure similar to that described above in Example 30B, there is obtained 3-hydroxy-4-(octadecanoyloxy)-alpha-(isopropylaminomethyl)benzyl methanesulfonate.

EXAMPLE 104

Following a procedure similar to that described above in Example 2A, when 3-hydroxy-4-(isovaleryloxy)phenyl isopropylaminomethyl ketone is interacted with one equivalent of sodium methoxide and the resulting sodium phenolate salt is reacted with 3,3-dimethylpentanoyl chloride there is obtained 3-(3,3-dimethylpentanoyloxy)-4-(isovaleryloxy)phenyl isopropylaminomethyl ketone; and by interaction of this base with hydrochloric acid there is obtained the hydrochloride salt. When this hydrochloride is catalytically hydrogenated, using a procedure similar to that described above in Example 2B, there is obtained 3-(3,3-dimethylpentanoyloxy)-4-(isovaleryloxy)-alpha-(isopropylaminomethyl)benzyl alcohol hydrochloride.

EXAMPLE 105

Following the procedure described above in Example 58A but using 3,4-dihydroxyphenyl isopropylaminomethyl ketone hydrochloride instead of 3,4-dihydroxyphenyl tert-butylaminomethyl ketone hydrochloride there is obtained 3-hydroxy-4-(isovaleryloxy)phenyl isopropylaminomethyl ketone.

Following a procedure similar to that described above in Example 2A, when 3-hydroxy-4-(isovaleryloxy)phenyl isopropylaminomethyl ketone is interacted with one equivalent of sodium methoxide and the resulting sodium phenolate salt is reacted wirh p-toluyl chloride there is obtained 3-(p-toluyloxy)-4-(isovaleryloxy)phenyl isopropylaminomethyl ketone; and by interaction of this base with hydrochloric acid there is obtained the hydrochloride salt. When this hydrochloride is catalytically hydrogenated, using a procedure similar to that described above in Example 2B, there is obtained 3-(p-toluyloxy)-4-(isovaleryloxy)-alpha-(isopropylaminomethyl)benzyl alcohol hydrochloride.

EXAMPLE 106

Following a procedure similar to that described above in Example 2A, when 3-hydroxy-4-(p-toluyloxy)phenyl isopropylaminomethyl ketone is interacted with one equivalent of sodium methoxide and the resulting sodium phenolate salt is reacted with picolinoyl chloride, there is obtained 3-(picolinoyloxy)4-(p-toluyloxy)phenyl isopropylaminomethyl ketone; and by interaction of this base with hydrochloric acid there is obtained the hydrochloride salt. When this hydrochloride is catalytically hydrogenated, using a procedure similar to that described above in Example 2B, there is obtained 3-(picolinoyloxy)-4-(p-toluyloxy)-alpha-(isopropylaminomethyl)benzyl alcohol hydrochloride.

EXAMPLE 107

Following a procedure similar to that described in Example 2A above, when 3-hydroxy-4-(2-chloro-3-methoxy-4-methylbenzoyloxy)phenyl isopropylaminomethyl ketone is interacted with one equivalent of sodium methoxide and the resulting sodium phenolate salt is reacted with isovaleryl chloride there is obtained 3-(isovaleryloxy)-4-(2-chloro-3-methoxy-4-methylbenzoyloxy)phenyl isopropylaminomethyl ketone; and by interaction of this base with hydrochloric acid there is obtained the hydrochloride salt. When this hydrochloride is catalytically hydrogenated, using a procedure similar to that described above in Example 2B, there is obtained 3-(isovaleryloxy)-4-(2-chloro-3-methoxy-4-methylbenzoyloxy)-alpha-(isopropylaminomethyl)benzyl alcohol hydrochloride.

EXAMPLE 108

Following a procedure similar to that described above in Example 2A, when 3-hydroxy-4-(phenoxyacetoxy)phenyl isopropylaminomethyl ketone is interacted with one equivalent of sodium methoxide and the resulting sodium phenolate salt is reacted with cyclohexanecarbonyl chloride there is obtained 3-(cyclohexanecarbonyloxy)-4-(phenoxyacetoxy)phenyl isopropylaminomethyl ketone; and by interaction of this base with hydrochloric acid there is obtained the hydrochloride salt. When this hydrochloride is catalytically hydrogenated, using a procedure similar to that described above in Example 2B, there is obtained 3-(cyclohexanecarbonyloxy)-4-(phenoxyacetoxy)-alpha-(isopropylaminomethyl)benzyl alcohol hydrochloride.

EXAMPLE 109

Following a procedure similar to that described above in Example 2A, when 3-hydroxy-4-(2-chloro-3-methoxy-4-methylbenzoyloxy)phenyl isopropylaminomethyl ketone is interacted with one equivalent of sodium methoxide and the resulting sodium phenolate is reacted with 3,3-dimethylheptadecanoyl chloride there is obtained 3-(3,3-dimethylheptadecanoyloxy)-4-(2-chloro-3-methoxy-4phenyl isopropylaminomethyl ketone; and by interaction of this base with hydrochloric acid there is obtained the hydrochloride salt. When this hydrochloride is catalytically hydrogenated, using a procedure similar to that described above in Example 2B, there is obtained 3-(3,3-dimethylheptadecanoyloxy)-4-(2-chloro-3-methoxy-4-methylbenzoyloxy)-alpha-(isopropylaminomethyl)benzyl alcohol hydrochloride.

EXAMPLE 110

Following a procedure similar to that described in Example 2A above when 3-hydroxy-4-(3,3-dimethylcyclobutanecarbonyloxy)phenyl isopropylaminomethyl ketone is interacted with one equivalent of sodium methoxide and the resulting sodium phenolate salt is reacted with 2,5-hexadienoyl chloride there is obtained 3-(2,5-hexadienoyloxy)-4-(3,3-dimethylcyclobutanecarbonyloxy)phenyl isopropylaminomethyl ketone which reacts with hydrochloric acid to yield the hydrochloride salt. When this hydrochloride is reduced with sodium borohydride, using a procedure similar to that described above in Example 30C, there is obtained 3-(2,5-hexadienoyloxy)-4-(3,3-dimethylcyclobutanecarbonyloxy)-alpha-(isopropylaminomethyl)benzyl alcohol hydrochloride.

EXAMPLE 111

A mixture of 13 g. of 3,4-dihydroxyphenyl tert-butylaminomethyl ketone hydrochloride, 25 m. of o-toluyl chloride, and 35 ml. of trifluoroacetic acid was heated for thirty minutes on a steam bath. The reaction mixture was concentrated under reduced pressure, and the resulting residue crystallized. This solid, which was crude 3,4-bis(o-toluyloxy)phenyl tert-butylaminomethyl ketone trifluoroacetate, was slurried in anhydrous ethyl ether and the slurry was made basic by treatment with ammonium hydroxide. The ether layer was separated and washed first with dilute aqueous sodium hydroxide solution and then with water. The ether solution was filtered and the filtrate was slurried with 4.5 g. of methanesulfonic acid in 50 ml. of isopropyl alcohol. The crystalline solid which precipitated was collected on a filter and recrystallized from 100 ml. of isopropyl alcohol and dried at 70° C. There was thus obtained 15.8 g. of 3,4-bis(o-toluyloxy)phenyl tert-butylaminomethyl ketone methanesulfonate as a white crystalline solid which melted at 134-137° C. (dec.)(uncorr.). When this methanesulfonate (15.5 g.) was catalytically hydrogenated, using a procedure similar to that described above in Example 30B, there was obtained 12.8 g. of 3,4-bis(o-toluyloxy)-alpha-(tert-butylaminomethyl)benzyl alcohol methanesulfonate as a white crystalline solid which melted at 151-153° C.(uncorr.).

EXAMPLE 112

Following a procedure similar to that described above in Example 111 but using m-toluyl chloride instead of o-toluyl chloride, there was obtained 14 g. of 3,4-bis(m-toluyloxy)phenyl tert-butylaminomethyl ketone hydrochloride as a white crystalline solid which melted at 215-218° C. When 19 g. of this hydrochloride (5 g. of which was obtained from a second run) was catalytically hydrogenated, using a procedure similar to that described above in Example 30B, there was obtained 3,4-bis(m-toluyloxy)-alpha-(tert-butylaminomethyl)benzyl alcohol hydrochloride which was converted to the free base and then to the methanesulfonate, a white crystalline solid which weighed 12.0 g. and melted at 135° C. (uncorr.).

EXAMPLE 113

Following a procedure similar to that described above in Example 111, 14 g. of 3,4-dihydroxyphenyl tert-butylaminomethyl ketone hydrochloride was reacted with 27 g. of 2,3-dimethylbenzoyl chloride in 50 ml. of trifluoroacetic acid to yield 3,4-bis(2,4-dimethylbenzoyloxy)phenyl tert-butylaminomethyl ketone trifluoroacetate. This salt was converted to the free base by treatment with sodium hydroxide solution and the free base was interacted with methanesulfonic acid to yield 22 g. of 3,4-bis(2,4-dimethylbenzoyloxy)phenyl tert-butylaminomethyl ketone methanesulfonate as a white crystalline solid which melted at 120-123° C. (dec.)(uncorr.). This salt (20 g.) was catalytically hydrogenated in N,N-dimethylformamide using a procedure similar to that described above in Example 30B, to yield 18 g. of 3,4-bis(2,4-dimethylbenzoyloxy)-alpha-(tert-butylaminomethyl)benzyl alcohol methanesulfonate as a white crystalline solid which melted at 170-172° C.(uncorr.).

EXAMPLE 114

Following a procedure similar to that described above in Example 111, 20 g. of 3,4-dihydroxyphenyl tert-butylaminomethyl ketone hydrochloride was reacted with 37 g. of 2,5-dimethylbenzoyl chloride in 50 ml. of trifluoroacetic acid to yield 3,4-bis(2,5-dimethylbenzoyloxy)phenyl tert-butylaminomethyl ketone trifluoroacetate. This salt was converted to the free base by treatment with ammonium hydroxide and the free base was interacted with methanesulfonic acid to yield 38 g. of 3,4-bis(2,5-dimethylbenzoyloxy)phenyl tert-butylaminomethyl ketone methanesulfonate as a white crystalline solid which melted at 134-137° C. (dec.)(uncorr.). This salt (37 g.) was catalytically hydrogenated in N,N-dimethylformamide, using a procedure similar to that described above in Example 30B, to yield 30 g. of 3,4-bis(2,5-dimethylbenzoyloxy)-alpha-(tert-butylaminomethyl)benzyl alcohol methanesulfonate as a white crystalline solid which melted at 156-158° C. (uncorr.).

EXAMPLE 115

Following a procedure similar to that described above in Example 111, 20 g. of 3,4-dihydroxyphenyl tert-butylaminomethyl ketone hydrochloride was reacted with 37 g. of 3,4-dimethylbenzoyl chloride in 50 ml. of trifluoroacetic acid to yield 3,4-bis(3,4-dimethylbenzoyloxy)phenyl tert-butylaminomethyl ketone trifluoroacetate. This salt was converted to the free base by treatment with ammonium hydroxide and the free base was interacted with methanesulfonic acid to yield 33 g. of 3,4-bis-(3,4-dimethylbenzoyloxy)phenyl tert-butylaminomethyl ketone methanesulfonate as a white crystalline solid which melted at 119-122° C. (uncorr.). This salt (32 g.) was catalytically hydrogenated, using a procedure similar to that described above in Example 30B, to yield 28.0 g. of 3,4-bis(3,4-dimethylbenzoyloxy)-alpha-(tert-butylaminomethyl)benzyl alcohol methanesulfonate as a white crystalline solid which melted at 212° C.

EXAMPLE 116

Following a procedure similar to that described above in Example 111, 20 g. of 3,4-dihydroxyphenyl tert-butylaminomethyl ketone hydrochloride was reacted with 37 g. of 3,5-dimethylbenzoyl chloride in 50 ml. of trifluoroacetic acid to yield 3,4-bis(3,5-dimethylbenzoyloxy)phenyl tert-butylaminomethyl ketone trifluoroacetate. This salt was converted to the free base by treatment with ammonium hydroxide and the free base was interacted with methanesulfonic acid to yield 29 g. of 3,4-bis(3,5-dimethylbenzoyloxy)phenyl tert-butylaminomethyl ketone methanesulfonate as a white crystalline solid which melted at 123–128° C. This salt (28 g.) was catalytically hydrogenated in N,N-dimethylformamide, using a procedure similar to that described above in Example 30B, to yield 25 g. of 3,4-bis(3,5-dimethylbenzoyloxy)alpha-(tert-butylaminomethyl)benzyl alcohol methanesulfonate as a white crystalline solid which melted at 190–193° C. (uncorr.).

EXAMPLE 117

A mixture of 13 g. of 3,4-dihydroxyphenyl tert-butylaminomethyl ketone hydrochloride, 26 g. of p-tolylacetyl chloride and 40 g. of trifluoroacetic acid was refluxed for one hour and then the volatile material was removed from the reaction mixture by heating under reduced pressure. The resulting residue, which was crude 3,4-bis(p-tolylacetoxy)phenyl tert-butylaminomethyl ketone trifluoroacetate, was slurried in diethyl ethyl-dilute ammonium hydroxide, after which the ether layer was separated, washed first with dilute sodium hydroxide solution and then with water, and shaken with a slight excess of dilute hydrochloric acid. The crystalline precipitate which formed was collected on a filter, washed with diethyl ether, and dried at 60° C. There was thus obtained 21 g. of 3,4-bis(p-tolylacetoxy)phenyl tert-butylaminomethyl ketone hydrochloride as a white crystalline solid which melted at 205–208° C. (dec.)(uncorr.). This salt was catalytically hydrogenated, using a procedure similar to that described above in Example 30B, to yield 16 g. of 3,4-bis(p-tolylacetoxy)-alpha-(tert-butylaminomethyl)-benzyl alcohol hydrochloride as a white crystalline solid which melted at 115–117° C. (uncorr.).

EXAMPLE 118

Following a procedure similar to that described above in Example 117, 13 g. of 3,4-dihydroxyphenyl tert-butylaminomethyl ketone hydrochloride was reacted with 20 g. of p-methoxyphenylacetyl chloride in 50 ml. of trifluoroacetic acid and the resulting product was worked up to yield 14 g. of 3,4-bis(p-methoxyphenylacetoxy)phenyl tert-butylaminomethyl ketone hydrochloride as a white crystalline solid which melted at 204–207° C. (dec.)(uncorr.). This salt (13.5 g.) was catalytically hydrogenated, using a procedure similar to that described above in Example 30B, to yield 8.8 g. of 3,4-bis(p-methoxyphenylacetoxy)-alpha-(tert-butylaminomethyl)benzyl alcohol hydrochloride as a white crystalline solid which melted at 124–127° C. (uncorr.).

EXAMPLE 119

Using a procedure similar to that described above in Example 58A, 26 g. of 3,4-dihydroxyphenyl tert-butylaminomethyl ketone hydrochloride in 300 ml. of N,N-dimethylformamide under an atmosphere of nitrogen was reacted with 16 g. of sodium methoxide and then with 14 g. of benzoyl chloride. The product was isolated as the free base, 3-hydroxy-4-(benzoyloxy)phenyl tert-butylaminomethyl ketone [20 g.; m.p. 150–165° C. (dec.) (uncorr.)], which was converted to 13 g. of its methanesulfonate, m.p. 245° C. (dec.)(uncorr.). By catalytically hydrogenating this salt, using a procedure similar to that described above in Example 30B, there is obtained 3-hydroxy-4-(benzoyloxy)-alpha-(tert-butylaminomethyl)benzyl alcohol methanesulfonate.

EXAMPLE 120

Using a procedure similar to that described above in Example 58A, 26 g. of 3,4-dihydroxyphenyl tert-butylaminomethyl ketone hydrochloride was reacted with 16 g. of sodium methoxide in N,N-dimethylformamide under an atmosphere of nitrogen and then 17 g. of p-anisoyl chloride was added to produce 35 g. of 3-hydroxy-4-(p-anisoyloxy)phenyl tert-butylaminomethyl ketone, m.p. 170–175° C. (dec.)(uncorr.), which was converted to 28 g. of the hydrochloride, m.p. 235° C. (dec.)(uncorr.). This hydrochloride (26 g.) was catalytically hydrogenated, using a procedure similar to that described above in Example 30B, to yield 19 g. of 3-hydroxy-4-(p-anisoyloxy)-alpha-(tert-butylaminomethyl)-benzyl alcohol hydrochloride as a white crystalline solid which melted at 211–213° C. (dec.)(uncorr.). By interacting this hydrochloride with p-anisoyl chloride and with acetyl chloride, there are obtained 3-hydroxy-4-(p-anisoyloxy)-alpha-(tert-butylaminomethyl)benzyl p-anisate hydrochloride and 3-hydroxy-4-(p-anisoyloxy)-alpha-(tert-butylaminomethyl)benzyl acetate hydrochloride, respectively.

EXAMPLE 121

A mixture of 20 g. of 3-hydroxy-4-(p-toluyloxy)phenyl tert-butylaminomethyl ketone methanesulfonate, 100 ml. of acetyl chloride, and 200 ml. of acetic acid was refluxed and stirred for two hours and then the volatile material was removed from the reaction mixture by heating under reduced pressure. The resulting residue was crystallized from isopropyl acetate to yield 20 g. of 3-acetoxy-4-(p-toluyloxy)phenyl tert-butylaminomethyl ketone methanesulfonate as a white crystalline solid which melted at 204–207° C. (uncorr.). This salt was catalytically hydrogenated in N,N-dimethylformamide, using a procedure similar to that described above in Example 30B, to yield 14.0 g. of 3-acetoxy-4-(p-toluyloxy)-alpha-(tert-butylaminomethyl)benzyl alcohol methanesulfonate as a white crystalline solid which melted at 171–173° C. (uncorr.).

EXAMPLE 122

A mixture of 12.5 g. of 3-hydroxy-4-(benzoyloxy)phenyl tert-butylaminomethyl ketone methanesulfonate; 13 g. of p-toluyl chloride, and 35 ml. of trifluoroacetic acid was refluxed for one hour and then the volatile material was removed from the reaction mixture under reduced pressure. The resulting solid residue was slurried in diethyl ether-water and the slurry was filtered to collect 17.1 g. of 3-(p-toluyloxy)-4-(benzoyloxy) phenyl tert-butylaminomethyl ketone methanesulfonate as a white crystalline solid which melted at 205–210° C. (dec.)(uncorr.). This salt (17 g.) was catalytically hydrogenated in N,N-dimethylformamide, using a procedure similar to that described above in Example 30B, to yield 9.3 g. of 3-(p-toluyloxy)-4-benzoyloxy-alpha-(tert-butylaminomethyl)benzyl alcohol trifluoroacetate, m.p.

162–166° C. which was converted via the free base, to 7.1 g. of the methanesulfonate, a white crystalline solid which melted at 154–156° C. (uncorr.).

EXAMPLE 123

A mixture of 18.5 g. of 3-hydroxy-4-(p-toluyloxy)-phenyl tert-butylaminomethyl ketone methanesulfonate, 12 ml. of benzoyl chloride, and 35 ml. of trifluoroacetic acid was refluxed for one hour and then the volatile material was removed from the reaction mixture by heating under reduced pressure. The residual gum, which was crude 3-benzoyloxy-4-(p-toluyloxy)phenyl tert-butylaminomethyl ketone methanesulfonate, was slurried with diethyl ether, the ether was removed by decantation, and the gum was dissolved by stirring it with diethyl ether-dilute ammonium hydroxide. The ether layer was separated, washed with dilute sodium hydroxide solution, and dried with ground cellulose fiber. The ether solution was mixed with a solution of 5 g. of methanesulfonic acid in 25 ml. of isopropyl alcohol, thereby causing precipitation of a syrup which rapidly solidified. This solid was collected and dissolved in 50 ml. of isopropyl alcohol, and the solution was diluted with diethyl ether and stirred. The crystalline solid which formed was collected on a filter, washed with a small amount of isopropyl alcohol-diethyl ether mixture, and dried. There was thus obtained 13 g. of 3-benzoyloxy-4-(p-toluyloxy)phenyl tert-butylaminomethyl ketone methanesulfonate hydrate as a white crystalline solid which softened at 115° C. (uncorr.). This salt was catalytically hydrogenated, using the procedure described above in Example 30B, to yield 8.5 g. of 3-benzoyloxy-4-(p-toluyloxy)-alpha-(tert-butylaminomethyl)benzyl alcohol methanesulfonate as a white crystalline solid which melted at 183–185° C. (uncorr.).

EXAMPLE 124

To 50 g. of N-benzyl-N-methylamine in 200 ml. of N,N-dimethylformamide there was added portionwise 37.2 g. of 3,4-dihydroxy-alpha-chloroacetophenone with occasional swirling of the mixture. The mixture was allowed to stand for thirty minutes and then was warmed to 70° C. and the N,N-dimethylformamide was distilled off. The resulting residue was slurried in 400 ml. of water and the solid product was collected on a filter and washed with water and diethyl ether. By treating the 3,4-dihydroxyphenyl N-benzyl-N-methylaminomethyl ketone thus obtained with methanesulfonic acid there was obtained 54.5 g. of the methanesulfonate salt, m.p. 154–155° C. (uncorr.). Using a procedure similar to that described above in Example 58A, 36.8 g. of this salt was reacted with 16.2 g. of sodium methoxide in N,N-dimethylformamide under an atmosphere of nitrogen and then 16 g. of p-toluyl chloride was added to produce 3-hydroxy-4-(p-toluyloxy)-phenyl N-benzyl-N-methylaminomethyl ketone, which by treatment with methanesulfonic acid was converted to 32 g. of the methanesulfonate, m.p. 214–216° C.(uncorr.). The N-benzyl group was removed from this product by catalytic hydrogenation in the presence of 2 g. of 10 percent palladium-on-charcoal catalyst until the calculated one mole equivalent of hydrogen was absorbed. There was thus obtained 20 g. of 3-hydroxy-4-(p-toluyloxy)phenyl methylaminomethyl ketone methanesulfonate, m.p. 188–189° C. (uncorr.). This salt was catalytically hydrogenated in 200 ml. of 95 percent ethyl alcohol at 25° C. in the presence of 2 g. of 10 percent palladium-on-charcoal hydrogenation catalyst until one mole equivalent of hydrogen was absorbed. This required eight hours, during the last three hours of which period the reaction mixture was heated at 50° C. There was thus obtained 12.3 g. of 3-hydroxy-4-(p-toluyloxy)-alpha-(methylaminomethyl)benzyl alcohol methanesulfonate as a white crystalline solid which melted at 185° C. (uncorr.).

EXAMPLE 125

Using a procedure similar to that described above in Example 3A, 3,4-dihydroxyphenyl N-benzyl-N-methylaminomethyl ketone methanesulfonate is reacted with two mole equivalents of 2,2-dimethylpentanoyl chloride in 2,2-dimethylpentanoic acid to yield 3,4-bis(2,2-dimethylpentanoyloxy)phenyl N-benzyl-N-methylaminomethyl ketone methanesulfonate as a white crystalline solid. This salt is debenzylated by catalytic hydrogenation in the presence of palladium-on-charcoal hydrogenation catalyst, in the same manner as the debenzylation procedure described above in Example 124, to yield 3,4-bis(2,2-dimethylpentanoyloxy)-phenyl methylaminomethyl ketone methanesulfonate as a white crystalline solid. This salt is catalytically hydrogenated in anhydrous ethyl alcohol in the presence of 10 percent palladium-on-charcoal hydrogenation catalyst until one mole equivalent of hydrogen is absorbed. There is thus obtained 3,4-bis(2,2-dimethylpentanolyoxy)-alpha-(methylaminomethyl)benzyl alcohol methanesulfonate as a white crystalline solid.

EXAMPLE 126

Following a procedure similar to that described above in Example 111, 18.5 g. of 3,4-dihydroxyphenyl N-benzyl-N-methylaminomethyl ketone methanesulfonate was reacted with 16 g. of p-toluyl chloride in 35 ml. of trifluoroacetic acid to yield 33 g. of 3,4-bis(p-toluyloxy)phenyl N-benzyl-N-methylaminomethyl ketone methanesulfonate. This salt was debenzylated by catalytic hydrogenation in the presence of palladium-on-charcoal hydrogenation catalyst, in the same manner as the debenzylation procedure described above in Example 124, to yield 21.6 g. of 3,4-bis-(p-toluyloxy)phenyl methylaminomethyl ketone methanesulfonate, m.p. 195–197° C. (uncorr.). This salt was catalytically hydrogenated, using the procedure described above in Example 30B, to yield 13.8 g. of 3,4-bis(p-toluyloxy)-alpha-(methylaminomethyl)benzyl alcohol methanesulfonate as a white crystalline solid which melted at 110–112° C. (uncorr.).

EXAMPLE 127

A. A mixture of 40 g. of 3,4-dihydroxy-alpha-chloroacetophenone, 86 g. of dibenzylamine, and 300 ml. of anhydrous isopropyl alcohol was refluxed for four hours. After adding 300 ml. of anhydrous diethyl ether, the reaction mixture was cooled, the solid (dibenzylamine hydrochloride) which precipitated was removed by filtration, and the filtrate was evaporated to dryness. The resulting residue was dissolved in 800 ml. of isopropyl acetate and this solution was washed with three 250 ml. portions of water and then dried over sodium sulfate. To the dry solution there was added 500 ml. of isopropyl alcohol and the mixture was acidified by addition of an isopropyl alcohol solution of hydrogen chloride and cooled. The solid (another portion of dibenzylamine hydrochloride) which separated was removed by filtration and the filtrate was concentrated under reduced pressure and acetone was added to the residue, which solidified. This solid was collected on a filter. There was thus obtained 54 g. of 3,4-dihydroxyphenyl N,N-dibenzylaminomethyl ketone hydrochloride which melted at 196-198° C. (uncorr.). Using a procedure similar to that described above in Example 111 this product (35 g.) was reacted with 40 g. of p-toluyl chloride in 50 ml. of trifluoroacetic acid, and the resulting ester-amine salt was converted to the free esteramine by treatment with ammonium hydroxide, and the free esteramine was treated with an isopropyl alcohol solution of hydrogen chloride to yield 38 g. of 3,4-bis(p-toluyloxy)phenyl N,N-dibenzylaminomethyl ketone hydrochloride which melted at 165-172° C. (dec.)(uncorr.).

B. To 40 g. of 3,4-bis(p-toluyloxy)phenyl N,N-dibenzylaminomethyl ketone hydrochloride in 750 ml. of anhydrous methyl alcohol stirred at 0-3° C. in an icebath there was gradually added, over a period of twenty minutes, 10 g. of sodium borohydride. The reaction mixture was stirred in an ice-bath for one hour, then was acidified by addition of 13 ml. of glacial acetic acid, and the solvent was removed by evaporation under reduced pressure. The solid residue thus obtained was taken up in a mixture of 250 ml. of water, 25 ml. of concentrated ammonium hydroxide, and 400 ml. of diethyl ether. The ether layer was separated, washed with two 60 ml. portions of water, dried over sodium sulfate, and concentrated by evaporation under reduced pressure. The oily residue thus obtained, which was crude 3,4-bis(p-toluyloxy)-alpha-(N,N-dibenzylaminomethyl)benzyl alcohol, was dissolved in 150 ml. of isopropyl alcohol and 25 ml. of an ethyl alcohol solution of hydrogen chloride. The solvent was removed by evaporation under reduced pressure and the resulting residue was stirred in 170 ml. of anhydrous isopropyl alcohol while heating on a steam bath. The crystalline solid which precipitated was collected on a filter. This product, which weighed 35 g., was dissolved in 850 ml. of boiling methyl alcohol and the solution was concentrated by evaporation under reduced pressure until the solution became cloudy (volume reduced about 200 ml.) and cooled in an ice-bath. The solid which crystallized out was collected on a filter. There was thus obtained 25 g. of 3,4-bis(p-toluyloxy)-alpha-(N,N-dibenzylaminomethyl)benzyl alcohol hydrochloride as a white crystalline solid which melted at 221-223° C. (uncorr.). This salt (24 g.) was converted to the free base by treatment with ammonium hydroxide and the free base was dissolved in 100 ml. of isopropyl alcohol and treated with 3.67 g. of methanesulfonic acid in 25 ml. of anhydrous isopropyl alcohol. The solvent was removed by evaporation under reduced pressure and the methanesulfonate thus obtained was debenzylated by catalytic hydrogenation in anhydrous ethyl alcohol in the presence of 10 percent palladium-on-charcoal hydrogenation catalyst, in the earlier stages at room temperature and then later at 50° C. After removal of the catalyst, the hydrogenation mixture was concentrated under reduced pressure to a volume of approximately 75 ml. The crystalline precipitate which formed was mixed with 100 ml. of acetone and the mixture was filtered. The solid thus collected, which weighed 18 g. and melted at 176-180° C. (uncorr.), was recrystallized from a mixture of equal parts of acetone and anhydrous ethyl alcohol to yield 16 g. of 3,4-bis(p-toluyloxy)-alpha-(aminomethyl)benzyl alcohol methanesulfonate as a white crystalline solid which melted at 178-181° C. (uncorr.).

EXAMPLE 128

A. Using a procedure similar to that described above in Example 2A, 3,4-dihydroxyphenyl N,N-dibenzylaminomethyl ketone hydrochloride is reacted with two mole equivalents of sodium methoxide and the resulting sodium phenolate product is reacted with two equivalents of 2,2-dimethylpentanoyl chloride to yield 3,4-bis(2,2-dimethylpentanoyloxy)phenyl N,N-dibenzylaminomethyl ketone hydrochloride.

B. To 3,4-bis(2,2-dimethylpentanoyloxy)phenyl N,N-dibenzylaminomethyl ketone hydrochloride in anhydrous methyl alcohol stirred at 3-7° C. there is added portionwise, over a period of thirty minutes, sodium borohydride. Stirring for a further period of one hour is continued at 3-7° C. The reaction mixture is neutralized by addition of glacial acetic acid. The mixture is then concentrated under reduced pressure to yield a solid residue which is taken up in a mixture of water, diethyl ether, and ammonium hydroxide and filtered. The ether layer in the filtrate is separated, washed with water, dried over sodium sulfate, and evaporated under reduced pressure. The residue thus obtained is dissolved in isopropyl alcohol, an isopropyl alcohol solution of hydrogen chloride is added, and the solution is cooled. The solid which separates from solution is collected on a filter, washed with acetone and with diethyl ether, and dried at 60° C. There is thus obtained 3,4-bis(2,2-dimethylpentanoyloxy)-alpha-(N,N-dibenzylaminomethyl)benzyl alcohol hydrochloride as a white crystalline solid. This hydrochloride is converted to the free base by treatment with ammonium hydroxide, and the free base is treated with methanesulfonic acid to produce the methanesulfonate. This salt is debenzylated by catalytic hydrogenation in anhydrous ethyl alcohol in the presence of 10 percent palladium-on-charcoal hydrogenation catalyst to yield 3,4-bis(2,2-dimethylpentanoyloxy)-alpha-(aminomethyl)benzyl alcohol methanesulfonate.

EXAMPLE 129

Using a procedure similar to that described above in Example 111, 9 g. of 3,4-dihydroxyphenyl 1-(tert-butylamino)ethyl ketone hydrochloride was reacted with 16 ml. of p-toluyl chloride in 25 ml. of trifluoroacetic acid and the resulting product was worked up to yield 11 g. of 3,4-bis(p-toluyloxy)phenyl 1-(tert-butylamino)ethyl ketone hydrochloride as a white crystalline solid which melted at 225-228° C. (dec.) (uncorr.). This salt was catalytically hydrogenated, using a procedure similar to that described above in Example 30B, to yield 6.1 g. of 3,4-bis-(p-toluyloxy)-alpha-[1-(tert-butylamino)ethyl]benzyl alcohol hydrochloride as a white crystalline solid which melted at 228° C. (uncorr.).

EXAMPLE 130

A. A mixture of 50 g. of 3,4-bis(benzyloxy)-alpha-bromopropiophenone [m.p. 92-93.5° C. (uncorr.); obtained by brominating 3,4-bis(benzyloxy)propiophenone with bromine in methylene chloride], 50 ml. of tert-butylamine, 250 ml. of N,N-dimethylformamide was allowed to stand at room temperature for twenty-four hours. The mixture was then poured into 1500 ml. of water. The solid which precipitated, which was 3,4-bis(benzyloxy)phenyl 1-(tert-butylamino)ethyl ketone, was converted to 50 g. of the hydrochloride, m.p. 157-159° C. (uncorr.). This salt was catalytically hydrogenated in 250 ml. of 95 percent ethyl alcohol in the presence of 2 g. of 10 percent palladium-on-charcoal hydrogenation catalyst until the theoretical quantity of hydrogen required for removal of the two benzyl groups was absorbed. This reduction required approximately one-half hour. The resulting product, which was 3,4-dihydroxyphenyl 1-(tert-butylamino)ethyl ketone hydrochloride, after slurrying in isopropyl acetate, was a white crystalline solid which weighed 28 g. and melted at 237–239° C. (dec.) (uncorr.).

B. A 10 g. portion of 3,4-dihydroxyphenyl 1-(tert-butylamino)ethyl ketone hydrochloride was catalytically hydrogenated in 200 ml. of 95 percent ethyl alcohol in the presence of 10 percent palladium-on-charcoal hydrogenation catalyst until one mole equivalent of hydrogen was absorbed. This required eight hours, with heating during the last three hours. By removal of the catalyst and isolation of the reduction product there was obtained 6 g. of 3,4-dihydroxy-alpha-[1-tert-butylamino)ethyl]-benzyl alcohol hydrochloride as a white crystalline solid which melted at 216° C. (uncorr.).

C. A mixture of 13.5 g. of 3,4-dihydroxyphenyl 1-(tertbutylamino)ethyl ketone hydrochloride, 18 g. of isovaleryl chloride, and 50 ml. of trifluoroacetic acid was refluxed for one hour and then the volatile material was evaporated from the reaction mixture under reduced pressure. The resulting residue was slurried in diethyl ether-dilute ammonium hydroxide. The ether layer was separated, washed first with dilute sodium hydroxide solution and then with water, and evaporated to yield a residue which was taken up in 50 ml. of isopropyl alcohol and 4 ml. of concentrated hydrochloric acid. The resulting solution was evaporated under reduced pressure and the residue thus obtained was crystallized from isopropyl acetate to yield 13 g. of 3,4-bis(isovaleryloxy)phenyl 1-(tert-butylamino)ethyl ketone hydrochloride as a white crystalline solid which melted at 181–183° C. (uncorr.). This salt was catalytically hydrogenated, using a procedure similar to that described above in Example 30B, to yield 10 g. of 3,4-bis(isovaleryloxy)-alpha-[1-(tert-butylamino)ethyl]benzyl alcohol hydrochloride as a white crystalline solid which melted at 152° C. (uncorr.).

EXAMPLE 131

Using a procedure similar to that described above in Example 111, 13 g. of 3,4-dihydroxyphenyl 1-(isopropylamino)-ethyl ketone hydrochloride [m.p. 141–143° C.(uncorr.); obtained by interacting 3,4-dibenzyloxy-alpha-bromopropriophenone with isopropylamine and debenzylating the resulting 3,4-bis(benzyloxy)phenyl 1-(isopropylamino)ethyl ketone hydrochloride, m.p. 215–218° C.(uncorr.), by catalytic hydrogenation in the presence of palladium-on-charcoal] was interacted with 17 g. of p-toluyl chloride in 40 ml. of trifluoroacetic acid, and the resulting ester-amine salt was converted to the free ester-amine by treatment with ammonium hydroxide and the free ester-amine was then treated with hydrochloric acid to yield 14 g. of 3,4-bis(p-toluyloxy)phenyl 1-(isopropylamino)ethyl ketone hydrochloride as a white crystalline solid which melted at 223–235° C.(dec.) (uncorr.). This salt was catalytically hydrogenated, using a procedure similar to that described above in Example 30B, to yield 12.5 g. of 3,4-bis(p-toluyloxy)-alpha-[1-isopropylamino)-ethyl]-benzyl alcohol hydrochloride as a white crystalline solid which melted at 228–230° C. (dec.) (uncorr.).

EXAMPLE 132

Using a procedure similar to that described above in Example 111, 15 g. of 3,4-dihydroxyphenyl 1-(isopropylamino)-propyl ketone hydrochloride was reacted with 25 ml. of p-toluyl chloride in 40 ml. of trifluoroacetic acid, and the resulting ester-amine salt was converted to the free ester-amine by treatment with ammonium hydroxide and the free ester-amine was then treated with hydrochloric acid to yield 19.5 g. of 3,4-bis(p-toluyloxy)phenyl 1-(isopropylamino)propyl ketone hydrochloride as a white crystalline solid which melted at 204–207° C.(dec.) (uncorr.). This salt was catalytically hydrogenated, using the procedure described above in 18.5 30B, to yield 14 g. of 3,4-bis(p-toluyloxy)-alpha-[1-(isopropylamino)propyl]benzyl alcohol hydrochloride as a white crystalline solid which melted at 203–205° C.(uncorr.).

EXAMPLE 133

Using a procedure similar to that described above in Example 111, 15 g. of 3,4-dihydroxyphenyl 1-(cyclopentylamino)-propyl ketone hydrochloride [m.p. 108–112° C.(uncorr.); obtained by interacting 3,4-bis(-benzyloxy)phenyl-alpha-bromobutyrophenone with cyclopentylamine and debenzylating the resulting 3,4-bis(benzyloxy)phenyl 1-(cyclopentylamino)propyl ketone, m.p. 150° C. (uncorr.), by catalytic hydrogenation in the presence of palladium-on-charcoal] was reacted with 25 ml. of p-toluyl cloride in 35 ml. of trifluoroacetic acid, and the resulting ester-amine salt was converted to the free ester-amine by treatment with ammonium hydroxide and the free ester-amine was then treated with hydrochloric acid to yield 18.9 g. of 3,4-bis(p-toluyloxy)-phenyl 1-(cyclopentylamino)propyl ketone hydrochloride as a white crystalline solid which melted at 198–201° C.(uncorr.). This salt (18.5 g.) was catalytically hydrogenated, using the procedure described above in Example 30B, to yield 14.4 g. of 3,4-bis(p-toluyloxy)-alpha-[1-(cyclopentylamino)propyl]-benzyl alcohol hydrochloride as a white crystalline solid which melted at 180° C.(uncorr.).

EXAMPLE 134

To 5.3 g. of 3,4-bis(p-toluyloxy)-alpha-(tert-butylaminomethyl)benzyl alcohol methanesulfonate in 25 ml. of glacial acetic acid there was added 2.1 ml. of acetyl chloride, and the resulting mixture was shaken until complete solution was obtained. This solution was concentrated to yield a solid which was recrystallized from isopropyl acetate. There was thus obtained the methanesulfonate of 3,4-bis(p-toluyloxy)-alpha-(tert-butylaminomethyl)benzyl acetate methanesulfonate as a white crystalline solid which weighed 1.2 g. and melted at 153–155° C.(uncorr.).

EXAMPLE 135

A. A mixture of 130 g. of 3-chloromethyl-4-hydroxyacetophenone, 650 ml. of acetic anhydride, and 130 ml. of acetyl chloride was refluxed for three hours and then the reaction mixture was concentrated and fractionally distilled under reduced pressure. The fraction distilling at 135–148° C. at 0.6 mm. Hg. pressure solidified. This product, which weighed 94.9 g., was 3-chloromethyl-4-acetoxyacetophenone.

B. To 200 g. of pivalic acid there was added 17.1 g. of sodium methoxide in methyl alcohol and resulting reaction mixture was stripped of methyl alcohol under reduced pressure. To the solid residue thus obtained there was added 71.4 g. of 3-chloromethyl-4-acetoxyacetophenone and the mixture was heated with stirring while allowing 110 ml. of material to distill off. The reaction mixture was concentrated under reduced pressure and cooled, and a mixture of water and diethyl ether was added. All except about 10 g. of gummy material dissolved. The ether layer was separated and washed three times with cold aqueous sodium bicarbonate solution and once with water. The ether solution was then dried over anhydrous magnesium sulfate, concentrated, and distilled under reduced pressure. After a 4.1 g. forerun which was discarded, there was obtained 44.9 g. of a fraction which distilled at 158–168° C. at 0.1 mm. Hg. pressure. This product was slightly impure 3-(pivalyloxymethyl)-4-(pivalyloxy)acetophenone.

C. To 43 g. of 3-(pivalyloxymethyl)-4-(pivalyloxy)acetophenone in 225 ml. of chloroform there was gradually added, over a period of thirty minutes, a solution of bromine in 40 ml. of chloroform. During this addition the temperature of the reaction mixture was maintained at 10° C. by the addition thereto of solid carbon dioxide. The chloroform solution of the reaction mixture was washed twice with water, twice with dilute aqueous sodium bicarbonate solution, and finally once with water, dried over magnesium sulfate, and concentrated under reduced pressure. The resulting residue, which was 21.5 g. of crude 3-(pivalyloxymethyl)-4-(pivalyloxy)-alpha-bromoacetophenone, was added with stirring to a solution of 9.45 ml. of tert-butylamine and 13.1 g. of triethylamine in 225 ml. of dimethyl sulfoxide. During this addition the reaction mixture was stirred at 10–15° C. and thereafter was stirred at 20° C. for one-half hour. The mixture was poured into water and extracted several times with diethyl ether. The ether extracts were combined, dried, and concentraated. The gummy residue thus obtained, which was crude 3-(pivalyloxymethyl)-4-(pivalyloxy)phenyl tert-butylaminomethyl ketone, was treated with 8.5 g. of methanesulfonic acid to yield 19.5 g. of 3-(pivalyloxymethyl)-4-(pivalyloxy)phenyl tert-butylaminomethyl ketone methanesulfonate as a white crystalline solid which melted at 164–173° C.(uncorr.).

D. To a solution of 2.5 g. of 3-(pivalyloxymethyl)-4-(pivalyloxy)phenyl tert-butylaminomethyl ketone methanesulfonate in 30 ml. of methyl alcohol at −10° C. there was added portionwise 0.3 g. of sodium borohydride. The reaction mixture was then stirred for ten minutes at −10° C. and glacial acetic acid was gradually added until the mixture was neutral. The mixture was then concentrated on a rotary evaporator and the resulting residue was dissolved in 25 ml. of cold water. This solution was made slightly basic by addition of ammonium hydroxide and extracted three times with diethyl ether. The ether extracts were combined, dried over anhydrous calcium sulfate, and concentrated under reduced pressure. The resulting gummy residue was dissolved in 20 ml. of isopropyl acetate and to this solution were added 0.35 ml. of methanesulfonic acid and one volume of diethyl ether. The white precipitate which formed was collected on a filter. This product [1.4 g., m.p. 200–203° C. (uncorr)] was recrystallized from isopropyl acetate to yield 1.3 g. of 3-(pivalyloxymethyl)-4-(pivalyloxy)-alpha-(tert-butylaminomethyl)benzyl alcohol methanesulfonate as a white crystalline solid which melted at 200–203° C.(uncorr.).

EXAMPLE 136

A. To 180 g. of isovaleric acid there was added 19 g. of sodium methoxide in methyl alcohol. Methyl alcohol and methyl isovalerate were removed from the resulting reaction mixture by evaporation under reduced pressure on a steam bath. To the residue thus obtained there was added 68.0 g. of 3-chloromethyl-4-acetoxyacetophenone, and the mixture was heated while allowing acetic acid formed in the reaction to distill off. The reaction mixture was concentrated on a rotary evaporator under reduced pressure. The resulting residue was slurried in diethyl ether and the ether layer was separated and washed three times with dilute aqueous sodium bicarbonate solution and once with water, dried over magnesium sulfate, and concentrated under reduced pressure. The residue was fractionally distilled under reduced pressure to yield 62 g. of 3-(isovaleryloxymethyl)-3-(isovaleryloxy)acetophenone as a fraction distilling at 158–168° C. at 0.08–0.1 mm. Hg. pressure.

B. To 33.4 g. of 3-(isovaleryloxymethyl)-4-(isovaleryloxy)acetophenone in 200 ml. of chloroform there was added dropwise with stirring 5.2 ml. of bromine at 0° C. The reaction mixture was washed with dilute aqueous sodium bicarbonate solution, dried over magnesium sulfate, and concentrated. The residue thus obtained, which contained 3-(isovaleryloxymethyl)-4-(isovaleryloxy)-alpha-bromoacetophenone, was added with cooling to a solution of 7.3 g. of tert-butylamine and 10.1 g. of triethylamine in 150 ml. of dimethyl sulfoxide. This reaction mixture was stirred at 15° C. for thirty minutes and then was poured into ice-water and extracted with diethyl ether. The ether extract was washed once with water, dried over anhydrous calcium sulfate, and concentrated. The residue, which was crude 3-(isovaleryloxymethyl)-4-(isovaleryloxy)phenyl tert-butylaminomethyl ketone, was reacted with methanesulfonic acid to yield 5.0 g. of 3-(isovaleryloxymethyl)-4-(isovaleryloxy)-phenyl tert-butylaminomethyl ketone methanesulfonate as a crystalline solid which melted at 190–215° C.(uncorr.).

C. To a solution of 5.0 g. of 3-(isovaleryloxymethyl)-4-(isovaleryloxy)phenyl tert-butylaminomethyl ketone methanesulfonate in 60 ml. of methyl alcohol at −10° C. there was added portionwise 0.6 g. of sodium borohydride. The reaction mixture was stirred for fifteen minutes at −5 to −10° C. and then was neutralized by addition of acetic acid, and concentrated on a rotary evaporator. This residue thus obtained was dissolved in 50 ml. of cold water and the solution was made slightly basic by addition of ammonium hydroxide and thereafter was extracted three times with diethyl ether. The ether extracts were combined, dried over anhydrous calcium sulfate, and concentrated. The resulting gummy residue, which was crude 3-(isovaleryloxymethyl)-4-(isovaleryloxy)-alpha-(tert-butylaminomethyl)benzyl alcohol, was converted to 3.5 g. of 3-(isovaleryloxymethyl)-4-(isovaleryloxy)-alpha-(tert-butylaminomethyl)benzyl alcohol methanesulfonate as a white crystalline solid which melted at 125–126° C.(uncorr.).

EXAMPLE 137

By interaction of 3-hydroxymethyl-4-hydroxyphenyl tert-butylaminomethyl ketone hydrochloride with two equivalents of p-toluyl chloride in trifluoroacetic acid there is obtained 3-(p-toluyloxymethyl)-4-(p-toluyloxy)-phenyl tert-butylaminomethyl ketone trifluoroacetate.

Conversion of this salt to the free base and reacting the latter with methanesulfonic acid yields the corresponding methanesulfonate salt which by reduction with sodium borohydride in anhydrous methyl alcohol is converted to 3-(p-toluyloxymethyl)-4-(p-toluyloxy)-alpha-(tert-butylaminomethyl)benzyl alcohol methanesulfonate. Esterification of this alcohol by treatment with pivalyl chloride yields the methanesulfonate of 3-(p-toluyloxymethyl)-4-(p-toluyloxy)-alpha-(tert-butylaminomethyl)benzyl pivalate.

EXAMPLE 138

Using a procedure similar to that described above in Example 2A, 22.5 g. of 3,4-dihydroxyphenyl 1-(cyclopentylamino)propyl ketone hydrochloride was reacted under an atmosphere of nitrogen with 13 g. of sodium methoxide, the resulting sodium phenolate salt was reacted with 20 g. of isovaleryl chloride, the ester-amine salt thus obtained was converted to the esteramine by treatment with ammonium hydroxide, and the free esteramine was then treated with hydrochloric acid to yield 19.8 g. of 3,4-bis(isovaleryloxy)phenyl 1-(cyclopentylamino)propyl ketone hydrochloride as a white crystalline solid which melted at 182°–184° C.(uncorr.). This salt (19 g.) was catalytically hydrogenated, using the procedure described above in Example 30B, to yield 16.3 g. of 3,4-bis(isovaleryloxy)-alpha-[1-(cyclopentylamino)propyl]benzyl alcohol hydrochloride as a white crystalline solid, m.p. 150° C. (uncorr.).

EXAMPLE 139

Using a procedure similar to that described above in Example 58A, 13 g. of 3,4-dihydroxyphenyl tert-butylaminomethyl ketone hydrochloride was reacted with 8 g. of sodium methoxide in 200 ml. of N,N-dimethylformamide under an atmosphere of nitrogen and then 8 g. of m-toluyl chloride was added to produce 3-hydroxy-4-(m-toluyloxy)phenyl tert-butylaminomethyl ketone hydrochloride. This salt was converted to the free base which was treated with acetic acid to yield 11.5 g. of the acetate salt, m.p. 170°–175° C. By treating a slurry of this salt in 100 ml of N,N-dimethylformamide with 40 g. of methanesulfonic acid there was obtained 10.6 g. of the corresponding methanesulfonate salt, m.p. >250° C.(uncorr.). This methanesulfonate (10 g.) was catalytically hydrogenated, using a procedure similar to that described above in Example 30B, to yield 5.4 g. of 3-hydroxy-4-(m-toluyloxy)-alpha-(tert-butylaminomethyl)benzyl alcohol methanesulfonate as a white crystalline solid which melted at 165°–168° C.(uncorr.).

EXAMPLE 140

By interacting 13 g. of 3,4-dihydroxyphenyl tert-butylaminomethyl ketone hydrochloride with 8.0 g. of 2,2-dimethylpentanoyl chloride in 30 ml. of trifluoroacetic acid on a steam bath for one hour and treating the resulting product with ammonium hydroxide there was obtained 3-hydroxy-4-(2,2-dimethylpentanoyloxy)phenyl tert-butylaminomethyl ketone. This product was converted to the acetate salt (10.5 g.) and this salt was converted to the corresponding methanesulfonate salt [8.3 g., m.p. 250° C.(dec.)(uncorr.)], by treatment with a slight excess of methanesulfonic acid. When this methanesulfonate (8.0 g.) was catalytically hydrogenated in the presence of palladium-on-charcoal catalyst, there was obtained 5.8 g. of 3-hydroxy-4-(2,2-dimethylpentanoyloxy)-alpha-(tert-butylaminomethyl)benzyl alcohol methanesulfonate as a white crystalline solid which melted at 128°–130° C.(uncorr.).

EXAMPLE 141

3,4-Dihydroxyphenyl 1-(tert-butylamino)ethyl ketone hydrochloride (8 g.) was reacted with 18 ml. of pivalyl chloride in 35 ml. of trifluoroacetic acid, the resulting ester-amine salt was converted to the ester-amine, and the ester-amine was treated with hydrochloric acid to yield 10.5 g. of 3,4-bis(pivalyloxy)phenyl 1-(tert-butylamino)ethyl ketone hydrochloride, m.p. 200°–202° C. (uncorr.). This ketone was catalytically hydrogenated in the presence of palladium-on-charcoal catalyst to yield 3,4-bis(pivalyloxy)-alpha-[1-(tert-butylamino)ethyl]benzyl alcohol hydrochloride as a white crystalline solid which melted at 205°–207° C. (uncorr.).

EXAMPLE 142

Using a procedure similar to that described above in Example 58A, 26 g. of 3,4-dihydroxyphenyl tert-butylaminomethyl ketone hydrochloride was reacted with 16 g. of sodium methoxide in 300 ml. of N,N-dimethylformamide under an atmosphere of nitrogen and then 17 g. of p-anisoyl chloride was added to produce 3-hydroxy-4-(p-anisoyloxy)phenyl tert-butylaminomethyl ketone hydrochloride. This salt was converted to the free base which was treated with acetic acid to yield 35 g. of the acetate salt, m.p. 170°–175° C.(dec.)(uncorr.). By treating this salt in N,N-dimethylformamide with concentrated hydrochloric acid there was obtained 28 g. of the hydrochloride salt, m.p. >235° C.(dec.)(uncorr.). When this hydrochloride is catalytically hydrogenated, using a procedure similar to that described above in Example 30B, there is obtained 3-hydroxy-4-(p-anisoyloxy)-alpha-(tert-butylaminomethyl)benzyl alcohol hydrochloride.

EXAMPLE 143

By interaction of 22 g. of 3-hydroxy-4-(p-anisoyloxy)phenyl tert-butylaminomethyl ketone hydrochloride with 20 ml. of benzoyl chloride in 50 ml. of trifluoroacetic acid and treatment of the acylation product with ammonium hydroxide and then with hydrochloric acid there was obtained 14.3 g. of 3-benzoyloxy-4-(p-anisoyloxy)phenyl tert-butylaminomethyl ketone hydrochloride, m.p. 212°–215° C.(uncorr.). Catalytic hydrogenation of this ketone (14.0 g.) in N,N-dimethylformamide in the presence of palladium-on-charcoal catalyst yielded 3-benzoyloxy-4-(p-anisoyloxy)-alpha-(tert-butylaminomethyl)benzyl alcohol hydrochloride which was converted to 6.3 g. of the corresponding methanesulfonate salt as a white crystalline solid, m.p. 173°–175° C.(uncorr.).

EXAMPLE 144

By interacting 20 g. of 3,4-dihydroxyphenyl 1-(tert-butylamino)propyl ketone hydrochloride with 25 ml. of p-toluyl chloride in 50 ml. of trifluoroacetic acid and treating the acylation product with ammonium hydroxide and then with hydrochloric acid there was obtained 31 g. of 3,4-bis-(p-toluyloxy)phenyl 1-(tert-butylamino)propyl ketone hydrochloride, m.p. 115°–120° C.(dec.)(uncorr.). Catalytic hydrogenation of this ketone (30 g.) in N,N-dimethylformamide in the presence of palladium-on-charcoal catalyst yielded 20 g. of crude product, m.p. 115°–118° C.(dec.)(uncorr.), which was recrystallized from 100 ml. of isopropyl alcohol to yield 12.5 g. of 3,4-bis-(p-toluyloxy)-alpha-[1-(tert-butylamino)propyl]benzyl alcohol hydrochloride as a white crystalline solid which melted at 228°-230° C.(uncorr.).

EXAMPLE 145

3-Hydroxy-4-(p-anisoyloxy)phenyl tert-butylaminomethyl ketone hydrochloride (15 g.) was reacted with 11 g. of p-anisoyl chloride in 50 ml. of trifluoroacetic acid, the resulting esteramine salt was converted to the ester-amine, and the esteramine was then treated with methanesulfonic acid to yield 9.7 g. of 3-hydroxy-4-(p-anisoyloxy)phenyl tert-butylaminomethyl ketone methanesulfonate, m.p. >250° C.(uncorr.). This product (9.7 g.) was suspended in a mixture of 100 ml. of acetic acid and 50 ml. of acetyl chloride and heated under reflux for one hour, and from the resulting reaction mixture there was obtained 10.7 g. of 3-acetoxy-4-(p-anisoyloxy)phenyl tert-butylaminomethyl ketone methanesulfonate, m.p. 150°-152° C. (uncorr.). This ketone (10.3 g.) was catalytically hydrogenated in N,N-dimethylformamide in the presence of palladium-on-charcoal catalyst to yield 9.1 g. of 3-acetoxy-4-(p-anisoyloxy)-alpha-(tert-butylaminomethyl)benzyl alcohol methanesulfonate as a white crystalline solid which melted at 172°-174° C.(uncorr.).

EXAMPLE 146

By interaction of 16.2 g. of 3,4-dihydroxyphenyl tert-butylaminomethyl ketone hydrochloride with 5.2 ml. of acetyl chloride in 140 ml. of trifluoroacetic acid there was obtained 3-hydroxy-4-acetoxyphenyl tert-butylaminomethyl ketone hydrochloride. Without isolation, this product was treated with 21 ml. of p-toluyl chloride to yield 8.0 g. of 3-(p-toluyloxy)-4-acetoxyphenyl tert-butylaminomethyl ketone hydrochloride, m.p. 244°-246° C.(dec.)(uncorr.). Using a procedure similar to that described above in Example 30C, this ketone (7.9 g.) was reduced in anhydrous methyl alcohol with 750 mg. of sodium borohydride and the resulting product was treated with methanesulfonic acid to yield 5.8 g. of 3-(p-toluyloxy)-4-acetoxy-alpha-(tert-butylaminomethyl)benzyl alcohol methanesulfonate as a white crystalline solid which melted at 184°-186° C.(uncorr.).

EXAMPLE 147

By interaction of 20 g. of 3,4-dihydroxyphenyl tert-butylaminomethyl ketone hydrochloride with 8 ml. of acetyl chloride in 150 ml. of trifluoroacetic acid there was obtained 3-hydroxy-4-acetoxyphenyl tert-butylaminomethyl ketone hydrochloride. Without isolation, this product was reacted with 15 ml. of o-toluyl chloride to yield 23 g. of 3-(o-toluyloxy)-4-acetoxyphenyl tert-butylaminomethyl ketone hydrochloride, m.p. 236°-237° C.(dec.)(uncorr.). This ketone (20.0 g.) was reduced in anhydrous methyl alcohol with 1.35 g. of sodium borohydride and the product was treated with methanesulfonic acid to yield 8.9 g. of 3-(o-toluyloxy)-4-acetoxy-alpha-(tert-butylaminomethyl)benzyl alcohol methanesulfonate as a white crystalline solid which melted at 190°-192° C. (uncorr.).

EXAMPLE 148

To a stirred solution of 20.0 g. of 3,4-dihydroxyphenyl tert-butylaminomethyl ketone hydrochloride in 140 ml. of trifluoroacetic acid there was gradually added, over a two and one-half hour period, 7.5 ml. of acetyl chloride. Stirring was continued for a further period of two hours, 19.0 g. of 1-adamantanecarbonyl chloride was then added in a single portion, and the reaction mixture was stirred for two and one-half hours at room temperature and finally one-half hour at 40° C. The reaction product was isolated and treated with methanesulfonic acid to yield 19.2 g. of 3-(1-adamantanecarbonyloxy)-4-acetoxyphenyl tert-butylaminomethyl ketone methanesulfonate as a white crystalline solid. This ketone (18.5 g.) was catalytically hydrogenated in N,N-dimethylformamide in the presence of palladium-on-charcoal catalyst to yield 7.4 g. of 3-(1-adamantanecarbonyloxy)-4-acetoxy-alpha-(tert-butylaminomethyl)benzyl alcohol methanesulfonate as a white crystalline solid which melted at 203°-204° C.(uncorr.).

EXAMPLE 149

By interaction of 3,4-dihydroxyphenyl tert-butylaminomethyl ketone hydrochloride with 7.5 ml. of acetyl chloride in 150 ml. of trifluoroacetic acid there was obtained 3-hydroxy-4-acetoxyphenyl tert-butylaminomethyl ketone hydrochloride. Without isolation, this product was reacted with 15 ml. of p-anisoyl chloride and the acylation product was treated with methanesulfonic acid to yield 19.8 g. of 3-(p-anisoyloxy)-4-acetoxyphenyl tert-butylaminomethyl ketone methanesulfonate as a white crystalline solid. [The corresponding hydrochloride melted at 235°-237° C.(uncorr.)]. This product(19.5 g.) was catalytically hydrogenated in N,N-dimethylformamide in the presence of palladium-on-charcoal catalyst to yield 7.2 g. of 3-(p-anisoyloxy)-4-acetoxy-alpha-(tert-butylaminomethyl)benzyl alcohol methanesulfonate as a white solid which melted at 181°-182° C.(dec.)(uncorr.).

EXAMPLE 150

A. To a solution of 3-(acetoxymethyl)-4-acetoxyacetophenone in 150 ml. of N,N-dimethylformamide there was added, while stirring at room temperature, 14.0 g. of trans-2-phenylcyclopropylamine. (In another run, benzylamine was substituted for the trans-2-phenylcyclopropylamine with equivalent results). After stirring the reaction mixture for two hours it was partitioned between ethyl acetate and water and the desired 3-(acetoxymethyl)-4-hydroxyacetophenone was isolated in crude form from ethyl acetate solution as a pale yellow oil which weighed 38 g. [When purified, this compound was a white crystalline solid, m.p. 108°-109° C. (uncorr.)]. This oil was dissolved in a mixture of 100 ml. of diethyl ether and 100 ml. of benzene and while stirring the solution 15 ml. of triethylamine was added followed by dropwise addition of 19.2 g. of p-toluyl chloride. The resulting reaction mixture was stirred at room temperature over night and then by extraction with diethyl ether and purification there was obtained 20.2 g. of 3-acetoxymethyl-4-(p-toluyloxy)acetophenone as a white crystalline solid, m.p. 85°-89° C. (uncorr.). This product (20 g.) was dissolved in 180 ml. of chloroform, and a trace of hydrobromic acid was added followed by addition, at 5° C. with stirring, of a solution of 10.0 g. of bromine in 40 ml. of chloroform. Cold aqueous sodium bicarbonate solution was added to the reaction mixture, and the chloroform layer was separated, dried, and evaporated under reduced pressure to yield a pale yellow oil which crystallized. This solid was washed with cold diethyl ether. The off-white solid thus obtained, which weighed 23.8 g., was 3-acetoxymethyl-4-(p-toluyloxy)-alpha-bromoacetophenone, m.p. 75°–77° C.(uncorr.). A solution of 11.8 g. of this product in 30 ml. of N,N-dimethylformamide was added dropwise over a period of forty minutes to a stirred solution of 9.5 g. of tert-butylamine in 100 ml. of N,N-dimethylformamide at −50° C. The reaction mixture was stirred for twenty minutes, allowed to warm to 0° C., and diluted with 400 ml. of diethyl ether, and the reaction product was partitioned between diethyl ether and water. The resulting ether extract was dried, ethanolic hydrogen chloride was added, and the mixture was cooled. The solid which separated from solution was collected on a filter. There was thus obtained 10.0 g. of 3-acetoxymethyl-4-(p-toluyloxy)phenyl tert-butylaminomethyl ketone hydrochloride as a white crystalline solid which melted at 235°–245° C.(dec.)(uncorr.).

B. To 15.2 g. of 3-acetoxymethyl-4-(p-toluyloxy)phenyl tert-butylaminomethyl ketone hydrochloride in 150 ml. of anhydrous methyl alcohol, cooled to 0° C., there was added 700 mg. of sodium borohydride. After ten minutes, several drops of acetic acid were added to neutralize the reaction solution which was then evaporated to dryness. The reaction product was extracted into a mixture of diethyl ether and methylene dichloride and from this extract there was recovered 7.5 g. of 3-acetoxymethyl-4-(p-toluyloxy)-alpha-(tert-butylaminomethyl)benzyl alcohol methanesulfonate as a white crystalline solid which melted at 163°–165° C.(uncorr.).

EXAMPLE 151

A. Proceeding in a manner similar to that described above in part A of Example 150: 40 g. of 3-(acetoxymethyl)-4-hydroxyacetophenone was reacted with 21 g. of p-anisoyl chloride in methylene chloride in the presence of 18 ml. of triethylamine to yield 33.6 g. of 3-(acetoxymethyl)-4-(p-anisoyloxy)acetophenone as a white crystalline solid; this product (33 g.) was brominated in chloroform by treatment with 16 g. of bromine to yield 34.8 g. of 3-(acetoxymethyl)-4-(p-anisoyloxy)-alpha-bromoacetophenone as a white crystalline solid, m.p. 90°–91° C. (uncorr.); and reaction of this bromo ketone (17.8 g.) with 20 ml. of tert-butylamine in N,N-dimethylformamide at −55° C. yielded 3-(acetoxymethyl)-4-(p-anisoyloxy)phenyl tert-butylaminomethyl ketone which was treated with ethanolic hydrogen chloride to yield 30.2 g. of 3-(acetoxymethyl)-4-(p-anisoyloxy)phenyl tert-butylaminomethyl ketone hydrochloride as a white crystalline solid which melted at 220°–228° C.(dec.)(uncorr.).

B. To a slurry of 29.9 g. of 3-(acetoxymethyl)-4-(p-anisoyloxy)phenyl tert-butylaminomethyl ketone hydrochloride in 200 ml. of anhydrous methyl alcohol at 0° C. there was added, portionwise over a period of fifteen minutes, 1.25 g. of sodium borohydride. Then after ten minutes, a few ml. of acetic acid were added and the reaction mixture was evaporated to dryness. The reaction product was extracted into methylene chloride and from this extract there was recovered 3-(acetoxymethyl)-4-(p-anisoyloxy)-alpha-(tert-butylaminomethyl)benzyl alcohol which was converted to 15.3 g. of its methanesulfonate salt, a white crystalline solid which melted at 181°–182° C.(uncorr.).

EXAMPLE 152

A. Proceeding in a manner similar to that described above in Example 150: 15.0 g. of 3-(acetoxymethyl)-4-hydroxyacetophenone was reacted with 14.3 g. of 1-adamantanecarbonyl chloride in methylene chloride in the presence of 10.5 g. of triethylamine to yield 30.0 g. of crude 3-(acetoxymethyl)-4-(1-adamantanecarbonyloxy)acetophenone as a nearly colorless oil; this product (26 g.) was brominated in chloroform by treatment with 11.2 g. of bromine to yield 34 g. of crude 3-(acetoxymethyl)-4-(1-adamantanecarbonyloxy)-alpha-bromoacetophenone; and this bromo ketone (30 g.) was reacted with 33 ml. of tert-butylamine in N,N-dimethylformamide at −60° C. to yield 20.0 g. of 3-(acetoxymethyl)-4-(1-adamantanecarbonyloxy)phenyl tert-butylaminomethyl ketone hydrochloride as a white crystalline solid, m.p. 240–241° C.(dec.) (uncorr.).

B. Using a procedure similar to that described above in part B of Example 151, 20 g. of 3-(acetoxymethyl)-4-(1-adamantanecarbonyloxy)phenyl tert-butylaminomethyl ketone hydrochloride was reduced in anhydrous methyl alcohol with 1.0 g. of sodium borohydride and the reduction product was treated with methanesulfonic acid to yield 9.3 g. of 3-(acetoxymethyl)-4-(1-adamantanecarbonyloxy)-alpha-(tert-butylaminomethyl)benzyl alcohol methanesulfonate as a white crystalline solid which melted at 183–185° C.(dec.) (uncorr.).

EXAMPLE 153

A. Proceeding in a manner similar to that described above in Example 150: 15.0 g. of 3-(acetoxymethyl)-4-hydroxyacetophenone was reacted with o-toluyl chloride in methylene chloride in the presence of 10.5 ml. of triethylamine to yield 24 g. of 3-(acetoxymethyl)-4-(m-toluyloxy)acetophenone as a white crystalline solid; this product (23 g.) was brominated in chloroform by treatment with 11.2 g of bromine to yield 30 g. of 3-(acetoxmethoxy)-4-(m-toluyloxy)-alpha-bromoacetophenone as a pale yellow oil; and this bromo ketone (28 g.) was reacted with 33 ml. of triethylamine in N,N-dimethylformamide to yield 3-(acetoxymethyl)-4-(o-toluyloxy)phenyl tert-butylaminomethyl ketone, m.p. 235–242° C.(dec.)(uncorr.), which was treated with ethanolic hydrogen chloride to yield 22 g. of 3-(acetoxymethyl)-4-(o-toluyloxy)phenyl tert-butylaminomethyl ketone hydrochloride as a white crystalline solid.

B. Proceeding in a manner similar to that described above in part B of Example 151, 22 g. of 3-(acetoxymethyl)-4-(o-toluyloxy)phenyl tert-butylaminomethyl ketone hydrochloride was reduced in anhydrous methyl alcohol with 1.13 g. of sodium borohydride and the reduction product was treated with methanesulfonic acid to yield 3-(acetoxymethyl)-4-(o-toluyloxy)-alpha-(tert-butylaminomethyl)benzyl alcohol methanesulfonate as a white solid which melted at 116–118° C.(uncorr.).

EXAMPLE 154

When 3-(pivalyloxymethyl)-4-(pivalyloxy)acetophenone is selectively de-acylated at the 4-position by treatment with benzylamine by the procedure described above in part A of Example 150, there is produced 3-(pivalyloxymethyl)-4-hydroxyacetophenone. By treating this product with one equivalent of sodium methoxide and reacting the resulting sodium phenolate with m-toluyl chloride, using a procedure similar to that described above in Example 2A, there is obtained 3-(pivalyloxymethyl)-4-(m-toluyloxy)acetophenone. Using a procedure similar to that described above in Example 135C, bromination of this product yields 3-(pivalyloxymethyl)-4-(m-toluyloxy)-alphabromoacetophenone which reacts with tert-butylamine to yield 3-(pivalyloxymethyl)-4-(m-toluyloxy)phenyl tert-butylaminomethyl ketone. Conversion of this ester-ketone to the methanesulfonate and catalytic hydrogenation in the presence of palladium-on-charcoal hydrogenation catalyst yields 3-(pivalyloxymethyl)-4-(m-toluyloxy)alpha-(tert-butylaminomethyl)benzyl alcohol methanesulfonate. Reaction of this compound with p-toluyl chloride yields the methanesulfonate of 3-(pivalyloxymethyl)-4-(m-toluyloxy)-alpha-(tert-butylaminomethyl)benzyl p-toluate. Treatment of this product with benzylamine in N,N-dimethylformamide at room temperature for several hours yields 3-(pivalyloxymethyl)-4-hydroxy-alpha-(tert-butylaminomethyl)-benzyl p-toluate.

EXAMPLE 155

By reacting 3-hydroxymethyl-4-hydroxyacetophenone [m.p. 124–125° C.(uncorr.); obtained by hydrolysis of the corresponding diacetate, 3-(acetoxymethyl)-4-acetoxyacetophenone, with dilute aqueous hydrochloric acid] with two molecular equivalents of p-toluyl chloride in trifluoroacetic acid there is produced 3-(p-toluyloxymethyl)-4-(p-toluyloxy)-acetophenone. Proceeding as described above in Example 154, but using as the starting material 3-(p-toluyloxymethyl)-4-(p-toluyloxy)acetophenone instead of 3-(pivalyloxymethyl)-4-(pivalyloxy)acetophenone, there are obtained successively the products:

3-(p-toluyloxymethyl)-4-hydroxyacetophenone;
3-(p-toluyloxymethyl)-4-(m-toluyloxy)acetophenone;
3-(p-toluyloxymethyl)-4-(m-toluyloxy)-alpha-bromoacetophenone;
3-(p-toluyloxymethyl)-4-(m-toluyloxy)phenyl tert-butylaminomethyl ketone and its methanesulfonate;
3-(p-toluyloxymethyl)-4-(m-toluyloxy)-alpha-(tert-butylaminomethyl)benzyl alcohol methanesulfonate;
the methanesulfonate of 3-(p-toluyloxymethyl)-4-(m-toluyloxy)-alpha-(tert-butylaminomethyl)-benzyl p-toluate; and
3-(p-toluyloxymethyl)-4-hydroxy-alpha-(tert-butylaminomethyl)benzyl p-toluate.

EXAMPLE 156

By interacting 28 g. of 3,4-dihydroxyphenyl 1-(tert-butylaminomethyl)propyl ketone hydrochloride with 33 ml. of benzoyl chloride in 80 ml. of trifluoroacetic acid and treating the acylation product with ammonium hydroxide and then with hydrochloric acid there was obtained 19.0 g. of 3,4-bis(benzoyloxy)phenyl 1-(tert-butylamino)propyl ketone hydrochloride, m.p. 205–207° C. This ketone was reduced in anhydrous methanol with 1.4 g. of sodium borohydride and the product was treated with methanesulfonic acid to give 18 g. of 3,4-bis(benzoyloxy)-alpha-[(tert-butylamino)propyl]benzyl alcohol methanesulfonate, m.p. 214–216° C.

EXAMPLE 157

A solution containing 16.8 g. of 3,4-bis-(p-toluyloxy)-alpha-(tert-butylaminomethyl)benzyl alcohol methanesulfonate and 9.3 ml. of p-toluyl chloride in 60 ml. of trifluoroacetic acid was stirred 3 hours at room temperature. The reaction mixture was then evaporated to dryness under reduced pressure below 40° C. and the residue was partitioned between ether and dilute aqueous sodium hydroxide. The ethereal layer was separated, washed with water and saturated aqueous sodium chloride, dried over anhydrous magnesium sulfate and evaporated to dryness under reduced pressure below 35° C. The residue was dissolved in isopropyl acetate; the resulting solution acidified with 1.8 ml. of methanesulfonic acid and evaporated to dryness under reduced pressure. The residue was crystallized from isopropyl acetate to give after drying 8.85 g. of 3,4-bis-(p-toluyloxy)-alpha-(tert-butylaminomethyl)benzyl p-toluate methanesulfonate, m.p. 212–214° C.

EXAMPLE 158

To a vigorously stirred mixture containing 98.5 g. of 3',4'-bis-p-toluyloxypropionphenone (m.p. 107–108° C., prepared by acylating 3',4'-dihydroxypropiophenone with p-toluyl chloride in pyridine), 735 g. 1,2-dichloroethane and 35 g. of ethyl acetate under nitrogen there was added over 0.5 hr. at 28–30° C. a mixture containing 40 g. of bromine and 86 g. of 1,2-dichloroethane. The reaction mixture was washed successively with water, 5% aqueous sodium bicarbonate and water, dried over anhydrous sodium sulfate and evaporated to dryness under reduced pressure to give 117 g. of 2-bromo-3',4'-bis-(p-toluyloxy)-propiophenone, m.p. 138–140° C. This product (111 g., 0.231 mole) was treated with 91 g. (0.462 mole) of dibenzylamine in 600 ml. of absolute ethanol and heated under reflux for approximately 2.5 days. The precipitated dibenzyl ammonium bromide was removed by filtration and the filtrate was evaporated to dryness under reduced pressure. The residue was taken up in ether and the resulting solution acidified with ethereal hydrogen chloride to give a gum which upon trituration with fresh ether afforded a semi-solid. Crystallization from 2propanol afforded 51 g. of 3',4'-bis-(p-toluyloxy)-2-(N,N-dibenzylamino) propiophenone hydrochloride, m.p. 197–199° C. This ketone in 600 ml. of N,N-dimethylformamide was hydrogenated in the presence of 5 g. of 10% palladium-on-charcoal catalyst at 60–65° C. The catalyst was removed by filtration and the filtrate evaporated to dryness under reduced pressure. The residue was dissolved in water; the resulting solution made alkaline with 35% aqueous sodium hydroxide and extracted with ether. The ethereal extracts were washed with water and saturated aqueous sodium chloride, dried over anhydrous sodium sulfate, and evaporated to dryness. Recrystallization from ethyl acetate afforded 23.5 g. of 3,4-bis-(p-toluyloxy)-alpha-(1-aminoethyl)benzyl alcohol m.p. 102–104° C. This product was combined with 5.5 g. obtained in another run, dissolved in 150 ml. of acetonitrile and the resulting solution acidified with 4.35 ml. of methanesulfonic acid. The precipitated acid addition salt was collected and recrystallized from ethanol to give 24.0 g. of 3,4-bis-(p-toluyloxy)-alpha-(1aminoethyl)-benzyl alcohol methanesulfonate, m.p. 223–226° C.

The following are further illustrative examples of the esters of Formulas I and II which are obtained in accordance with the hereinabove described procedures:

3,4-bis(isovaleryloxy)-alpha-(tert-butylaminomethyl)benzyl pivalate; 3-(pivalyloxy)-4-(p-toluyloxy)-alpha-(tert-butylamino-methyl)benzyl isovalerate; 3,4-bis(2-methylbutanoyloxy)-alpha-(tert-butylaminomethyl)benzyl cyclopropanecarboxylate; 3,4-bis(octadecanoyloxy)-alpha-(tert-butylaminomethyl)benzyl 3,6-octadienoate; 3-hydroxy-4-(m-toluyloxy)-alpha-(tert-butylaminomethyl)benzyl phenoxyacetate; 3-hydroxy-4-(p-anisoyloxy) alpha-(tert-butylaminomethyl)benzyl nicotinate; 3,4-bis(p-toluyloxy)-alpha-(isopropylaminomethyl)benzyl propionate; 3,4-bis(2,4-dimethylbenzoyloxy)-alpha-(methylaminomethyl)benzyl 2-naphthalenecarboxylate; 3,4-bis(p-toluyloxy)-alpha-(aminomethyl)benzyl cyclohexaneacetate; 3,4-bis(p-toluyloxy)-alpha-[1-(isopropylamino)-2-methylpropyl]benzyl p-acetamidophenyl acetate; 3,4-bis(isovaleryloxy)-alpha-[1-(tert-butylamino) butyl]benzyl stearate; 3,4-bis(m-chlorobenzoyloxy)-alpha-[1-(cyclopropylamino)propyl]benzyl p-trifluoromethylbenzoate; 3-hydroxy-4-(decanoyloxy)-alpha-[1-(cyclohexylamino)ethyl] benzyl 2,3,5-trifluorobenzoate; 3-hydroxy-4-(2,5-hexadienoyloxy)-alpha-[1-(tert-butylamino)-2-methylpropyl]benzyl alcohol; 3,4-bis(p-toluyloxy)-alpha-[1-(cyclohexylamino)butyl]benzyl alcohol; 3-(p-toluyloxymethyl)-4-(pivalyloxy)-alpha-(tert-butylaminomethyl)benzyl alcohol; 3-(p-toluyloxymethyl)-4-hydroxy-alpha-(tert-butylaminomethyl)-benzyl alcohol; 3-(p-toluyloxymethyl)-4-(m-toluyloxy)-alpha-[1-(tert-butylamino)ethyl]benzyl alcohol; 3-(isonicotinoyloxymethyl)-4-(crotonoyloxy)-alpha-tert-butylaminomethyl)benzyl alcohol; 3-(cyclobutanecarbonyloxymethyl)-4-(phenoxyacetoxy)-alpha-(aminomethyl)benxyl alcohol; 3-(o-toluyloxymethyl)-4-(benzoyloxy)-alpha-(1-aminoethyl)benzyl alcohol; 3-(p-toluyloxymethyl)-4-(p-toluyloxy)-alpha-(cyclopropylaminomethyl)benzyl alcohol; 3-(dodecanoyloxymethyl)-4-(p-diethylaminobenzoyloxy)-alpha-(1-aminopropyl)benzyl alcohol; 3-(p-bromobenzoyloxymethyl)-4-(cyclopentanecarbonyloxy)-alpha-(isopropylaminomethyl)benzyl alcohol; 3-(benzoyloxymethyl)-4-(cyclobutaneacetoxy)-alpha-[1-(ethylamino)ethyl]benzyl alcohol; 3-(phenoxyacetoxymethyl)-4-hydroxy-alpha-(tert-butylaminomethyl)-benzyl alcohol; 3-(3-phenylpropionyloxymethyl)-4-hydroxy-alpha-[1-(tert-butylamino)-2-methylpropyl]benzyl alcohol; 3-(m-chlorobenzoyloxymethyl)-4-(pivalyloxy)-alpha-(cyclopropylaminomethyl) benzyl alcohol; 3-(3,4-dimethylbenzoyloxymethyl)-4-(3,4-dimethylbenzoyloxy)-alpha-(cyclohexylaminomethyl)benzyl alcohol; 3-(3,4,5-trimethoxybenzoyloxymethyl)-4-(acetoxy)-alpha-[1-(cyclopentylamino)propyl]benzyl alcohol; 3-(2-bromo-4-methoxybenzoyloxymethyl)- 4-(cyclohexylacetoxy)-alpha-[1-(tert-butylamino)butyl]benzyl alcohol; 3-(1-naphthalenecarbonyloxymethyl)-4-hydroxy-alpha-(ethylaminomethyl)benzyl phenylacetate; 3-(p-anisoyloxymethyl)-4-(2,2-dimethylpentanoyloxy)-alpha-(isopropylaminomethyl)benzyl acetate; 3-(p-toluyloxymethyl)-4-(p-toluyloxy)-alpha-(tert-butylaminomethyl)benzyl stearate; 3-(phenoxyacetoxymethyl)-4-(cyclopentanecarbonyloxy)-alpha-[1-(tert-butylamino) propyl]benzyl 2-methylcyclopropanecarboxylate; 3-(2,4-dimethylbenzoyloxymethyl)-4-(3,4-dimethylbenzoyloxy)-alpha-(aminomethyl)-benzyl 2,5-hexadienoate; 3-(3,3-dimethylbutanoyloxymethyl)-4-(cycloheptanecarbonyloxy)-alpha-[1-(methylamino)ethyl]benzyl m-toluate, 3-(2-adamantanecarbonyloxy)-4-(1-adamantanecarbonyloxy)-alpha-(tert-butylaminomethyl)benzyl alcohol; 3-(1-adamantanecarbonyloxy)-4-(p-toluyloxy)-alpha-(tert-butylaminomethyl)benzyl alcohol; 3-pivalyoxy-4-(p-anisoyloxy)-alpha-(tert-butylaminomethyl)benzyl alcohol; 3-benzoyloxymethyl-4-(2-adamantanecarbonyloxy)-alpha-(tert-butylaminomethyl)benzyl alcohol; 3-(1-adamantanecarbonyloxymethyl)-4-m-toluyloxy)-[alpha-(1-tert-butylamino)ethyl]benzyl alcohol; 3-cyclohexanecarbonylox-4-(1-adamantanecarbonyloxy)-alpha-[1-(isopropylamino)propyl]benzyl alcohol; 3-cyclobutanecarbonyloxymethyl-4-(trifluoromethylbenzoyloxy)-alpha-(1-aminoethyl)benzyl -adamantanecarbonyloxy)-alpha-(tert-butylaminomethyl)benzyl alcohol; 3,4-bis(p-toluyloxy)-alpha-(butylaminomethyl)benzyl alcohol; 3,4-bis(p-anisoyloxy)-alpha-(propylaminomethyl)benzyl alcohol; 3,4-bis(3,4-diethoxybenzoyloxy)-alpha-(aminomethyl)benzyl alcohol; 3-(p-tolyloxy)-4-(p-anisoyloxy)-alpha-(cyclobutylaminomethyl)benzyl alcohol; 3-(p-acetamidobenzoyloxy)-4-(1-adamantanecarbonyloxy)-alpha-(isobutylaminomethyl)benzyl alcohol; 3-nicotinoyloxymethyl-4-pivalyloxy-alpha-(tert-butylaminomethyl)benzyl alcohol; 3-(3,3-dimethylbutanecarbonyloxymethyl)-4-(p-toluyloxy)-alpha-(methylaminomethyl)benzyl alcohol, 3-benzolyloxymethyl-4-benzolyloxy-alpha-(tert-butylaminomethyl)benzyl alcohol; and 3-pivalyloxy-4-(2-naphthalenecarbonyloxy)-alpha-(tert-butylaminomethyl)benzyl alcohol.

The esters of Formula I and Formula II prepared in accordance with this invention have been demonstrated to have useful sympathomimetic activity of long duration; and the hereinabove-indicated preferred species are further desirably characterized by a low cardiovascular stimulating effect, as can be seen from the results described below. The reference compounds referred to in these results are identified as follows:

I. 3,4-Dihydroxy-alpha-(tert-butylaminomethyl)benzyl alcohol
II. 3,4-Dihydroxy-alpha-(isopropylaminomethyl)benzyl alcohol
III. 3-Hydroxymethyl-4-hydroxy-alpha-(tert-butylaminomethyl)benzyl alcohol
IV. 3,4-Dihydroxy-alpha-[1-(isopropylamino)propyl]benzyl alcohol
V. 3,4-Dihydroxy-alpha-(methylaminomethyl)benzyl alcohol Bronchodilator activity was tested in anesthetized dogs (Test Method I) and in vitro on the perfused guinea pig lung (Test Method II), using the following pharmacological test procedures:

Test Method I

Male and female dogs weighting 9–18 kg. each were anesthetized with pentobarbital sodium (30 mg/kg. i.v.). Each animal, with thorax opened at the mid-sternum, was maintained under artificial ventilation using a constant volume pump (250 ml./stroke; ten to twelve strokes per minute) attached to the tracheal cannula. The flow of air was controlled by a glass or plastic valve which closed and opened respectively on inflow and outflow of the air to and from the tracheal cannula. Bronochoconstriction and/or bronchodilatation were measured from changes in the basal airway pressure reflected by a transducer attached to the sidearm of the cannula relayed to a polygraph.

Control bronchoconstrictions were induced by intravenous injections of carbachol (choline chloride carbamate) in doses ranging from 4 to 6 micrograms per kilogram or histamine diphosphate in doses ranging from 35 to 45 micrograms per kilogram. In the majority of test animals, the above doses of constrictor agents produced a 100–200 per cent increase in the normal airway pressure or amplitude.

Solutions of the test compounds were prepared in distilled water or in saline (for infusion). Addition of a stabilizing agent, ethylenediaminetetraacetic acid, to the solutions of the reference compounds, I, II, IV, and V was required to stabilize them. These solutions were then tested for bronchodilator activity in three ways, viz. (1) by mixing a graded dose of test compound with the constant dose of carbachol or histamine in a syringe and injecting the mixture into the femoral vein of the dog, (2) by producing the bronchoconstriction first and injecting the test compound at the time of maximum constriction, and (3) by injecting the test compound first followed by carbachol or histamine in 1–10 minutes. Injections were repeated at 20–30 minutes. Bronchodilator values were obtained by measuring the areas under the response polygraph tracings (the first five minute period) of carbachol or histamine controls and of the experimentals using a planimeter. Decrease in the area thus measured was expressed as a percent bronchodilatation in reference to the area of control carbachol or histamine constriction. The mean bronchodilatations (the reductions in constrictions) were plotted against the doses administered and the mean effective dose ($ED_{50}$) was estimated in micrograms/kilogram from the dose-response curves. Blood pressure recording was taken from the femoral artery using an arterial transducer relayed to a polygraph.

In intratracheal studies, an animal preparation identical with that described above was used. A modified "aerosol actuator" was attached between the valve and the tracheal cannula and the aerosol medication was delivered directly into the tracheal passage during the inflow of air. Commencing five minutes after medication, the degree and duration of bronchodilator effect was tested at intervals of 30–60 minutes until a full or near-full recovery (a degree of constriction approaching the premedication control) was observed.

In intraduodenal studies, in the dog prepared for bronchodilation measurements, the duodenal segment of the small intestine was made easily accessible through a small mid-line incision in the abdomen. The test solution was injected into the duodenum using a fine needle. Commencing five minutes after medication, the degree and duration of bronchodilation were tested by injecting a control dose of carbachol or histamine at intervals of 30–60 minutes until the recovery or near-recovery was apparent. In some dogs showing an early recovery, a reference drug was also tested in the same dog 1.5–2 hours after the first medicine.

Representative results which were obtained in the anesthetized dog are set forth below.

| Cpd. of Ex. No. | No. of Dogs | Dose mcg/kg | Intravenous Activity Bronchodilatation in Percent Minutes After Medication | | | | | | | |
|---|---|---|---|---|---|---|---|---|---|---|
| | | | 5 | 30 | 60 | 120 | 180 | 240 | 270 | 300 |
| 30 | 3 | 70 | 54 | 63 | 61 | 52 | | 37 | | |
| | 3 | 140 | 65 | 76 | 69 | 55 | 62 | | 42 | |
| | 3 | 280 | 83 | 88 | 75 | 72 | 64 | 50 | | |
| 4 | 1 | 5.5 | 2 min. 48 | 5 | 0 | | | | | |
| 15 | 1 | 1.2 | 2 min. 20 | 27 | 8 | 0 | | | | |
| | 1 | 3.0 | 36 | | 31 | 26 | 20 | | | |
| 13 | 1 | 2.8 | 2 min. 52 | 48 | 0 | | | | | |
| | 1 | 5.6 | 69 | 34 | 10 | | | | | |
| 7 | 3–4 | 28.5 | 28 | 32 | 24 | 24 | 22 | 23 | | |
| | 3–4 | 114 | 52 | 42 | 33 | 25 | 19 | | | |
| | 3–4 | 228 | 98 | 77 | 68 | 56 | 50 | 44 | | |
| 5 | 2 | 2.8 | 14 | | | | | | | |
| | 6 | 5.6 | 53 | 27 | 26 | | | | | |
| | 2 | 11.2 | 57 | 30 | 4 | | | | | |
| | 1 | 22.4 | | 81 | 62 | 62 | 15 | 0 | | |
| | 1 | 112.0 | 100 | 92 | 59 | 13 | | | | |
| 3 | 4–8 | 0.55 | 1–2 min. 32 | | | | | | | |
| | 4–8 | 1.1 | 54 | | | | | | | |
| | 4–8 | 2.2 | 74 | | | | | | | |
| 111 | | 9.5 | 1–2 min. | 8 | 15 | | | | | |
| | | 9.5 | 0 | 0 | 0 | | | | | |
| | | 47.5 | 0 | 0 | 0 | | | | | |
| | | 47.5 | 35 | 18 | 22 | | | | | |
| | | 47.5 | 12 | 0 | 0 | 0 | | | | |
| | | 95 | 34 | 36 | 39 | 32 | 48 | 41 | | 50 |
| | | 95 | 45 | 23 | 0 | | | | | |
| | | 190 | 27 | 11 | 18 | 31 | | | | |
| | | 190 | 38 | 41 | 25 | 38 | 35 | 41 | | 25 |
| | | 380 | 33 | 53 | 38 | 55 | 38 | 33 | | |
| | | 380 | 44 | 50 | 63 | 56 | 50 | 10 | | |
| 118 | 4 | 14 | 68 | 61 | 35 | 7 | | | | |
| | 4 | 56 | 100 | 60 | 45 | 12 | | | | |
| 156 | 1 | 25 | 57 | 13 | 0 | 0 | | | | |
| | 1 | 50 | 67 | 52 | 28 | 24 | | | | |
| | 1 | 200 | 76 | 32 | 41 | 24 | | | | |
| 126 | | 147 | 1–2 min. | 27 | 15 | | | | | |
| | | 294 | 13 | 8 | 17 | | | | | |
| | | 1176 | 100 | 47 | 20 | | | | | |
| 132 | | 76 | 0 | 12 | 0 | 0 | | | | |
| | | 76 | 12 | 0 | | | | | | |
| | | 76 | 38 | 21 | 4 | 5 | | | | |
| | | 152 | 67 | — | 71 | 52 | 43 | 0 | | 0 |
| | | 152 | 66 | 75 | 62 | | | | | |
| | | 152 | 80 | 67 | 64 | | | | | |
| | | 304 | 100 | 67 | 34 | 8 | 0 | 0 | | 0 |
| | | 304 | 100 | 69 | 60 | 51 | 23 | 14 | | |
| 134 | | 75 | 25 | 21 | 5 | 0 | 0 | | | |
| | | 150 | 54 | — | 52 | 35 | 20 | 0 | | |

-continued

|  |  |  |  |  |  |  |  |  |  |
|---|---|---|---|---|---|---|---|---|---|
|  |  | 150 | 61 | 58 | 36 | 28 |  |  |  |
|  |  | 300 | — | 30 | 22 | 0 | 0 |  |  |
|  |  | 300 | 47 | 49 | 37 | 16 | 0 |  |  |
|  |  | 300 | 59 | 79 | 70 | 54 | 46 | 36 |  |
| 135 | 3 | 5 | 18 | 32 | 36 | 26 |  |  |  |
|  | 3 | 20 | 30 | 49 | 50 | 56 | 50 | 45 | 36 |
|  | 3 | 80 | 38 | 64 | 62 | 66 | 62 | 56 | 49 |
| 136 |  | 5 | 0 | 0 | 47 | 29 |  |  |  |
|  |  | 5 | 49 | 63 | 63 | 59 | 53 | 46 | 46 |
|  | 1 | 20 | 36 | 53 | 57 | 40 | 12 | 7 | 12 |
|  | 1 | 100 | 82 | 80 | 70 | 60 | 42 |  | 32 |
| 112 | 3 | 68 | 38 | 43 | 27 |  |  |  |  |
|  | 2 | 137 | 80 | 60 | 50 | 37 | 8 |  |  |
|  | 2 | 274 | 80 | 74 | 57 | 54 | 33 | 38 | 25 |
| 138 | 1 | 30 | 38 | 0 |  |  |  |  |  |
|  | 1 | 240 | 49 | 62 | 42 | 46 |  |  |  |
| 139 | 1 | 25 | 81 | 22 | 24 | 0 |  |  |  |
|  | 1 | 100 | 74 | 63 | 22 | 25 | 9 |  | 10 |
| 145 | 7 | 5 | 65 | 30 | 24 | 22 |  |  |  |
|  | 4 | 20 | 87 | 45 | 35 | 27 |  |  |  |
|  | 4 | 40 | 98 | 70 | 68 | 42 | 38 | 24 |  |
| 146 | 1 | 1.2 | 31 | 38 | 44 | — | 20 | 20 |  |
|  | 1 | 6.0 | 66 | 57 | 63 |  |  |  |  |
| 147 | 2 | 1.2 | 36 | 3 | 0 |  |  |  |  |
|  | 1 | 6.0 | 77 | 9 | 0 |  |  |  |  |
|  | 1 | 25.0 | 100 | 32 | 12 | 4 |  |  |  |
| 157 | 1 | 1000 | 30 | 33 | 44 | 41 | 34 |  |  |
|  | 1 | 1000 | 13 | 40 | 38 | 38 | 35 | 31 | 35 |
|  | 1 | 5000 | 20 | 24 | 47 | 41 | 25 |  | 27 |
| 148 | 1 | 1.3 | 21 | 1 | 10 | 16 |  |  |  |
|  | 3 | 6.5 | 47 | 30 | 23 | 15 | 13 |  |  |
|  | 3 | 32.5 | 95 | 66 | 54 | 39 | 28 | 14 |  |
| 149 | 1 | 0.5 | 54 | 19 | 19 |  |  |  |  |
|  | 1 | 6.0 | 100 | 32 | 24 |  |  |  |  |
| 150 | 3 | 8 | 42 | 37 | 44 | 44 | 32 | 20 |  |
|  | 3 | 32 | 64 | 66 | 54 | 40 | 30 | 0 |  |
|  | 1 | 128 | 85 | 87 | 67 | 60 | 52 | 24 |  |
| 151 | 1 | 8 | 43 | 33 | 50 | 43 | 30 |  | 20 |
|  | 3 | 32 | 54 | 46 | 41 | 54 | 21 | 18 |  |
|  | 3 | 128 | 85 | 81 | 81 | 73 | 69 | 64 | 52 |
| 152 | 1 | 8 | 44 | 39 | 50 | 33 | 39 | 0 |  |
|  | 1 | 32 | 77 | 78 | 75 | 70 | 63 | 52 | 45 |
|  | 1 | 128 | 97 | 92 | 93 | 87 | 89 | 88 | 82 |

| | | | 1-2 min. | | | | | | |
|---|---|---|---|---|---|---|---|---|---|
| Ref. Cpd. I | 4-8 | 0.17 | 22 | | | | | | |
| | 4-8 | 0.35 | 57 | | | | | | |
| | | | 1-2 min. | | | | | | |
| Ref. Cpd. II | 4-8 | 0.3 | 23 | | | | | | |
| | 4-8 | 0.6 | 35 | | | | | | |
| | 4-8 | 1.2 | 55 | | | | | | |
| Ref. Cpd. III | 3 | 0.25 | 18 | 0 | | | | | |
| | 3 | 1 | 31 | 14 | 3 | | | | |
| | 5 | 4 | 65 | 24 | 18 | 0 | | | |
| Ref. Cpd. IV | 1 | 2 | 32 | 0 | | | | | |
| | 3 | 4 | 72 | 31 | 19 | | | | |
| | 2 | 8 | 74 | 13 | 13 | | | | |

| Cpd. of Ex. No. | Dose mcg/kg | 1-2 | 10 | 30 | | | Minutes | | |
|---|---|---|---|---|---|---|---|---|---|
| Ref. Cpd. V | 4 | 0 | 0 | | | | | | |
| | 8 | 36 | 0 | | | | | | |
| | 8 | 33 | | 0 | | | | | |
| | 8 | 0 | 0 | | | | | | |
| | 16 | 69 | | 5 | | | | | |
| | 16 | 15 | | | | | | | |
| | 64 | 29 | | 0 | | | | | |

Intratracheal Activity (Aerosol Application)

| Cpd. of Ex. No. | No. of Dogs | No. of Aerosol Actuations (dose in γ/act.) | Minutes 5 | 30 | 60 | 90 | 120 | 150 | 180 | 240 |
|---|---|---|---|---|---|---|---|---|---|---|
| 1 | 5 | 1-(375) | 1-2 min. 68-90 | 24-68 | 10-58 | 0-40 | | | | |
| 3 | 8 | 1-(400) | 1-2 min. 60-100 | 37-67 | 10-55 | 10-30 | 0-20 | | | |
| 5 | 3 | 1-(400) | 2 min. 30-75 | 30-58 | 30 | | 13 | | | |
| | 6 | 2-(400) | 1-2 min. 32-80 | 41-87 | 24-87 | | 15-80(b) | | | |
| 30 | 3 | 1-(269) | 3 min. 35 | 34 | 36 | | 31(a) | | | |

-continued

Intratracheal Activity (Aerosol Application)

| Cpd. of Ex. No. | No. of Dogs | No. of Aerosol Actuations (dose in γ/act.) | Minutes 5 | | 30 | 60 | 90 | 120 | 150 | 180 | 240 |
|---|---|---|---|---|---|---|---|---|---|---|---|
| | 3 | 2-(269) | 1-2 min. 41 | | | 45 | | 40 | | | |
| | 3 | 4-(260) | 1-2 min. 54 | | 65 | 63 | | 55 | | | |
| 112 | | 1-(282) | (C) | 50 | 41 | 38 | | 19 | | 0 | 0 |
| | | 1-(282) | (C) | 53 | 23 | 30 | | 30 | | 43 | 37 |
| | | 1-(282) | (H) | 44 | 28 | 47 | | 35 | 33 | | |
| | | 1-(282) | (C) | 59 | 39 | 37 | | 20 | | 0 | 0 |
| | | 1-(282) | (H) | 50 | 33 | 26 | | 29 | | 21 | 21 |
| | | 2-(282) | (H) | 17 | 20 | 13 | | 3 | | 2 | 0 |
| | | 2-(282) | (C) | 36 | 71 | 48 | | 26 | | 0 | 0 |
| | | 2-(282) | (C) | 73 | 68 | 60 | | 35 | | 13 | 13 |
| | | 4-(282) | (H) | 53 | 56 | 50 | | 46 | | 51 | 49 |
| | | 4-(282) | (H) | 53 | 37 | 46 | | 57 | | 54 | 54 |
| | | 4-(282) | (H) | 48 | 20 | 12 | | 0 | | | 0 |
| 116 | | 2-(296) | (H) | 7 | 0 | 27 | | 20 | | 0 | 0 |
| | | 2-(296) | (H) | 32 | 37 | 40 | | 29 | | 14 | 0 |
| 118 | 5 | 2-(266) | | 60 | 44 | 36 | | 32 | | | |
| | 4 | 4-(266) | | 56 | 43 | 34 | | 21 | | | |
| 120 | | 1-(200) | (C) | 32 | 32 | 0 | | | | | |
| | | 1-(200) | (C) | 33 | 23 | | | | | | |
| | | 2-(200) | (H) | 52 | 40 | 44 | | 4 | | 0 | |
| | | 2-(200) | (C) | 100 | 87 | 56 | | 0 | | 0 | |
| | | 2-(200) | (C) | 56 | 39 | 53 | | 0 | | 0 | |
| | | 4-(200) | (C) | 100 | 100 | 70 | | 80 | | 50 | |
| | | 4-(200) | (C) | 71 | 74 | 60 | | 34 | | 20 | 0 |
| 123 | | 1-(275) | (H) 19 | | 26 | 26 | 4 | 7 | | | |
| | | 1-(275) | (H) 17 | | 55 | 17 | | 24 | 50 | 10 | 40 |
| | | 2-(275) | (C) 73 | | 38 | 13 | | 0 | | 0 | |
| | | 2-(275) | (C) 15 | | 4 | 0 | | | | | |
| | | 2-(275) | (H) 48 | | 49 | 58 | | 36 | | 64 | 48 |
| | | 4-(275) | (H) 61 | | 56 | 72 | | 37 | | 22 | 0 |
| | | 4-(275) | (C) 60 | | 55 | 59 | | 36 | | 29 | 25 |
| 139 | 2 | 1-(222) | (H) 43 | | 33 | 19 | | 15 | | | |
| | 3 | 2-(222) | (H) | (C) 71 | 53 | 33 | | 13 | | | |
| | 3 | 4-(222) | (H) | (C) 83 | 64 | 52 | | 23 | 18 | | |
| 145 | 5 | 1-(250) | (H) | 48 | 45 | 37 | | 38 | 32 | | 33 |
| | 5 | 2-(250) | (H) | 73 58 | 45 | | 49 | 33 | | 35 | |
| | 3 | 4-(250) | (H) | 88 | 70 | 62 | | 55 | 54 | | 50 |
| Ref. Cpd. I | 8 | 1-(300) | | 38-98 | 0-67 | 0-18 | | | | | |
| Ref. Cpd. II | 2 | 1-(125) | | 60-70 | 0 | | | | | | |
| | 4 | 2-(125) | | 57-80 | 0-30 | | | | | | |

Notes
(a) after 180 minutes the values were 29, 36, and 32, respectively; and after 240 minutes the values were 11, 40, and 43, respectively.
(b) after 180 minutes the values were 12 and 12-78, respectively; and after 240 minutes (for 2 dogs) the value for the two dose level was 18-77.

Intraduodenal Activity
Bronchodilation in Percent
Minutes after Medication

| Cpd. of Ex. No. | No. of Dogs | Dose (salt) mcg/kg | 5 | 10 | 30 | 60 | 120 | 180 | 240 | 300 |
|---|---|---|---|---|---|---|---|---|---|---|
| 30 | 4 | 70 | | 38* | 45 | 42 | 42* | 42 | 25* | |
| | 4 | 140 | | 30 | 35 | 36 | 45 | 40 | 47 | |
| | 4 | 280 | | 75 | 71 | 64* | 56 | 50 | 45* | 37* |
| | | | Mean of 3 dogs | | | | | | | |
| 135 | 3 | 25 | 18 | — | | 56 | 55 | 45 | 34 | 27 |
| | 3 | 50 | 31 | | 56 | 74 | 73 | 64 | 51 | 37 |
| | | | (36 after 6 hrs.) | | | | | | | |
| 127 | | 450 | | | 0 | 0 | | | | |
| | | 450 | 16 | | 16 | 0 | | | | |
| | | | (0 aftr 90 min.) | | | | | | | |
| 112 | 1 | 68 | 50 | 0 | | | | | | |
| | 1 | 136 | 42 | 59 | 67 | 53 | 0 | | | |
| 145 | 4 | 20 | 33 | | 32 | 32 | 33 | 29 | 25 | 23 |
| | 7 | 80 | 53 | | 48 | 45 | 49 | 32 | 30 | |
| | 6 | 160 | 82 | | 81 | 81 | 63 | 48 | 32 | 37 |
| 146 | 2 | 38 | 60 | | 39 | 39 | 26 | 33 | 24 | 13 |
| 149 | 1 | 5 | 0 | | 7 | 13 | 5 | 9 | 0 | |
| | 1 | 40 | 78 | | 52 | 44 | 31 | — | 35 | 35 |
| | 1 | 160 | 72 | | 61 | 56 | 11 | 22 | 23 | |
| 150 | 1 | 32 | 12 | | 12 | 12 | 0 | 0 | | |
| | 1 | 128 | 68 | | 68 | 61 | 61 | 45 | 39 | |
| 151 | 1 | 32 | 24 | | 40 | 36 | 36 | 28 | | 20 |
| | 1 | 128 | 54 | | 63 | 66 | 66 | 66 | | 43 |
| 152 | 1 | 32 | 6 | | 6 | 17 | 48 | 45 | 45 | 21 |
| | 1 | 128 | 6 | | 43 | 59 | 51 | 65 | 59 | 54 |
| 156 | 2 | 200 | 18 | | 27 | 21 | 6 | 20 | 21 | 19 |

| | | -continued | | | | | | | |
|---|---|---|---|---|---|---|---|---|---|
| | 2 | 600 | 30 | | 55 | 48 | 24 | 3 | 12 |
| 157 | 1 | 1000 | 0 | | 29 | 0 | 0 | 0 | |
| | 1 | 1000 | 0 | | 13 | 0 | 0 | 0 | |
| | 1 | 10,000 | 3 | | 20 | 45 | 43 | 36 | 35 |
| Ref. | 3 | 35 | | 34 | 41 | 44 | 27 | 3 | |
| Cpd. I | 1 | 70 | | 40 | 60 | 35 | 30 | — | 0 |
| | 3 | 280 | | 66 | 59 | 46 | 54 | 30 | |
| Ref. | 3 | 30 | | 9 | 5 | 0 | | | |
| Cpd. II | 5 | 120 | | 28 | 25 | 19 | | | |
| Ref. | 3 | 25 | | 45 | — | 51 | 43 | 0 | |
| Cpd. III | 3 | 50 | | 13 | 42 | 56 | 71 | 53 | 34 | 6 |

Bronchodilator Test Method II

In this method bronchodilator activity in vitro was determined by testing the effect of graded doses of the test compounds on guinea pig bronchioles constricted by carbachol, using the technique reported by Sollman and von Oettingen, Proc. Soc. Exp. Biol. Med., 25, 692 (1928) as modified by Tainter, Pedden, and James, J. Pharm. Exp. Ther. 51, 371 (1934) and by Luduena, von Euler, Tullar, and Lands, Arch. intern. Pharmacol. III, 392 (1957).

Representative results which were obtained in this test are set forth in the following table.

| | Bronchodilator Action | | | |
|---|---|---|---|---|
| Cpd. of Ex. No. | $ED_{50}$ mcg(base) | Dose mcg(base) | No. of Lungs | Duration(min) Mean |
| Ref. Cpd. I | 0.18 | 0.32 | 6 | 5 ± 1.4 |
| Ref. Cpd. II | | 0.75 | 17 | 5 |
| 1 | 0.23 | 0.5 | 6 | 9 ± 1.0 |
| 2 | 0.28 | 0.5 | 9 | 9 ± 1.1 |
| 3 | 0.6 | 1.2 | 6 | 18 ± 4 |
| 5 | 0.94 | 2 | 5 | 18 ± 4.2 |
| 4 | 0.45 | 1 | 7 | 20 ± 3 |
| 13 | 0.45 | 0.79 | 6 | 15 ± 1.7 |
| 6 | 1.3 | 3.2 | 6 | 43 ± 3.7 |
| 71 | 0.63 | 2 | 5 | 26 |
| 7 | 23 | 32 | 6 | 85 ± 17 |
| 15 | 1.3 | 3.2 | 6 | 53 ± 7 |
| 29 | 1.1 | 3.2 | 7 | 34 ± 6.4 |
| 30 | 3.2 | 10 | 8 | 60 ± 9.6 |
| 33 | 6.9 | 10 | 5 | 32 ± 5 |
| 58 | 1.4 | 2.4 | 6 | 12 ± 2.5 |
| 59 | 1.2 | 3.2 | 6 | 25 ± 5.6 |
| 89 | 6.4 | 15 | 5 | 125 ± 31 |
| 138 | 0.46 | 1.5 | 6 | 25.4 ± 3.5 |
| 141 | 13.6 | 25 | 6 | 17 ± 6.7 |
| 112 | 4.4 | 10 | 6 | 104.1 ± 34.9 |
| 139 | 2.64 | 6 | 6 | 29.8 ± 4.4 |
| 143* | 1.53 | 2 | 6 | 29.2 ± 10.2 |
| 140* | | 25 | 3 | >30 |
| 144 | | 500 | 5 | 83 ± 26.8 |
| 145 | 0.25 | 1 | 6 | >72 |
| 147* | 1.9 | 5 | 6 | 15.9 ± 3.3 |
| 149* | 0.91 | 2 | 6 | 13.2 ± 1.9 |
| 150 | [9.3]** | 10 | 6 | 25.5 ± 16.2 |
| 151 | 5.1 | 10 | 3 | 67.3 ± 33.7 |

*Doryl conc. 1:10 million (instead of 1:5 million as in the other instances)
**$ED_{30}$

CARDIOVASCULAR STUDIES

The effect of a rapid intravenous injection on the heart rate was conducted in anesthetized dogs under normal respiration. A few open-chest dogs were also tested. Increase in heart rate was measured by using an electrocardiograph attached to the dog. Readings were taken every 0.5–1 minute for the first 10 minutes and every 2–5 minutes thereafter until recovery. In some cases, several doses and more than one compound were tested alternately in the same dog. The blood pressure effect was simultaneously recorded. Tests carried out in this way demonstrated that the esters of Formula I and Formula II had much less cardiovasular stimulating effect than the corresponding unesterified phenols.

| Effect on the Heart Rate in the Anesthetized Dog | | | |
|---|---|---|---|
| Cpd. of Ex. No. | No. of Dogs | Intravenous Dose (salt) mcg/kg | Mean Maximal Increase in the Heart Rate (Beats/Minute) (%) |
| 135 | 3 | 0.25 | 5 |
| | 3 | 1 | 10 |
| | 3 | 8 | 17 |
| 139 | 1 | 5 | 6 |
| | | 25 | 28 |
| | | 50 | 35 |
| 149 | 2 | 0.8 | 19 |
| | 3 | 6.4 | 47 |
| | 1 | 32.0 | 70 |
| 151 | 1 | 32 | 18 |
| | | 128 | 24 |
| 148 | 1 | 6.5 | 32 |
| | | 32.5 | 58 |
| 30 | 4 | 70 | 9 |
| | 3 | 140 | 15 |
| | 3 | 280 | 28 |
| 145 | 5 | 1.25 | 9 |
| | 5 | 5.0 | 13 |
| | 5 | 20 | 27 |
| Ref. Cpd. I | 3 | 0.17 | 20 |
| | 4 | 0.35 | 32 |
| | 6 | 0.7 | 44 |
| Ref. Cpd. II | 5 | 0.15 | 26 |
| | 5 | 0.3 | 35 |
| | 5 | 0.6 | 50 |
| Ref. Cpd. III | 3 | 0.25 | 9 |
| | 3 | 1 | 15 |
| | 3 | 4 | 34 |

| Effect on Diastolic Blood Pressure in the Anesthetized Dog | | | |
|---|---|---|---|
| Cpd. of Ex. No. | No. of Dogs | Intravenous Dose (salt) mcg/kg | Mean Decrease in Diastolic Blood Pressure in % |
| 30 | 4 | 70 | 2 |
| | 3 | 140 | 11 |
| | 3 | 280 | 11.5 |
| 145 | 5 | 1.25 | 7 |
| | 5 | 5.0 | 12 |
| | 5 | 20 | 20 |
| 151 | 1 | 32 | 10 |
| | | 128 | 10 |
| Ref. Cpd. I | 3 | 0.17 | 13 |
| | 4 | 0.35 | 33 |
| | 7 | 0.7 | 41 |
| Ref. Cpd. II | 6 | 0.15 | 12 |
| | 5 | 0.3 | 32 |
| | 7 | 0.6 | 40 |

We claim:

1. An ester of 3,4-dihydroxy-alpha-(amino- and N-substituted amino-methyl)benzyl alcohol having the formula

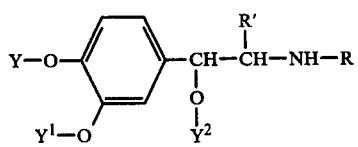

wherein
R is hydrogen, alkyl having 1–4 carbon atoms, or cycloalkyl having 3–6 carbon atoms;

R' is hydrogen or ethyl;

Y is an acyl member which is alkanoyl having 1-22 carbon atoms, alkenoyl having one or two double bonds and having 4-22 carbon atoms, cycloalkyl—$C_nH_{2n}$—CO— having a total of 4-10 carbon atoms of which 3-7 are ring carbon atoms in cycloalkyl and wherein n is zero, one or two, 1- or 2-adamantanecarbonyl, phenoxyacetyl, naphthalenecarbonyl, or Z—$C_nH_{2n}$—CO— wherein n is zero, one or two and Z is phenyl or phenyl substituted by 1-3 members of the group consisting of alkyl having 1-4 carbon atoms, halo, or trifluoromethyl; and $Y^1$ and $Y^2$ are the same or different and are hydrogen or one of the acyl members defined by Y, at least one of Y and $Y^1$ being Z—$C_nH_{2n}$—CO— or a pharmaceutically acceptable acid-addition salt thereof.

2. A compound according to claim 1, wherein Y and $Y^1$ are the same or different and each is Z—$C_nH_{2n}$—CO—.

3. A compound according to claim 2 wherein $Y^2$ and R' are hydrogen.

4. A compound according to claim 2 wherein n is zero.

5. A compound having the formula

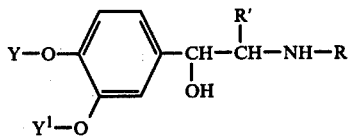

wherein

R is hydrogen, alkyl having 1-4 carbon atoms, or cycloalkyl having 3-6 carbon atoms;

R' is hydrogen or ethyl;

Y and $Y^1$ are the same or different and each is Z—$C_nH_{2n}$—CO— wherein n is zero, and Z is phenyl or phenyl substituted by 1-3 members of the group consisting of alkyl having 1-4 carbon atoms, halo or trifluoromethyl or a pharmaceutically acceptable acid-addition salt thereof.

6. A compound according to claim 5 wherein R' is hydrogen.

7. A compound according to claim 6 wherein R is isopropyl.

8. A compound according to claim 5 wherein R' is ethyl.

9. A compound according to claim 8 wherein R is tertbutyl.

10. A compound having the formula

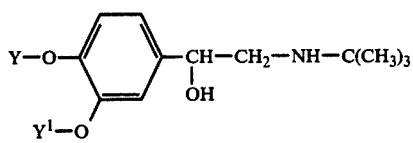

wherein

Y and $Y^1$ are the same or different and each is Z—$C_nH_{2n}$—CO— wherein n is zero, and Z is phenyl or phenyl substituted by 1-3 members of the group consisting of alkyl having 1-4 carbon atoms, halo, or trifluoromethyl or a pharmaceutically acceptable acid-addition salt thereof.

11. A compound according to claim 10 wherein each of Y and $Y^1$ is alkylbenzoyl.

12. A compound according to claim 11 wherein alkylbenzoyl is toluyl.

13. A compound according to claim 1 wherein one of Y and $Y^1$ is Z—$C_nH_{2n}$—CO— and the other is alkanoyl.

14. A compound according to claim 13 wherein n is zero.

15. A compound having the formula

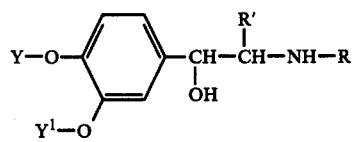

wherein

R is hydrogen, alkyl having 1-4 carbon atoms, or cycloalkyl having 3-6 carbon atoms;

R' is hydrogen or ethyl;

one of Y and $Y^1$ is an acyl member which is alkanoyl having 1-22 carbon atoms, and the other is Z—$C_nH_{2n}$—CO— wherein n is zero, and Z is phenyl or phenyl substituted by 1-3 members of the group consisting of alkyl having 1-4 carbon atoms, halo, or trifluoromethyl or a pharmaceutically acceptable acid-addition salt thereof.

16. A compound according to claim 15 wherein R' is hydrogen.

17. A compound according to claim 15 wherein R' is ethyl.

18. A compound having the formula

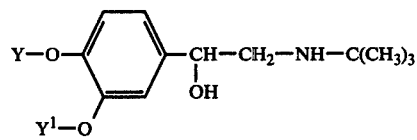

wherein one of Y and $Y^1$ is an acyl member which is alkanoyl having 1-22 carbon atoms, and the other is Z—$C_nH_{2n}$—CO— wherein n is zero, and Z is phenyl or phenyl substituted by 1-3 members of the group consisting of alkyl having 1-4 carbon atoms, halo, or trifluoromethyl or a pharmaceutically acceptable acid-addition salt thereof.

19. A compound according to claim 18 wherein one of Y and $Y^1$ is alkylbenzoyl.

20. A compound according to claim 19 wherein alkylbenzoyl is toluyl.

21. A compound according to claim 1 wherein one of Y and $Y^1$ is Z—$C_nH_{2n}$—CO— and the other is hydrogen.

22. A compound according to claim 21 wherein n is zero.

23. A compound according to claim 22 wherein $Y^2$ is hydrogen.

24. A compound having the formula

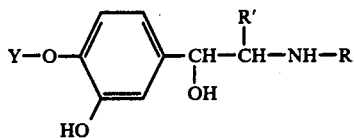

wherein
R is hydrogen, alkyl having 1-4 carbon atoms, or cycloalkyl having 3-6 carbon atoms;
R' is hydrogen or ethyl;
Y is Z—$C_nH_{2n}$—CO— wherein n is zero, and Z is phenyl or phenyl substituted by 1-3 members of the group consisting of alkyl having 1-4 carbon atoms, halo, or trifluoromethyl or a pharmaceutically acceptable acid-addition salt thereof.

25. A compound according to claim 24 wherein R' is ethyl.

26. A compound according to claim 24 wherein R' is hydrogen.

27. A compound according to claim 26 wherein R is tert-butyl.

28. A compound selected from the group consisting of:
3,4-bis(p-toluyloxy)-alpha-[1-(tert-butylamino)ethyl]-benzyl alcohol hydrochloride,
3,4-bis(p-toluyloxy)-alpha-[1-(isopropylamino)ethyl]-benzyl alcohol hydrochloride.

29. An ester of 3-hydroxymethyl-4-hydroxy-alpha-(amino-and N-substituted amino-methyl)benzyl alcohol having the formula

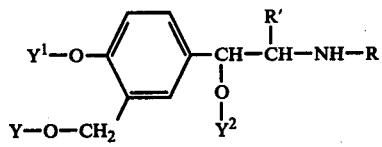

wherein
R is hydrogen, alkyl having 1-4 carbon atoms, or cycloalkyl having 3-6 carbon atoms;
R' is hydrogen or alkyl having 1-3 carbon atoms;
Y is an acyl member which is alkanoyl having 1-22 carbon atoms, alkenoyl having one or two double bonds and having 4-22 carbon atoms, cycloalkyl—$C_nH_{2n}$—CO— having a total of 4-10 carbon atoms of which 3-7 are ring carbon atoms in cycloalkyl and wherein n is zero, one or two, 1- or 2-adamantanecarbonyl, phenoxyacetyl, naphthalenecarbonyl, or Z—$C_nH_{2n}$—CO— wherein n is zero, one or two and Z is phenyl or phenyl substituted by 1-3 members of the group consisting of alkyl having 1-4 carbon atoms, halo, or trifluoromethyl; and
$Y^1$ and $Y^2$ are the same or different and are hydrogen or one of the acyl members defined by Y,
at least one of Y and $Y^1$ being Z—$C_nH_{2n}$—CO— or a pharmaceutically acceptable acid-addition salt thereof.

30. A compound according to claim 29 wherein $Y^2$ is hydrogen.

31. A compound according to claim 30 wherein R' is alkyl.

32. A compound according to claim 30 wherein R' is hydrogen.

33. A compound according to claim 32 wherein R is alkyl.

34. A compound according to claim 33 wherein R is tert-butyl.

35. A compound according to claim 34 wherein Y and $Y^1$ are the same or different and each is Z—$C_nH_{2n}$—CO—.

36. A compound according to claim 35 wherein n is zero.

37. A compound according to claim 34 wherein one of Y and $Y^1$ is alkanoyl and the other is Z—$C_nH_{2n}$—CO—.

38. A compound according to claim 37 wherein n is zero.

39. A compound according to claim 34 wherein $Y^1$ is hydrogen.

40. 3,4-Bis(p-toluyloxy)-alpha-[(isopropylamino)methyl]benzyl alcohol methanesulfonate according to claim 7.

41. 3-Benzoyloxy-4-p-toluyloxy-alpha-[(tert-butylamino)methyl]benzyl alcohol methanesulfonate according to claim 10.

42. 3,4-Bis(benzoyloxy)-alpha-[(tert-butylamino)methyl]benzyl alcohol hydrochloride according to claim 10.

43. 3,4-Bis(p-toluyloxy)-alpha-[(tert-butylamino)methyl]benzyl alcohol methanesulfonate according to claim 12.

44. 3,4-Bis(m-toluyloxy)-alpha-[(tert-butylamino)methyl]benzyl alcohol methanesulfonate according to claim 12.

45. 3-Acetoxy-4-p-toluyloxy-alpha-[(tert-butylamino)methyl]benzyl alcohol methanesulfonate according to claim 20.

46. 3-Hydroxy-4-m-toluyloxy-alpha-[(tert-butylamino)methyl]benzyl alcohol methanesulfonate according to claim 27.

* * * * *

UNITED STATES PATENT AND TRADEMARK OFFICE
CERTIFICATE OF CORRECTION

PATENT NO. : 4,138,581

DATED : February 6, 1979

INVENTOR(S) : Hiroaki Minatoya, Benjamin F. Tullar and Walter D. Conway

It is certified that error appears in the above-identified patent and that said Letters Patent are hereby corrected as shown below:

In the title on the face page of the patent and in Column 1, "3(HYDROXY OR HYDROXYMETHYL)-4-(HYDROXY)-$\alpha$-(AMINOMETHYL)BENZYL ALCOHOLS" should read -- 3-(HYDROXY OR HYDROXYMETHYL)-4-HYDROXY-$\alpha$-(AMINOMETHYL)BENZYL ALCOHOLS --.

Column 1, line 9, "496,539" should read -- 496,538 --.

Column 5, lines 23-24, "alkanolylamino" should read -- alkanoylamino --.

Column 8, line 24, "is" should read -- in --.

Column 10, lines 1-2, "hydrofluroric" should read -- hydrofluoric --.

Column 10, line 50, "20-$\alpha$°C." should read -- 20-60°C. --.
Column 10, line 51, "20-=" should read -- 20-50 --.

UNITED STATES PATENT AND TRADEMARK OFFICE
CERTIFICATE OF CORRECTION

PATENT NO.  : 4,138,581
DATED       : February 6, 1979
INVENTOR(S) : Hiroaki Minatoya, Benjamin F. Tullar and Walter D. Conway It is certified that error appears in the above-identified patent and that said Letters Patent are hereby corrected as shown below:

Column 10, line 67, "-(YO-CH -Y-O-CH2-)" should be deleted and -- 3-(Y-O-CH$_2$-) -- should be inserted in its place.

Column 11, line 59, "selectivity" should read --selectively--.

Column 12, lines 14-15, "acyloxphenyl" should read -- acyloxyphenyl -- and "(R'$_\lambda$)" should read -- (R') --.

Column 12, lines 36-37, "(R$_\lambda^2$)" should read -- (R') --.

Column 12, line 48, "R-NH$_{22}$" should read -- R-NH$_2$ --.

Column 73, Claim 9, line 2, "tertbutyl" should read -- tert-butyl --.

Signed and Sealed this

Sixth Day of November 1979

[SEAL]

Attest:

RUTH C. MASON
Attesting Officer

LUTRELLE F. PARKER
Acting Commissioner of Patents and Trademarks

UNITED STATES PATENT AND TRADEMARK OFFICE

CERTIFICATE EXTENDING PATENT TERM
UNDER 35 U.S.C. 156

Patent No.    : 4,138,581

Dated         : Feb. 6, 1979

Inventor(s)   : Minatoya et al.

Patent Owner  : Sterling Drug Inc.

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

I have caused the seal of the Patent and Trademark Office to be affixed this Eighteenth day of April, 1986.

Donald J. Quigg

Assistant Secretary and Commissioner of Patents and Trademarks